US010156479B2

(12) United States Patent
Liu et al.

(10) Patent No.: US 10,156,479 B2
(45) Date of Patent: Dec. 18, 2018

(54) SPATIAL-DOMAIN LOW-COHERENCE QUANTITATIVE PHASE MICROSCOPY

(71) Applicant: University of Pittsburgh—Of the Commonwealth System of Higher Education, Pittsburgh, PA (US)

(72) Inventors: Yang Liu, Sewickley, PA (US); Randall E. Brand, Sewickley, PA (US); Hoa V. Pham, Hanoi (VN); Shikhar Fnu, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 204 days.

(21) Appl. No.: 14/562,092

(22) Filed: Dec. 5, 2014

(65) Prior Publication Data
US 2015/0204728 A1 Jul. 23, 2015

Related U.S. Application Data

(63) Continuation-in-part of application No. 13/695,230, filed as application No. PCT/US2011/035771 on May 9, 2011.
(Continued)

(51) Int. Cl.
*G01J 9/02* (2006.01)
*G02B 21/14* (2006.01)
(Continued)

(52) U.S. Cl.
CPC ............ *G01J 9/02* (2013.01); *G01N 15/1429* (2013.01); *G01N 15/1434* (2013.01);
(Continued)

(58) Field of Classification Search
CPC .................................................. G01N 21/4795
See application file for complete search history.

(56) References Cited

U.S. PATENT DOCUMENTS 5,841,577 A    11/1998  Wachman et al.
5,938,617 A *   8/1999  Vo-Dinh .............. A61B 5/0059
                                                                    436/171
(Continued)

OTHER PUBLICATIONS

Sarunic, Marinko V., Seth Weinberg, and Joseph A. Izatt. "Full-field swept-source phase microscopy." Optics letters 31.10 (2006): 1462-1464.*
(Continued)

*Primary Examiner* — Tri Ton
*Assistant Examiner* — Rufus Phillips
(74) *Attorney, Agent, or Firm* — Eckert Seamans Cherin & Mellott, LLC; Philip E. Levy

(57) ABSTRACT

Systems, methods and other embodiments associated with spatial-domain Low-coherence Quantitative Phase Microscopy (SL-QPM) are described herein. SL-QPM can detect structural alterations within cell nuclei with nanoscale sensitivity (0.9 nm) (or nuclear nano-morphology) for "nano-pathological diagnosis" of cancer. SL-QPM uses original, unmodified cytology and histology specimens prepared with standard clinical protocols and stains. SL-QPM can easily integrate in existing clinical pathology laboratories. Results quantified the spatial distribution of optical path length or refractive index in individual nuclei with nanoscale sensitivity, which could be applied to studying nuclear nano-morphology as cancer progresses. The nuclear nano-morphology derived from SL-QPM offers significant diagnostic value in clinical care and subcellular mechanistic insights for basic and translational research. Techniques that provide for depth selective investigation of nuclear and other cellular features are disclosed.

15 Claims, 57 Drawing Sheets

Related U.S. Application Data

(60) Provisional application No. 61/912,995, filed on Dec. 6, 2013.

(51) Int. Cl.
  *G01N 15/14* (2006.01)
  *G02B 21/36* (2006.01)

(52) U.S. Cl.
  CPC ......... *G01N 15/1475* (2013.01); *G02B 21/14* (2013.01); *G02B 21/365* (2013.01); *G01J 2009/0223* (2013.01); *G01J 2009/0253* (2013.01); *G01J 2009/0269* (2013.01); *G01N 2015/1402* (2013.01); *G01N 2015/1479* (2013.01)

(56) References Cited

U.S. PATENT DOCUMENTS

| | | | | |
|---|---|---|---|---|
| 9,008,378 | B2* | 4/2015 | Micheva | G02B 21/367 382/128 |
| 2007/0206197 | A1* | 9/2007 | Buckland | A61B 3/102 356/479 |
| 2011/0292399 | A1* | 12/2011 | Alphonse | G01B 9/02044 356/479 |
| 2013/0229663 | A1 | 9/2013 | Yang et al. | |
| 2015/0049343 | A1 | 2/2015 | Shaked et al. | |

OTHER PUBLICATIONS

Shikhar Uttam, Rajan K. Bista, Kevin Staton, Sergey Alexandrov, Serah Choi, Christopher J. Bakkenist, Douglas J. Hartman, Randall E. Brand, and Yang Liu, "Investigation of depth-resolved nanoscale structural changes in regulated cell proliferation and chromatin decondensation," Biomed. Opt. Express 4, 596-613 (2013).*

Matthew Rinehart, Yizheng Zhu, and Adam Wax, "Quantitative phase spectroscopy," Biomed. Opt. Express 3, 958-965 (2012).*

International Preliminary Report on Patentability, dated Jan. 4, 2016.

International Search Report, dated Mar. 2, 2015.

Wang P. et. al.: "Nanoscale nuclear architecture for cancer diagnosis beyond pathology via spatial-domain low-coherence quantitative phase microscopy", Journal of Biomedical Optics, (Nov./Dec. 2010) vol. 15 (6), p. 066028-1:066028-8.

Wang P. et. al.: "Spatial-domain low-coherence quantitative phase microscopy for cancer diagnosis", Opt Lett., (Sep. 2010) 35 (17), 2840-2842.

Uttam S., et. al.: "Correction of stain variations in nuclear refractive index of clinical histology specimens", Journal of Biomedical Optics, (Nov. 2011), 16 (11), 116013.

* cited by examiner

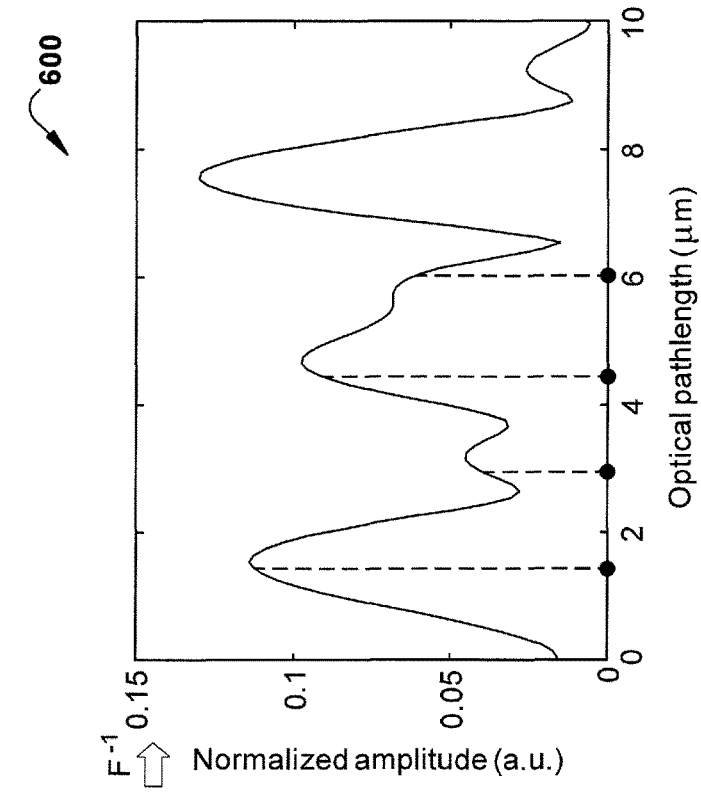
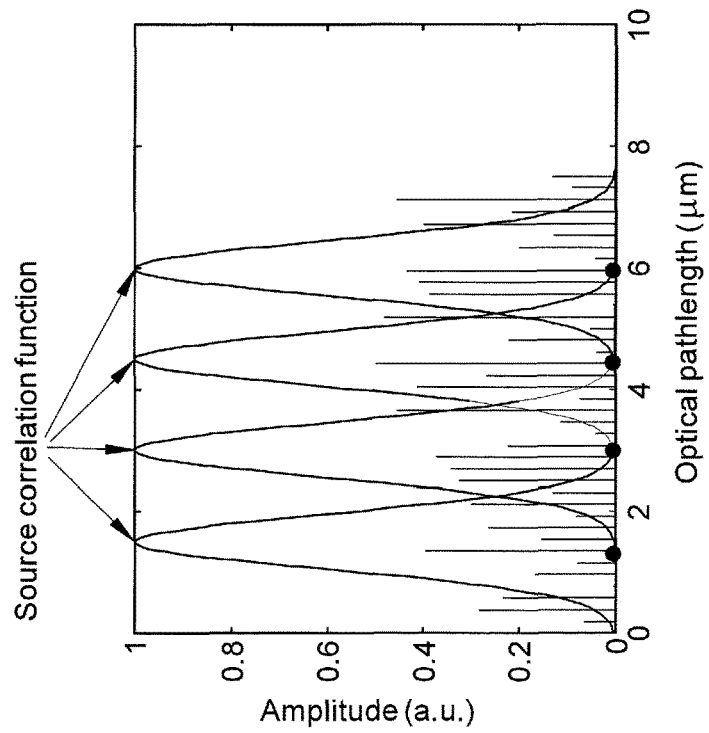
FIG. 7B
FIG. 7A

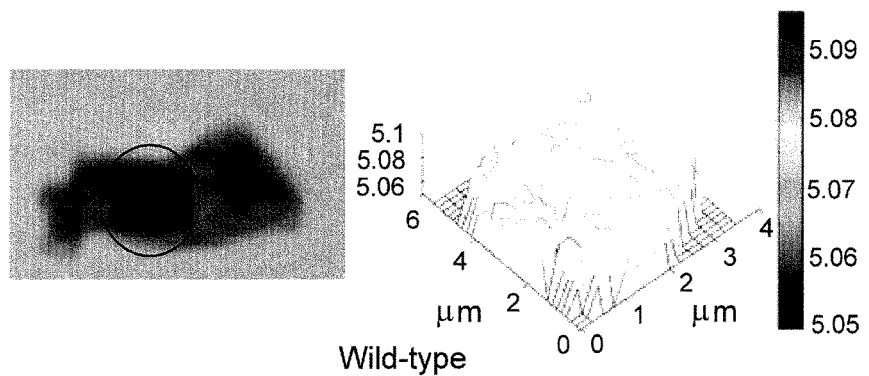
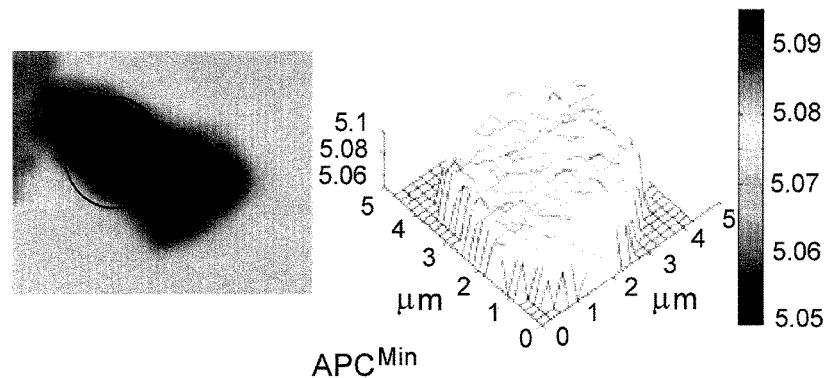
FIG. 14A  FIG. 14B
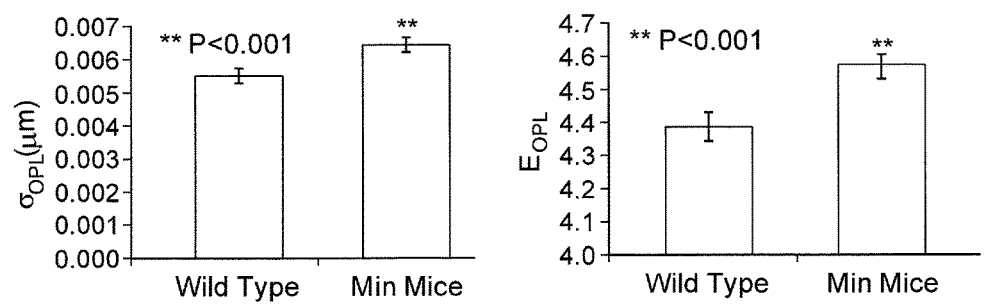
FIG. 14C

Low-risk Patient

High-risk Patient

Cytologically Indeterminate/Chronic Pancreatitis

Cytologically Indeterminate/Adenocarcinoma

Cytologically Malignant/Adenocarcinoma

Benign

Uninvolved

Malignant

Wild type     6 weeks dysplastic     4.5 months dysplastic (a) APC$^{Min}$ mouse model Normal     Benign     Malignant

SPATIAL-DOMAIN LOW-COHERENCE QUANTITATIVE PHASE MICROSCOPY

CROSS-REFERENCE TO RELATED APPLICATIONS

This application claims the benefit of U.S. Provisional Patent application Ser. No. 61/912,995 entitled "SPATIAL-DOMAIN LOW-COHERENCE QUANTITATIVE PHASE MICROSCOPY" and filed Dec. 6, 2013, and is a continuation-in-part of pending U.S. patent application Ser. No. 13/695,230 entitled "SPATIAL-DOMAIN LOW-COHERENCE QUANTITATIVE PHASE MICROSCOPY" and filed May 23, 2013, which is a U.S. national stage entry under 35 U.S.C. § 371 of international application PCT/US2011/035771 entitled "SPATIAL-DOMAIN LOW-COHERENCE QUANTITATIVE PHASE MICROSCOPY" and filed May 9, 2011, which claims priority to U.S. Provisional Patent Application 61/332,881 entitled "MULTI-MODE MULTI-DIMENSIONAL ELASTIC LIGHT SCATTERING SPECTROSCOPIC MICROSCOPY" and filed May 10, 2010. The entirety of the above-noted applications are incorporated by reference herein.

NOTICE ON GOVERNMENT FUNDING

This invention was made with government support under grant # EB016657 and grant # CA164433 awarded by the National Institutes of Health. The government has certain rights in the invention.

BACKGROUND

Quantitative knowledge of the structure of the cell has great importance for biomedical application. However, conventional light microscopy does not provide sufficient quantitative information on light propagation within sub-cellular organelles of a biological cell. For example, cancer is typically diagnosed on the basis of morphological changes, particularly alterations in nuclear structure, in the cell. Nuclear architectural alterations are examined by brightfield microscopy of cells stained with reagents such as Papanicolaou, Diff-Quik, Hematoxylin and Eosin stains; the observable changes in malignant cells include enlarged nuclear size, irregularity of nuclear shape and more prominent nucleoli. However, subtle changes in the nuclear architecture may not be easily detectable with conventional microscopy, especially in early stages of cancer development, which can delay definitive diagnosis until the malignant features of nuclear architectures become significant. While nanoscale changes in nuclear architecture can be assessed by electron microscopy, this approach is expensive, labor intensive, and requires specialized tissue or cell handling that can damage the sample and make it impractical for routine clinical use. Similarly, although optical phase microscopy uses the ultra-sensitivity of light interference effect to detect sub-cellular changes in architecture, quantitative phase imaging microscopy suffers from speckle noise that has significantly hampered its clinical utility. Thus, clinically practical techniques are needed to improve early detection of cancer, provide insight into the process of malignant transformation, and inform development of new diagnostic tools and therapeutic agents.

Phase contrast microscopy and differential interference contrast (DIC) microscopy are capable of detecting subtle subcellular structural alterations. They have been widely used to visualize transparent cells in biological research, in which a minute alteration in the phase or optical path length of internal cell structure, even just a few protein or DNA molecules, can be detected through the intensity differences in the image. Despite their ability to visualize transparent cells, the lack of quantitative phase information has become a limiting factor in many biological applications. Due to the significant technical advancement, quantitative phase microscopy has recently emerged as a superior phase microscopy technique, as it provides quantitative phase measurement of a biological cell with ultrasensitivity in detecting subtle dynamic changes in the subcellular structure. Despite these significant advances, its utility in clinical diagnosis of cancer is still limited, largely due to the speckle noise, special requirement on sample preparations, and the lack of known diagnostic parameters for cancer.

SUMMARY

The following presents a simplified summary of the innovation in order to provide a basic understanding of some aspects of the innovation. This summary is not an extensive overview of the innovation. It is not intended to identify key/critical elements of the innovation or to delineate the scope of the innovation. Its sole purpose is to present some concepts of the innovation in a simplified form as a prelude to the more detailed description that is presented later.

In aspects, the subject innovation can comprise a spatial-domain low-coherence quantitative phase microscopy (SL-QPM) apparatus. The apparatus can include a light source that produces white light, which can optionally be collimated (e.g., via a 4f imaging system that collimates the light from the light source, etc.). Additionally, the apparatus can comprise an objective lens that focuses the light on a sample, wherein the sample scatters at least a portion of the light back. The apparatus can further include a spectrograph that scans across backscattered light from the sample and a camera coupled to the spectrograph, wherein the camera measures backscattered light scanned by the spectrograph.

In other embodiments, the subject innovation can include a SL-QPM method. This method can include the acts of producing white light, optionally collimating the light from the light source, and focusing the light onto a sample, wherein the sample scatters at least a portion of the light back. Additionally, it can include the acts of scanning across backscattered light from the sample with a spectrograph and measuring the scanned light with an image acquisition device such as a camera coupled to the spectrograph.

To the accomplishment of the foregoing and related ends, certain illustrative aspects of the innovation are described herein in connection with the following description and the annexed drawings. These aspects are indicative, however, of but a few of the various ways in which the principles of the innovation can be employed and the subject innovation is intended to include all such aspects and their equivalents. Other advantages and novel features of the innovation will become apparent from the following detailed description of the innovation when considered in conjunction with the drawings.

BRIEF DESCRIPTION OF THE DRAWINGS

FIGS. 7A-7B illustrate an example optical path length (OPL) profile and the depth selective nature of the source correlation function.

FIGS. 14(A) and 14(B) show Papanicolaou-stained cytological images of representative intestinal epithelial cells from $APC^{Min}$ mice compared to those of wild-type mice obtained from a bright-field microscope and their corresponding OPL maps from the cell nuclei.

FIG. 14(C), shows the nuclear heterogeneity significantly increased in approximately 20 to 30 randomly selected intestinal epithelial cells from $APC^{Min}$ mice compared to those from wild-type mice.

DETAILED DESCRIPTION

Figure 1:
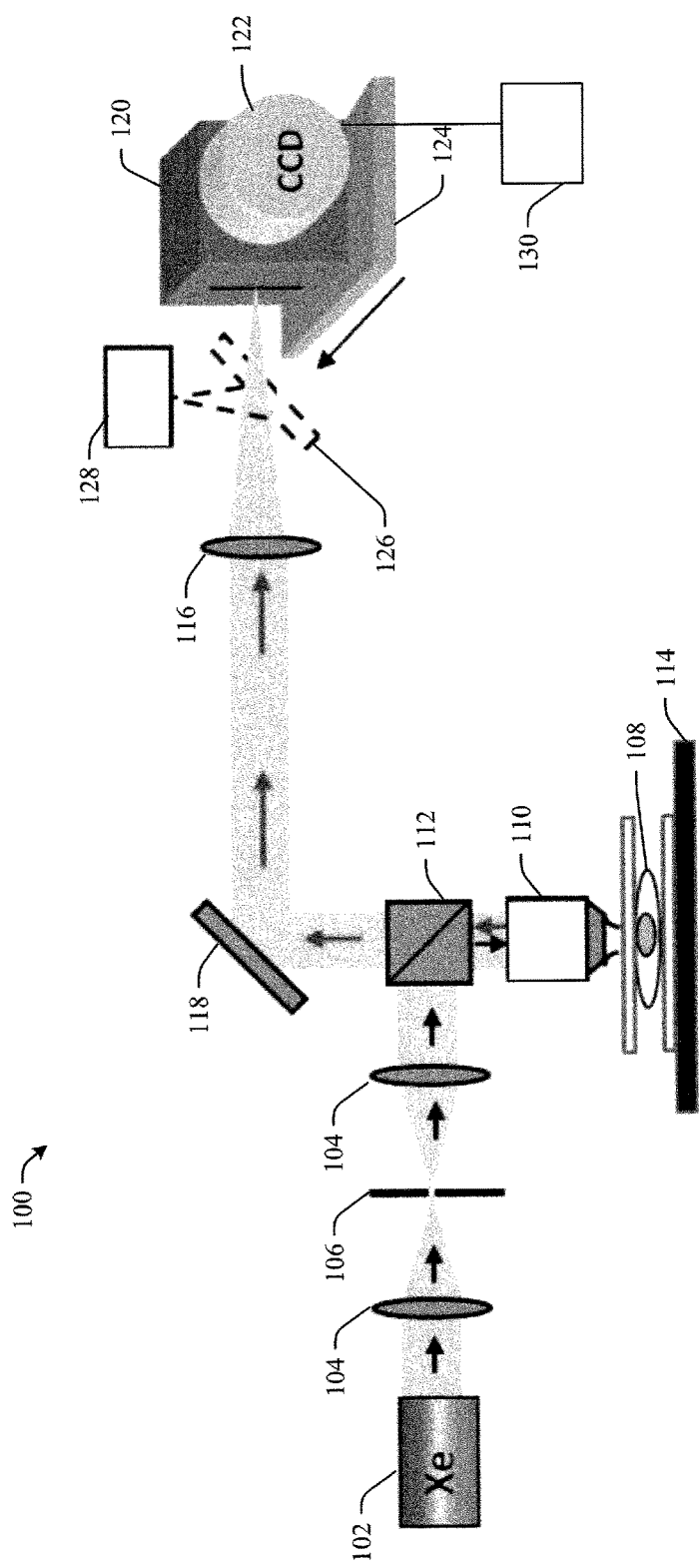
FIG. 1 illustrates a Spatial-domain Low-coherence Quantitative Phase Microscopy (SL-QPM) instrument in accordance with aspects of the innovation.

The innovation is now described with reference to the drawings, wherein like reference numerals are used to refer to like elements throughout. In the following description, for purposes of explanation, numerous specific details are set forth in order to provide a thorough understanding of the subject innovation. It may be evident, however, that the innovation can be practiced without these specific details.

Alterations in nuclear structure are the hallmark diagnostic characteristic of cancer cells. Even with well-established nuclear appearance according to tumor type and stage, definitive diagnosis of malignancy, particularly early in the disease course, is often challenging due to morphological similarity with certain benign conditions. Using a novel optical instrument, spatial-domain low-coherence quantitative phase microscopy (SL-QPM), it has been found that increased heterogeneity of nuclear architecture is diagnostically significant in cancer cells at a level more sensitive than conventional cytopathology. The spatial distribution of optical path length in the individual cell nuclei with nanoscale sensitivity can be quantified, and can be applied to studying nuclear heterogeneity as cancer progresses. The nanoscale nuclear architecture derived from this simple and practical optical instrument can offer significant diagnostic value in clinical care as well as subcellular mechanistic insights for basic and translational research.

The innovation, in aspects thereof, comprises apparatuses, systems and methods for spatial-domain low-coherence microscopy. FIG. 1 illustrates an example Spatial-domain Low-coherence Quantitative Phase Microscopy (SL-QPM) instrument 100 in accordance with aspects of the innovation. The hardware design of the SL-QPM 100 can include a broadband white light 102 (e.g., from a Xe-arc lamp) that can optionally be collimated (e.g., by a 4f imaging system (e.g., including lenses 104 and aperture 106) such as shown in example instrument 100, other optical elements (e.g., mirrors, lenses, apertures, etc.) or combinations thereof to collimate the light, etc.) and can be focused on the sample 108 by a mirror or lens (e.g., a low-NA objective lens 110 (e.g., NA=0.4)) via a beam splitter 112. The sample can be mounted on a sample stage 114. The resulting backscattering light can be collected and projected (e.g., by a tube lens 116 via a mirror 118, etc.) onto the slit of an imaging spectrograph 120 (e.g., from Acton Research, MA), which can be coupled with an image acquisition device (e.g., a camera such as a charge coupled device (CCD) camera) 122 (e.g., from Andor Technology, CT), which can be mounted on a scanning stage 124. Optionally, the system can also include a removal mirror 126 and a camera 128 to obtain optical images without the use of a spectrograph. The magnification of the system used to obtain results described herein was about 44, although greater or lesser magnifications could be obtained through variations of the components described above. By linearly scanning the slit of the spectrograph with a small (e.g., 10 μm) step size, the backscattering image can be acquired. In each scanning step, the camera or other image acquisition device (e.g., CCD camera, etc.) can record a matrix with x-axis corresponding to the wavelength and y-axis corresponding to the spatial position, resulting in a three-dimensional intensity cube I(x,y,k), where k represents the wavenumber. The system can include an internal processor and memory for performing calculations and processing, or data can be output to an external device such as a computer. In embodiments, the system can include a data analysis component 130 that can construct the three-dimensional intensity cube based at least in part upon data recorded by the camera (etc.) 122. The data analysis component 130 can also perform analytical techniques described herein, such as determining parameters based on data recorded by the camera (etc.) 122.

SL-QPM can use a common-path interferometric microscopy configuration, as shown in FIG. 1. Multiple technical characteristics of SL-QPM contribute to its high sensitivity and clinical applicability, including reflectance-mode, low spatial-coherence illumination from a thermal light source, and spectroscopic detection. Because of the reflectance-mode geometry, the phase matching condition can pick up the largest possible wave vectors in the Fourier-space representation of the refractive structure of the object, which carry information about its finest features. Compared to conventional transmission-mode light microscopy, the reflectance mode can effectively suppress the effect of absorption owing to the staining reagents commonly used in most clinical cytology or histology specimens and can highlight the interference signals. The illumination from a thermal light source coupled with a low-NA objective can provide a low transverse spatial-coherence length (e.g., in a range from less than about 500 nm to more than about 750 nm ($a_c \sim \lambda_0 = 2NA$)), which can serve as a virtual aperture to eliminate the speckle noise and can decompose a three-dimensional complex scattering medium into many one-dimensional channels. White-light spectroscopic detection can provide for the ability to quantify the phase information of the scattering object through the spectral analysis of wavelength-dependent interference signals. The glass substrate and tissue components of the histology slides can serve as a reference and a sample, respectively, that share a common path, effectively eliminating the slightest external disruptions that may compromise the ultrahigh sensitivity.

In other embodiments, the subject innovation can include methods of obtaining optical data regarding samples via systems, instruments, and configurations described herein. This data can be analyzed and processed to determine one or more parameters that characterize the data.

Figure 2:
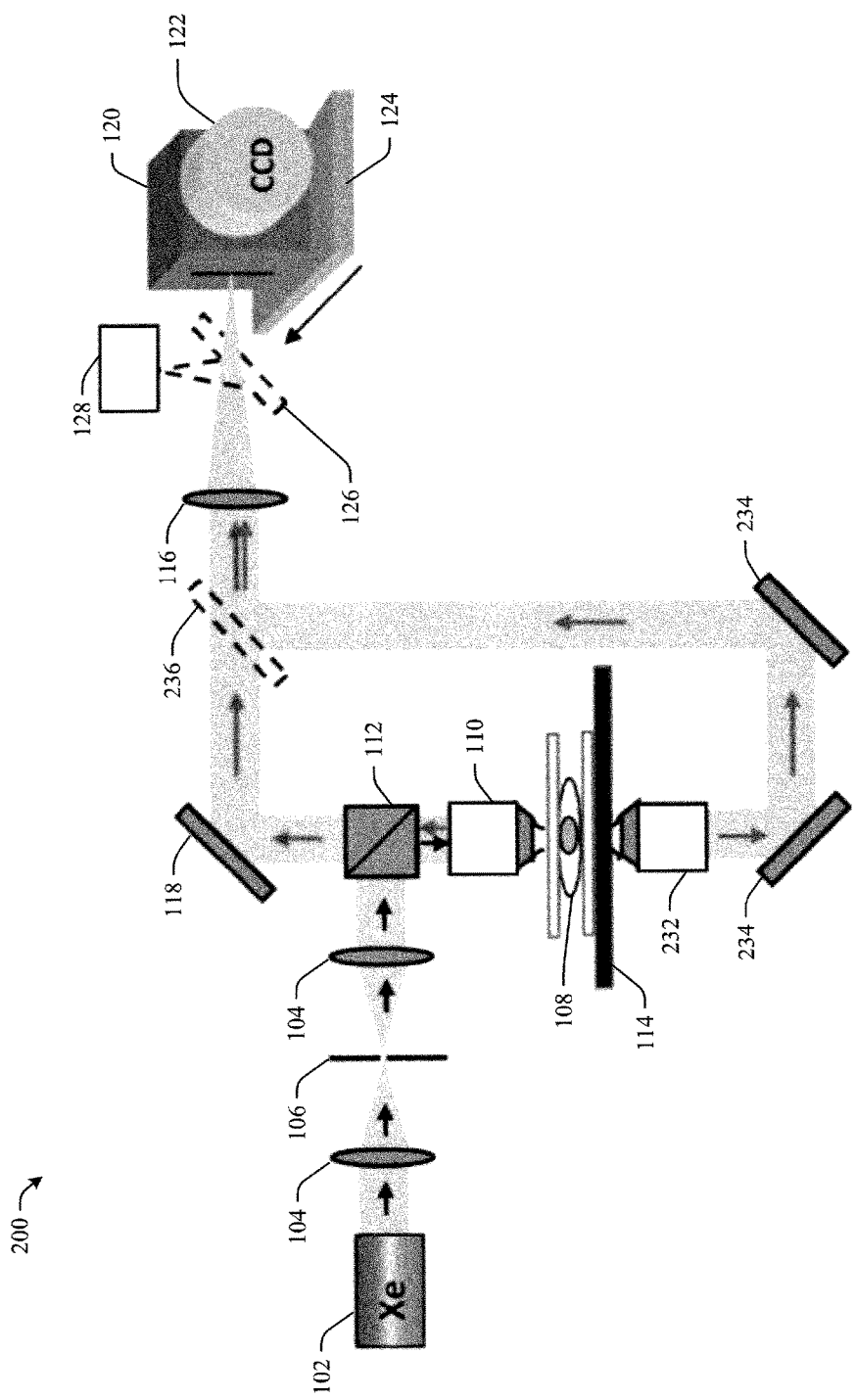
FIG. 2 illustrates an alternate embodiment of a SL-QPM system that incorporates a transmission-mode geometry.

FIG. 2 illustrates an alternate embodiment of a SL-QPM system 200 that incorporates a transmission-mode geometry. Additional transmission-mode components can be used to perform cytology and were used in connection with an example embodiment of the subject innovation in experiments described herein to record conventional cytology images for comparison. These additional components can include a second objective 232, one or more additional mirrors 234, and an additional removal mirror 236, so as to direct transmission-mode images to devices 128 or 122 in order to capture data. As shown in FIG. 2, an SL-QPM system can be incorporated with the functionality of conventional optical microscope, which can be accomplished by incorporating such an SL-QPM system into existing microscopes, or through novel devices providing both modes.

Alterations in nuclear structure are the hallmark diagnostic characteristic of cancer cells. However, even with well-established nuclear appearance according to tumor type and stage, definitive diagnosis of malignancy, particularly early in the disease course, is often challenging due to morphological similarity with certain benign conditions. Using a novel optical instrument described herein, spatial-domain low-coherence quantitative phase microscopy (SL-QPM), increased heterogeneity of nuclear architecture has been found to be diagnostically significant in cancer cells at a level more sensitive than conventional cytopathology. Systems and methods discussed herein can, in aspects, provide for diagnosis of medical conditions such as cancer, etc. via SL-QPM. Using these systems and methods, the spatial distribution of optical path length in the individual cell nuclei can be quantified with nanoscale sensitivity, which can be applied to studying nuclear heterogeneity as cancer progresses. The nanoscale nuclear architecture derived from this simple and practical optical instrument can be employed in a variety of settings, including offering significant diagnostic value in clinical care as well as subcellular mechanistic insights for basic and translational research.

As explained herein, spatial-domain low-coherence quantitative phase microscopy (SL-QPM) can be used to examine nuclear architecture in cancer cells. The low spatial-coherence length from a thermal light source and common-path configuration can minimize the notorious noise artifacts in quantitative phase microscopy, producing a speckle-free, nanoscale-sensitive map of the spatial variation of optical path length differences of the sub-cellular architecture. To better aid in the understanding of the innovation, experiments are described further herein, for example, experiments wherein nuclear architectural characteristics of cells from a genetically modified colorectal cancer cell line were examined at different levels of cell proliferation. Increased nuclear architectural heterogeneity that parallels the higher level of cell proliferation was observed in two cancer cell lines. These experimental results confirmed the ability of SL-QPM to differentiate benign from malignant cells in human cytological specimens, including the capability of SL-QPM to identify malignancy in cells characterized by pathologists as cytologically indeterminate. As indicated by the results discussed herein, SL-QPM can be useful in improving cancer diagnosis and mapping nuclear content and heterogeneity during carcinogenesis. With these techniques, for the first time, the refractive index of the cell nuclei on the original unmodified histology specimens was quantified. The results show that the average refractive index of the cell nucleus is significantly increased in malignant cells compared to that of the histologically normal cells. Because these techniques are simple, sensitive, do not require special tissue processing, and can be applied to archived specimens, they can be easily disseminated to all hospital settings. Additionally, early detection strategies and monitoring response to preventive and therapeutic interventions.

Using SL-QPM, nuclear architectural heterogeneity has been found to increase in parallel with the level of cell proliferation and techniques associated with the subject innovation are more sensitive than standard cytopathology at identifying as cancerous otherwise cytologically indeterminate abnormal cells from cancer patients. This nanoscale nuclear architectural characteristic has a wide variety of applications, including cancer diagnosis. Systems and methods of the subject innovation, such as SL-QPM, can provide numerous advantages of traditional systems, including ease of implementation, ultra-sensitivity of less than a nanometer, and direct applicability to clinical diagnosis. Using SL-QPM, speckle-free, nanoscale optical path length distribution has been obtained for the first time from the cell nucleus in original cytology specimens prepared with the standard clinical protocol without any special processing, such as fluorescence staining or coverslip removal. The simplicity of this optical instrument and applicability to clinical specimens make this technique easily translatable to basic research and clinical care settings.

Although, throughout the following discussion, reference is primarily to SL-QPM systems, methods, and techniques, other systems, methods, and techniques (such as multi-mode multi-dimensional elastic light scattering spectroscopic microscopy, etc.) described herein may be used additionally or instead of SL-QPM in a substantially similar manner.

In other aspects, the innovation described herein include systems and methods associated with a new imaging and spectroscopy instrument called multi-mode multi-dimensional elastic light scattering spectroscopic microscopy (MD-ELSM). In various embodiments, these systems and methods can collect the elastically scattered light from a scattering object (e.g., biological cell, physical objects) and can provide a new type of quantitative imaging contrast. MD-ELSM has the capability to characterize a full 3D scattering wave-vector with scattering wavelength, angle and azimuth angle mapped onto the Fourier plane, as well as onto the image plane, down to the single cell and sub-cellular level. MD-ELSM can uniquely quantify quantitative phase, optical path-length that light travels within a scattering object, average refractive index and its heterogeneity. Since MD-ELSM can be developed on the frame of a research microscope, it can easily incorporate various conventional imaging modes of phase contrast (qualitative), differential interference contrast and fluorescence microscopy for parallel registration of images with different modes.

Figure 3:
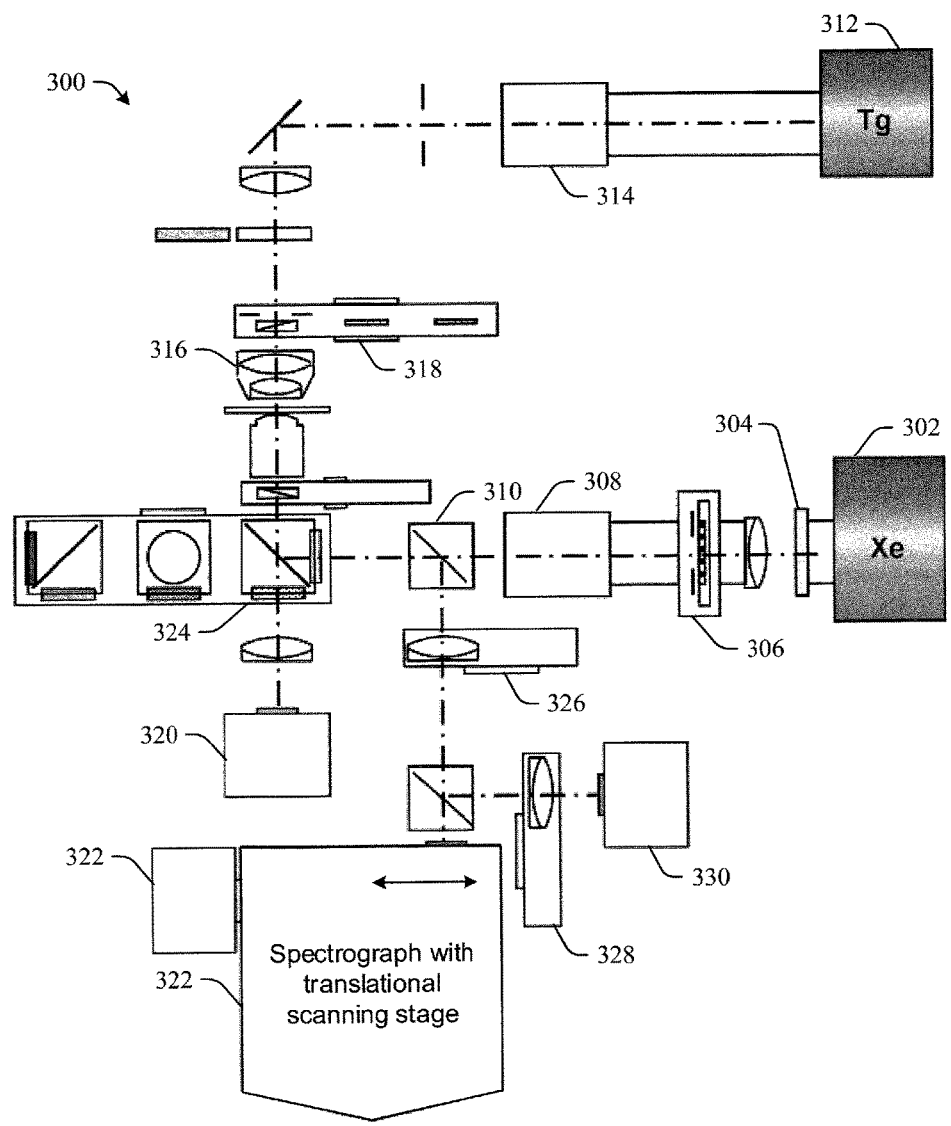
FIG. 3 illustrates an example schematic of a MD-ELSM system in accordance with aspects of the innovation.

FIG. 3 illustrates an example schematic of a MD-ELSM system 300 in accordance with aspects of the innovation. An MD-ELSM system can be built upon a research microscope, such as on an automated research microscope stand (e.g., from Zeiss, such as an AxioObserver Z1). The incident-light branch of the instrument can incorporate a broadband light source 302 such as a Xenon lamp. Optionally, a diffuser, e.g., a holographic diffuser 304 (e.g., from Edmund Optics), etc.) can be used to homogenize the incident beam for uniform illumination for the backscattering mode. A variable mask 306 can be included in the incident-light aperture plane in order to enable selection of the incident wave vector and illumination numerical aperture (INA), in addition to the conventional field plane iris, as can collimating optics 308 and a beam splitter 310. The transillumination branch of the instrument can incorporate one or more of a Tungsten or other similar lamp 312, collimating optics 314, a field-plane iris, or a high-NA condenser 316 which can have selectable optics 318 for phase contrast (phase ring), DIC (quarter wave-plate) and forward scattering mode. The imaging branch can switch between an image acquisition device (e.g., a camera, such as a CCD camera, etc.) 320 for direct image acquisition, and the scanned spectrographic imager (e.g., CCD imager, etc.) 322 for spectroscopic detection. An achromatic beam splitter 324 can be included to allow for simultaneous image and spectral acquisition. By insertion of lens 326, the back pupil plane (i.e., Fourier plane) of the objective can be imaged onto the camera, etc. 320, and the backscattering spectra can be imaged onto the entrance slit of the spectrograph coupled with camera, etc. 322 by additional insertion of lens 328, allowing for acquisition at camera, etc. 330. This setup can obtain backscattering spectra and image in the spatial Fourier-transform mode where each pixel can represent a known set of 3D wave-vectors (wavelength, angle, azimuth). With insertion of only lens 328, the conventional image can be received by camera, etc. 320 in parallel with Fourier-domain scattering spectra through camera, etc. 322.

Figure 4:
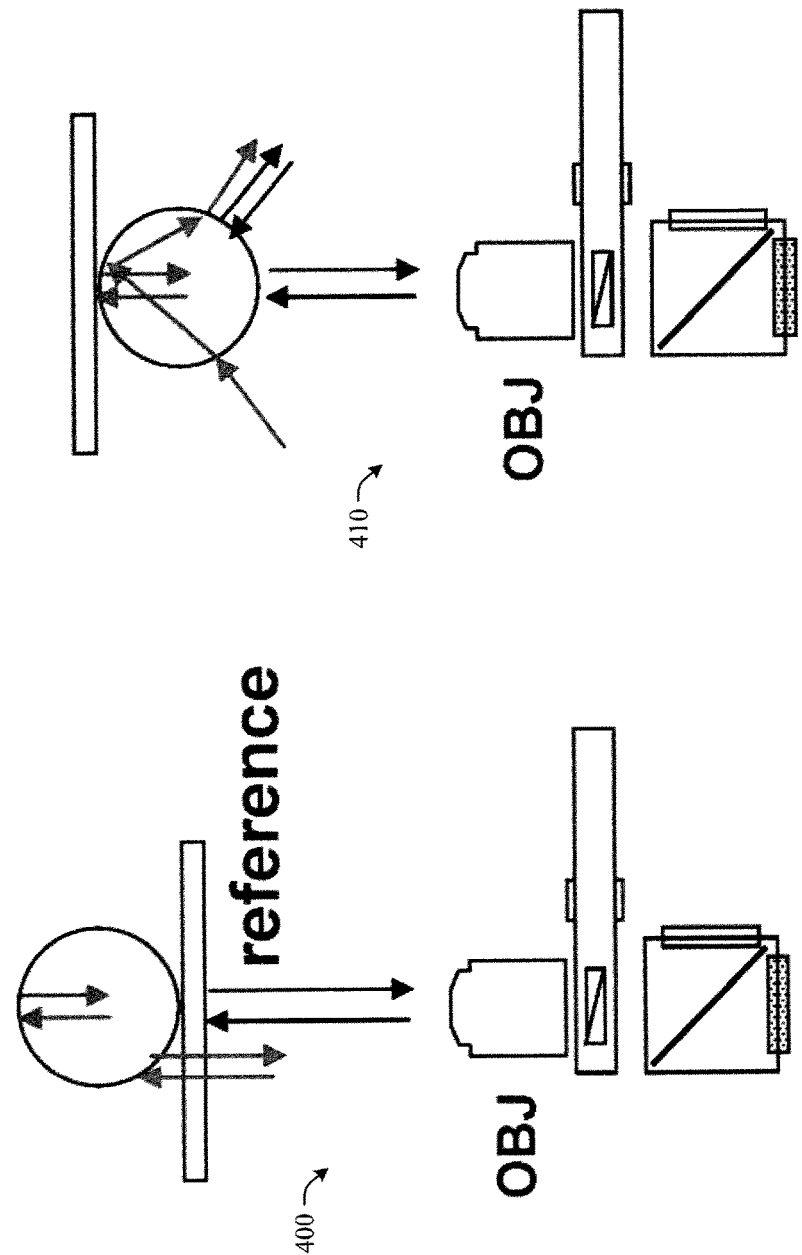
FIG. 4 illustrates two configurations for obtaining imaging data from a sample.

Several novel features are incorporated in an MD-ELSM system such as that shown in the setup of FIG. 3. For example, MD-ELSM can assess the multi-dimensional elastic light-scattering spectral signals that contain a full set of 3D wave-vectors (scattering intensity vs. wavelength, scattering angle, azimuth angle) in both transmitted and reflectance geometries with sub-cellular specificity. Additionally, MD-ELSM can incorporate aperture-plane variable mask to select the illumination angle (INA) and provide the best opportunity to identify the spectral features that carry the most information about variations in sub-cellular structure. FIG. 4 illustrates two configurations for obtaining imaging data from a sample. Without requiring any additional components in the system, MD-ELSM can be used as a unique low spatial-coherence and low temporal-coherence common-path interference microscopy by assuming the sample configuration at 400 and high INA. Alternatively, MD-ELSM can be used as a unique path-length spectroscopic system at sub-cellular level by assuming the sample configuration at 410 and low INA. Further, MD-ELSM has the capability to image the back pupil (Fourier plane) of the objective into the spectrographic imaging system to obtain spectra as a function of scattering wave vector, the scattering angles, wavelengths and azimuth angles, within the numerical aperture cone of the objective. Also, it can incorporate traditional Zernike phase contrast, Nomarski differential-interference contrast, and darkfield optical systems that also allow direct imaging and spectral analysis of single sub-cellular organelles in living and fixed cells. In addition, MD-ELSM can include integrated fluorescence microscopy for functional and molecular imaging and spectroscopic analysis. As another example, algorithms described herein can be used to characterize various physical properties and heterogeneity of refractive index variation.

Figure 5:
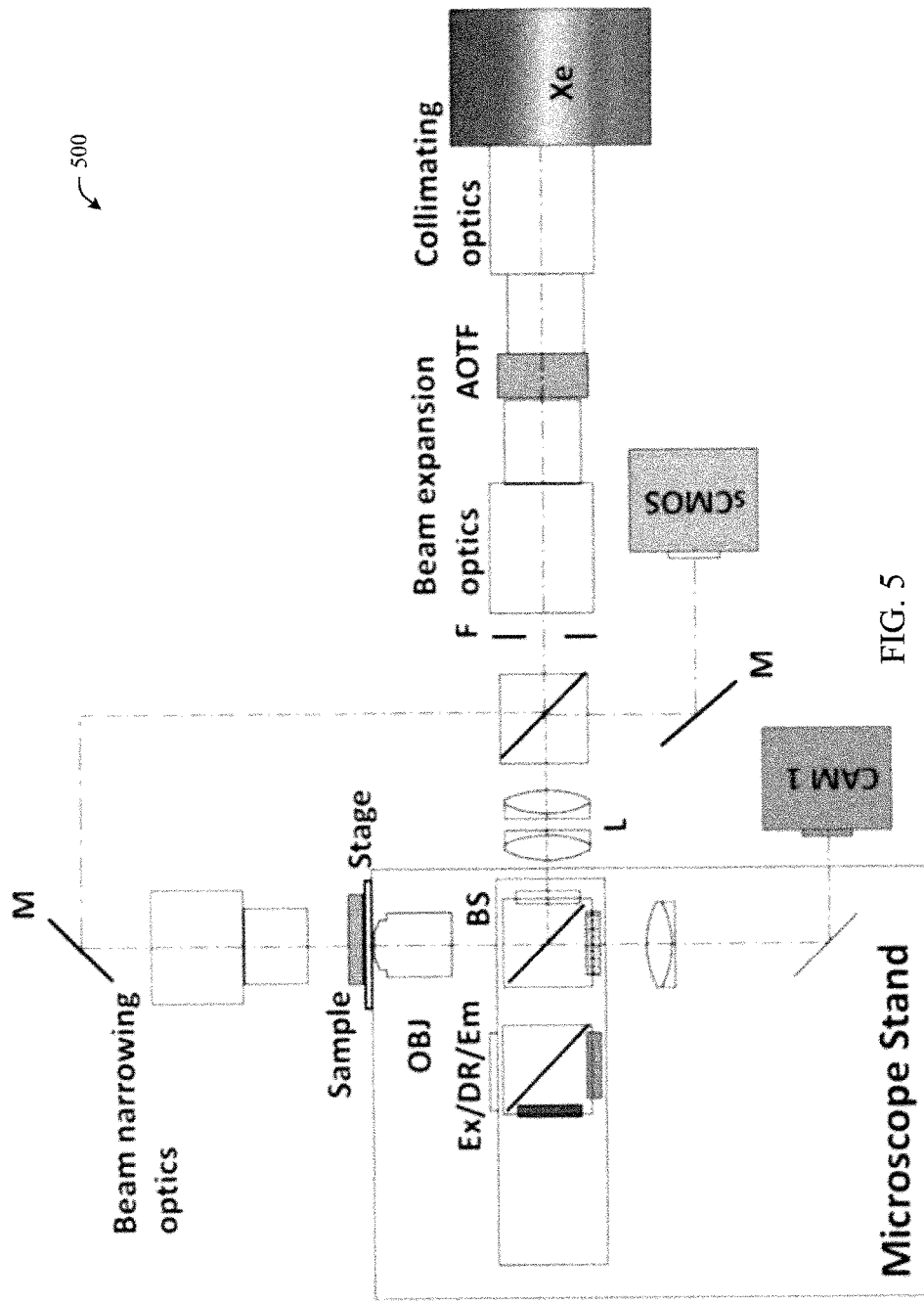
FIG. 5 illustrates an example alternative embodiment of a spatial-domain low-coherence quantitative phase microscopy (SL-QPM) system in accordance with aspects of the subject innovation.

FIG. 5 illustrates an example alternative embodiment of a spatial-domain low-coherence quantitative phase microscopy (SL-QPM) system 500 in accordance with aspects of the subject innovation. SL-QPM system 500 includes several differences when compared with system 300, some or all of which can be included in various embodiments. The example embodiment of SL-QPM system 500 can provide a larger field-of-view, a more uniform illumination and a faster data acquisition speed when compared with system 300. In contrast to system 300, system 500 can employ a Köhler illumination configuration to ensure a more uniform illumination. Additionally, system 500 can also employ an acousto-optical tunable filter (AOTF) device in the illumination path that can scan the wavelength in the visible range (450-700 nm) to replace the spectrograph of system 300 in the detection path, eliminating the need for mechanical moving component in the data acquisition process. Further, system 500 can employ a camera (e.g., a CCD camera, a scientific complementary metal-oxide-semiconductor (sC-MOS) camera, etc.) that has a large imaging size and high sensitivity to capture a larger field-of-view.

Figure 6:
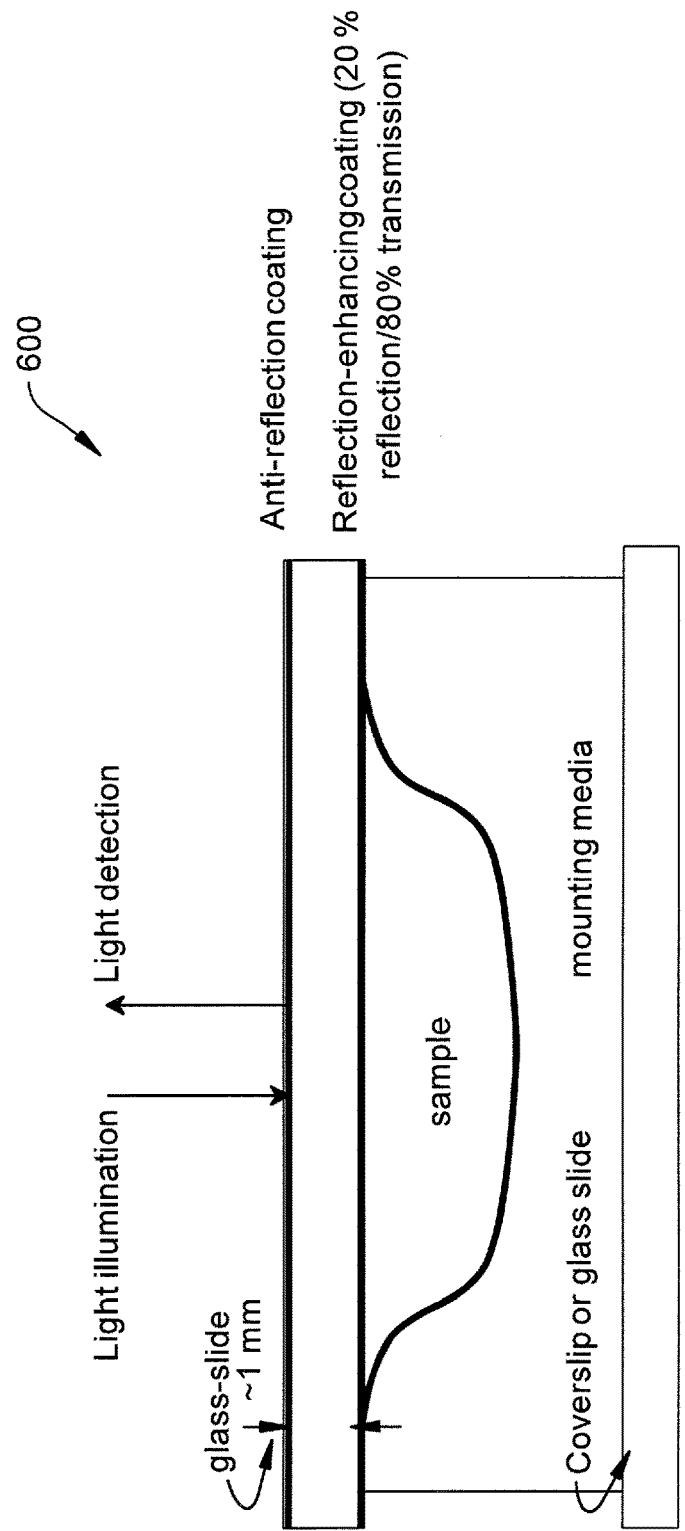
FIG. 6 illustrates a specially-prepared glass slide that can be used with systems and methods disclosed herein, in accordance with aspects of the subject innovation.

FIG. 6 illustrates a specially-prepared glass slide that can be used with systems and methods disclosed herein, in accordance with aspects of the subject innovation. In various aspects, the subject innovation can include slide preparation methods disclosed herein, as well as the ability of analyzing 3D nanoscale structural changes from unstained tissue or cell sections. In various aspects, systems and methods of the subject innovation can include a specially-prepared glass slide such as that illustrated in FIG. 6, in which one side can be coated with a reflection-enhancing coating material (e.g., 80% transmission/20% reflection, or other ratios wherein a majority of the light is transmitted) at the interface of the sample and glass slide, and the other side can be optionally coated with anti-reflection coating. The anti-reflection coating can remove unwanted reflection from the optical path, and the reflection-enhancing coating can generate a stable reference wave and enhance the signal-to-noise ratio for weakly scattered unstained samples.

The backscattered wave from the sample is superimposed with the reference wave reflected at the glass-sample interface, resulting in an interference signal expressed by equation 1, $$P(k) = S(k)\left[r_r^2 + \int_0^Z r_s^2(z')dz' + 2\int_0^Z r_s(z')r_r\cos(2kn(z')z')dz'\right] \quad (1)$$

where $S(k)$ is the power spectrum of the source, $r_r$ is the reflection coefficient of the reference wave, $r_s(z)$ is the scattering coefficient of the sample at depth z, Z is the total sample thickness and $n(z)$ is the refractive index distribution along the axial z-direction. The Fourier inverse of this interference signal results in equation 2, $$p(z_{opl})2\Gamma * \left[(R_r + R_s)\delta(0) + 2r_r\mathcal{F}^{-1}\left(\int_0^Z r_s(z')r_r\cos(2kn(z')z')dz'\right)\right] \quad (2)$$

(where $R_r = r_r^2$ and $R_s = \int_0^Z r_s^2(z')dz'$), which is a convolution of the source correlation function $\Gamma$ with the superposition of the reference wave and the backscattered sample wave. This mathematical relation suggests that the source correlation function serves as an implicit coherent window that separates the phase information at each optical depth whose resolution is limited by the coherence length, which is discussed in further detail below. The amplitude of the Fourier-transformed signal at any given optical depth of interest gives the optical path length (OPL) distribution along the axial direction of the sample, while the phase at each fixed optical depth of interest captures the sub-resolution nanoscale change in OPL at that location. This sub-resolution change in OPL is calculated as in equation 3, $$\delta p(z_{opl}) = \frac{\lambda_0}{2\pi}\arctan\left(\frac{\text{Im}(p(z_{opl}))}{\text{Re}(p(z_{opl}))}\right) \quad (3)$$

where $z_{opl}$ is the fixed optical depth location, Im and Re denote the imaginary and real parts of the complex convolution $p(z_{opl})$, respectively, and $\delta p(z_{opl})$ is the optical path length difference (OPD) at a specific optical depth location $z_{opl}$, which is not limited by the resolution of optical system and can be used to probe the nanoscale structural changes of the biological cell.

To access the 3D nanoscale structural changes, the implicit coherent gating inherent in the spectral interferometry can be used, as described below. According to equation 2, the Fourier transformation of the spectral interference signal is a convolution of the source correlation function $\Gamma$ (i.e., the power spectral density of the source) and the actual OPL profile of the scattering object. As an example, assume that the true OPL profile of the scattering object is the distinct stem-plot in FIG. 7A.

Due to the limited spectral bandwidth of the light source, the source correlation function, as indicated in FIG. 7A, can serve as a window for coherent gating to restrict the detected OPD to come from the back-scattered waves within this window around the given optical-depth of interest, without being affected by the scattered waves from those optical depths at one or more coherence-lengths apart. The derived OPL profile from the SL-QPM system is illustrated in FIG. 7B, where the original OPL profile from the scattering object is modified by the source correlation function. If multiple fixed optical depth locations are chosen such that the distance between them is at least one coherence length apart (indicated by the dots in FIG. 7A), the internal structural changes within the coherence-gated optical section around each optical depth can be captured. The physical conditions for this approach to be effective include a closely matched refractive index between the sample and mounting medium and that the signal strength at the selected locations should be above the noise floor.

The nanoscale nuclear architectural features associated with aspects of the present innovation can be used independently of or in conjunction with existing pathological diagnostic procedures or criteria. Because these systems and methods do not require any special sample preparation, they can be easily incorporated with existing diagnostics. Techniques described herein can enhance early detection of malignancy that would otherwise be missed by conventional cytopathology. As an additional application, these techniques can provide a new capability for elucidating the mechanism of malignancy and correlating functional and molecular parameters with malignancy-associated structural changes. Systems and methods of the subject innovation can thus facilitate the discovery of new therapeutic targets and provide novel approaches to monitoring the effects of treatment or preventive strategies. Systems and methods of the subject innovation can be applied in a variety of clinical settings, such as to identify the suspicious regions for cancer on slides; to improve the detection of cancer, even from normal-appearing cells; to perform the prediction of future cancer risk; etc.

Theory and Analytical Techniques

Cancer is typically diagnosed based on the microscopic examination of morphological changes in the cell and tissue stained with reagents such as hematoxylin and eosin with a conventional bright-field microscope, whose image contrast is obtained through the differences in the absorption cross section of various stains. Due to its diffraction-limited resolution (~500 nm), the observed characteristic cytologic alterations in malignant cells for cancer diagnosis are often limited to overall nuclear appearance, such as enlarged nuclear size, irregularity of nuclear contour, and increased nuclear density. However, these well-established cytologic characteristics in cancer cells may not be present or significant, especially when only a small amount of human cell or tissue samples are available for examination or in the early course of the tumor development, which may delay definitive diagnosis or lead to repeat procedures to obtain additional cell and tissue samples. In contrast, aspects of the subject innovation can provide for increased diagnostic sensitivity.

Thanks to the significant advancement in understanding the molecular changes of cancer cells, it is well recognized that tumorigenesis is the result of cumulative effect of multistep genetic and epigenetic alterations. Numerous proteins, RNAs, and genetic markers that are involved in the carcinogenesis of malignant neoplasm have been identified. Those cells from cancer patients, even though classified as "indeterminate" or "normal" by pathologists, may still undergo a series of malignancy-associated genetic or molecular alterations. As a result, subtle structural abnormalities may occur, especially in the cell nucleus. For those structural changes at the scale of less than the resolution of conventional optical microscopy (<~500 nm), they may not be easily detectable by conventional pathology. However, microscopy techniques associated with the subject innovation can detect subtle previously pathologically undetectable cellular alterations in situ, and can be used to improve the ability to accurately diagnose cancer. In aspects, the innovation includes methods utilizing these techniques for early detection of cancer.

Figure 8A:
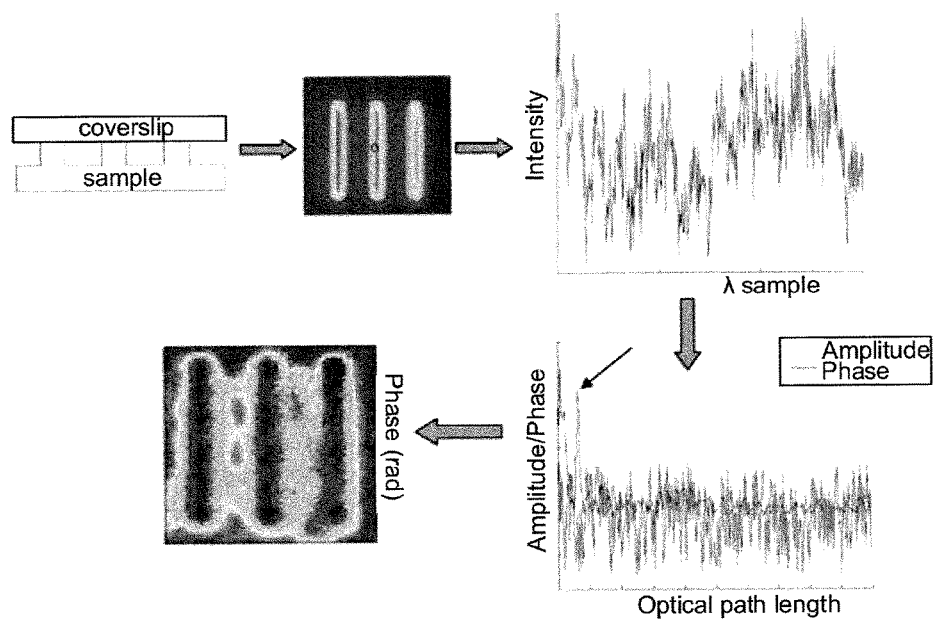
FIG. 8A illustrates example processing steps associated with SL-QPM.
Figure 8B:
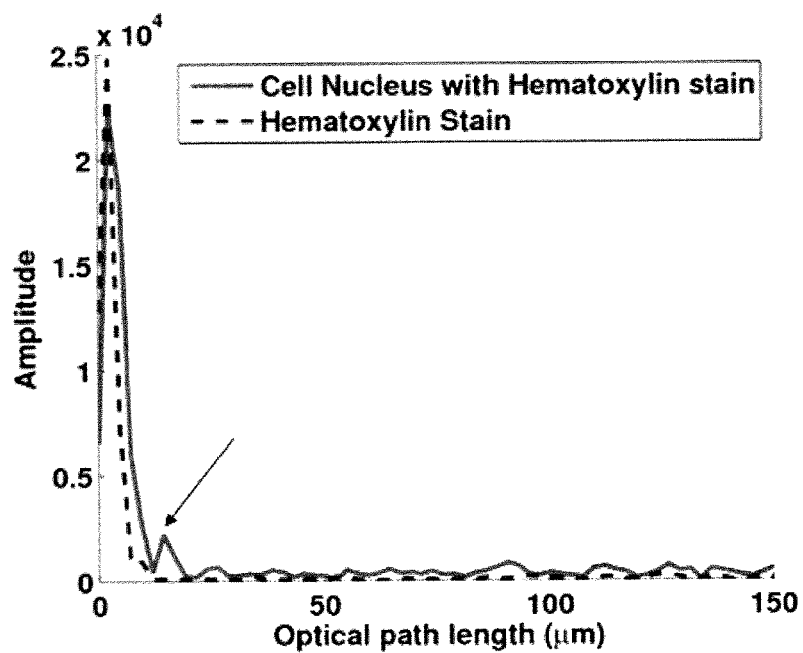
FIG. 8B illustrates that selected optical path lengths of interest were not affected by the absorption of the cytology stains.

Systems and methods associated with the subject innovation can record a microscopic image with a reflectance intensity cube $I(\lambda; x, y)$ where $\lambda$ is the wavelength and $(x, y)$ represents the pixel position of the image. The phase value at every pixel can be obtained by Fourier analysis of $I(\lambda; x, y)$ and is converted to the corresponding optical path length $(OPL(x, y) = \langle n(x,y) \rangle L(x, y)$ where $\langle n(x,y) \rangle$ is the average refractive index along the axial direction (i.e., z-direction) at the specific pixel $(x, y)$, and $L(x, y)$ is the physical thickness). The sensitivity of $OPL(x, y)$ was determined to be 0.9 nm in air. As a result, a two-dimensional, nanoscale spatial distribution of optical path length (OPL map) can be obtained, as shown in FIG. 8A, which illustrates processing steps that can be SL-QPM system. As shown, the spectrum from each pixel can be interpolated (e.g., with a bandwidth from approximately 500 nm or less to approximately 620 nm or more), and can be windowed prior to performing fast Fourier transform. A certain fixed depth of interest can be chosen for phase processing. The two-dimensional quantitative phase map can be obtained by repeating these steps pixel-by-pixel.

The optical path length at each pixel is mathematically the product of refractive index and physical thickness $(OPL(x, y) = \langle n(x,y) \rangle L(x,y))$. Due to standardized clinical specimen preparation, most cytology slides have a single cell layer for the same organ with consistent physical thickness, which in the experiments discussed herein was confirmed by confocal microscopy measurement. Assuming the same physical thickness, alterations in optical path length at each pixel $OPL(x, y)$ are essentially derived from the changes in the refractive index, proportional to the macromolecular concentration or nuclear density for the cell nucleus. Therefore, the changes of the nuclear architecture in cancer cells describe the alterations in the spatial variation of nuclear density.

The phase stability of the SL-QPM can be characterized by measuring the phase of a known sample (e.g., a US Air Force Target), and the measured sensitivity was 0.9 nm, as obtained in a histogram of measured phase performed for ~3 minutes. The final optical path length for each pixel can be calculated by adding the optical depth of interest to its shifted (due to phase variation) path length.

The SL-QPM essentially records a microscopic image with a reflectance interferometric intensity cube $I(x, y, k)$. The phase value at every pixel can be obtained by Fourier analysis of $I(x, y, k)$ and is converted to the corresponding OPL $(OPL(x, y) = \langle n(x,y) \rangle L(x,y)$, where $\langle n(x,y) \rangle$ is the average refractive index along the axial direction (i.e., the z direction) at the specific pixel $(x, y)$, and $L(x, y)$ is the physical thickness). As a result, a 2-D, nanoscale spatial distribution of the OPL can be obtained (e.g., as an OPL map, etc.). To quantify the image characteristics of the OPL map in the nucleus, three statistical parameters were extracted in experimental analysis discussed herein (although additional or alternative parameters could also be extracted): average OPL $\langle OPL \rangle$ over the 2-D spatial distribution of $OPL(x, y)$; standard deviation $\sigma_{OPL}$ over $OPL(x, y)$, representing a global variation; and entropy $E_{OPL}$, which is a measure of randomness, representing a more localized heterogeneity derived from texture analysis. Both $\sigma_{OPL}$ and $E_{OPL}$ quantify the architectural heterogeneity.

Based on the spatial distribution of optical path length from a single nucleus, a texture analysis can be performed, and statistical parameters can be quantified. Three such parameters are discussed, although other statistical parameters can be derived in light of the innovation disclosed herein. The average optical path length $\langle OPL \rangle$ and standard deviation $\sigma_{OPL}$ can be calculated by taking the mean and standard deviation of all OPL values from a single nucleus. The entropy $E_{OPL}$, a parameter describing the randomness, is defined as $E_{OPL} = -\Sigma_{i=0}^{N-1} (I_i) \log_2 p(I_i)$, where $I_i$ is a random variable indicating intensity, $p(I_i)$ is the histogram of the intensity levels in a region, and N is the number of possible intensity levels. The intra-nuclear $\langle OPL \rangle$ describes the average optical path length or average density with a single nucleus (with the same nuclear thickness). The intra-nuclear standard deviation $\sigma_{OPL}$ and intra-nuclear entropy $E_{OPL}$ describe the global and local heterogeneity of optical path length or nuclear density distribution, respectively.

In aspects, intra-nuclear architectural heterogeneity parameters discussed further herein—for example, $\sigma_{OPL}$ and $E_{OPL}$—can be used to distinguish malignant cells from benign cells in various tumor types and show a high level of statistical significance to detect subtle changes of malignancy from cytopathologically indeterminate cells. The global nuclear heterogeneity as expressed by $\sigma_{OPL}$ within a single nucleus is a robust and universal parameter in detecting subtle changes of cell proliferation in cancer cell lines and identifying malignancy in the two human gastrointestinal tumor types with the highest level of statistical significance. The entropy $E_{OPL}$ describing the local heterogeneity of the nuclear architecture is the second most effective parameter and shows strong statistical significance in cell lines and cancers, for example, colorectal and pancreatic cancers. In many instances, the cells from cancer patients also exhibit a higher level of inter-nuclear heterogeneity, evidenced by the wider spread of $\sigma_{OPL}$ and $E_{OPL}$ in cell nuclei from colorectal and pancreatic cancer patients. The optical path length averaged over single nucleus $\langle OPL \rangle$ also indicates certain capability of discriminating two extreme groups of frankly benign and malignant cells, in agreement with cytopathological diagnosis in colorectal and pancreatic cancers, but in some situations can be a less significant parameter for detecting cytologically indeterminate malignancy.

In aspects, the subject innovation can include various statistical methods for evaluating optical parameters of a sample (e.g., cells or organelles such as cell nucleus, etc.). One approach can be based on the statistical analysis of Fourier-transformed amplitude of low spatiotemporal-coherence backscattering interferometric signals from an instrument that simultaneously obtains a speckle-free backscattering microscopic image in which the individual pixel contains the backscattering spectrum, such as those of other aspects of the subject innovation. A theoretical model of a biological cell whose refractive index profile is represented by one-dimensional Gaussian random field model can be constructed. Then numerical analysis techniques can be presented based on simulated one-dimensional interferometric signals from a series model of biological cells with various known statistical properties of refractive index. The potential of these techniques in cancer detection is demonstrated with experimental results discussed herein. These results show that the statistical properties of cell nuclear structure used were able to detect the subtle changes that are otherwise undetectable by conventional cytopathology.

Figure 9:
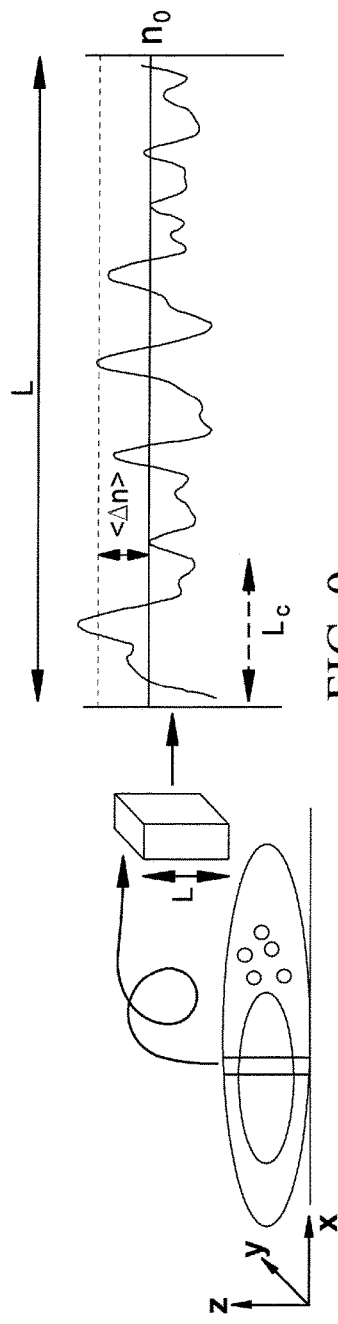
FIG. 9 illustrates an example illustrative refractive index profile of internal structures of a biological cell.

If the three-dimensional refractive index distribution of a biological cell is described as n(x, y, z), the spatial profile of refractive index of cell internal structures at a given pixel (x, y) within a single biological cell or a sub-cellular component can be described as a sum of the average axial refractive index $n_0$ and a spatially-varying component n(z): $n_0(z)$=n+Δn(z), as shown in FIG. 9, which illustrates an example refractive index profile of internal structures of a biological cell. The thickness of the cell at a given pixel is L(x, y). The average axial refractive index $n_0$ of the single cell can be determined by Fourier transformation of backscattered interferometric signals.

To characterize the complex, inhomogeneous spatially-varying component of refractive index distribution of cell internal structures within a single biological cell, a stochastic model can be adopted, such as a one-dimensional Gaussian random field (GRF) model (e.g., in the analysis discussed herein, this was performed via the statistical software package R-project). The longitudinal refractive index can be considered at a given pixel (x, y) within a single biological cell (n(z)) as a one-dimensional stochastic process having a Gaussian probability density function. Each value of n(z) can be a Gaussian random variable with the mean $n_0 = \langle n(z) \rangle$ and its standard deviation (i.e., the average magnitude of refractive index variation) $\langle \Delta n \rangle = \sqrt{\langle [n(z)-n_0]^2 \rangle}$. The two-point correlation function $C_n(z)$ can be defined by equation 6:

$$C_n(z) = \langle [n(z=0)-n_0][n(z)-n_0] \rangle \quad (6)$$

Figure 10:
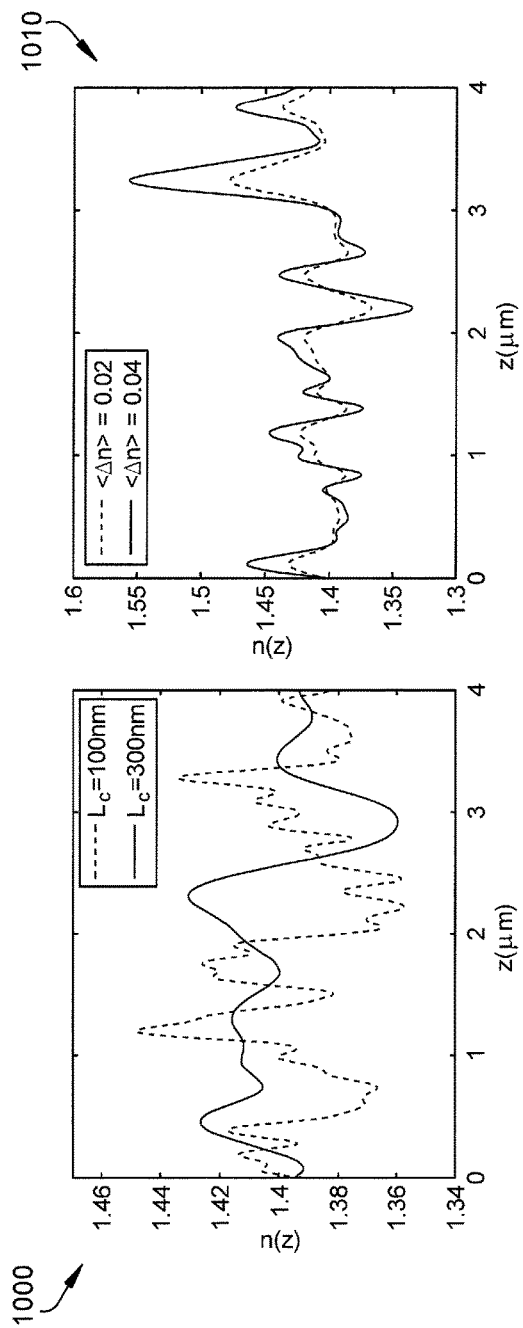
FIG. 10 shows representative refractive index profiles modeled with a Gaussian random field.

The Gaussian function can be used as the correlation model: $C_n(z)=\exp(-z^2/(L_c/2)^2)$, where $L_c$ is the spatial correlation length of refractive index representing the length scale over which the spatial correlation decreases to a negligible level. Therefore, a larger $n_0$ can represent the denser internal structural components of a biological cell, higher $\langle \Delta n \rangle$ is associated with the increased spatial variation of the density of intracellular material in the axial direction of the three-dimensional cell and a longer $L_c$ can correspond to a slowly-changing axial refractive index profile due to the presence of large macromolecules. FIG. 10 shows the representative refractive index profiles modeled with GRF with a fixed $n_0$=1.4, and various correlation length $L_c$ and the standard deviation of refractive index $\langle \Delta n \rangle$. The representative refractive index profiles n(z) modeled with GRF are shown at 1000 with fixed $n_0$=1.4 and $\langle \Delta n \rangle$=0.02, but different correlation length $L_c$, and at 1010 with fixed $n_0$=1.4 and $L_c$=140 nm and different average magnitude of refractive index variation $\langle \Delta n \rangle$.

Assuming that there are some number (e.g., 5000) of pixels inside the cell which have common statistical properties of refractive index (e.g., $n_0$ and $\langle \Delta n \rangle$), the GRF model can generate a refractive index profile for each pixel. To emulate the configuration of the cytology specimens in the experiment, a glass slide (refractive index n=1.52) was added as the top and bottom medium that sandwich the cell.

For each GRF-modeled axial refractive index profile, a one-dimensional multilayer dielectric slab model that implements Fresnel reflection was used to generate its backscattering spectrum. The backscattering spectrum from each pixel was numerically resampled to evenly spaced wavenumbers and multiplied by a Hanning window before applying a fast Fourier transform. The Fourier transformed data at the prominent peak corresponding to the optical path length of interest depth z were selected for amplitude processing. After taking the discrete Fourier transform, a complex-valued F can be obtained, and the amplitude can be extracted by taking the absolute value of F(z) as shown in equation 7:

$$A(z)|_{(x,y)} = |F(z)|_{(x,y)} \quad (7)$$

The amplitude map was obtained by plotting the amplitude value at a certain depth plane for each pixel (e.g., 5000 pixels in total). Based on the amplitude maps, statistical parameters can be determined. Three statistical parameters were quantified in the discussion that follows (although others could be used): the average amplitude $\langle A \rangle$ over the two-dimensional spatial distribution of A(x, y); the standard deviation of the amplitude $\sigma_A$, and the ratio of $\sigma_A$ to $\langle A \rangle$, referred to as fluctuation ratio $R = \sigma_A / \langle A \rangle$.

Using systems or methods of the subject innovation, a signal can be obtained. The detected signal as a function of wavenumber can be represented by equation 8:

$$I(k)|_{(x,y)} = S(k)\{R_r + R_s + 2\sqrt{R_r R_s}\cos(2k(p_0 + \Delta_p))\}|_{(x,y)} \quad (8)$$

where S(k) is the source power spectral density, $R_r$ and $R_s$ represent the reference reflectivity and sample reflectivity respectively, $p_0$ corresponds to the optical path length of interest and Δp is the optical path length difference between the reference and sample beams. The first two terms in equation 8 represent the DC terms, while the third term represents those related to the interference.

To account for the effect of variation in the stain-induced nuclear refractive index, a refractive index correction model can be used: $n_c(x,y) = n(x,y) - \Delta n_c$, where $n_c$ is the corrected refractive index, n is the measured refracted index before the correction, and $\Delta n_c$ is the refractive index correction factor accounting for the addition of staining agent. For a given clinical histology sample, the correction factor $\Delta n_c$ can be calculated through the equation: $\Delta n_c = \beta \alpha$, where α is the absorption coefficient of the sample, and β is the modified specific refraction increment, which is a constant factor. This correction model follows directly from the linear relation between refractive index and change in cell dry mass concentration. The absorption coefficient α of each sample can be derived from the image obtained in the transmission mode based on Beer-Lambert's law ($T=10^{-\alpha L}$, where L is sample thickness). The modified specific refraction increment β can be computed from the calibration sample set consisting of a series of standard calibration histology slides prepared with different amounts of H&E stain. The corrected nuclear refractive index map $n_c(x, y)$ can be used in the analysis of samples in accordance with aspects of the innovation.

Experimental Results

To aid in the understanding of aspects of the subject innovation, experimental results associated with specific experiments that were conducted are discussed herein. However, although for the purposes of obtaining the results discussed herein, specific choices were made as to the selection of various aspects of the experiments and associated setups—such as the disease being studied (e.g., cancer, as opposed to non-cancerous conditions; specific types of cancer; etc.), choice of specific statistical parameters, setup of optical apparatuses, etc.—the systems and methods described herein can be employed in other contexts, as well.

In connection with the experiments discussed herein, those involving human specimens were performed and all specimens were collected with the approval of the Institutional Review Boards at University of Pittsburgh and University of Washington. All animal studies were performed in accordance with the institutional Animal Care and Use Committee of University of Pittsburgh. All mice were housed in microisolator cages in a room illuminated from 7:00 AM to 7:00 PM (12:12 hour light-dark cycle), with access to water and ad libitum.

The cells on cytology slides from human patients were typically fixed with air-drying method; prepared by cell smearing on a glass slide; and stained by Diff-Quik (DQ) stains or Papanicolaou-stained and coverslipped. Such methods typically minimize the single-cell thickness variations among different patients for the same type of cell in the same organ.

The cells analyzed from histology slides were prepared with standard clinical protocol: formalin fixed, paraffin embedded and stained with hematoxylin and eosin, and coverslipped.

The statistical analyses discussed herein were performed based on the Student's t-test. Two-tailed P-values were used for all analyses. The alpha level was assumed to be 0.05. The two-tailed P-values of less than 0.05 were considered as statistical significance.

Preliminary Results

Figure 11:
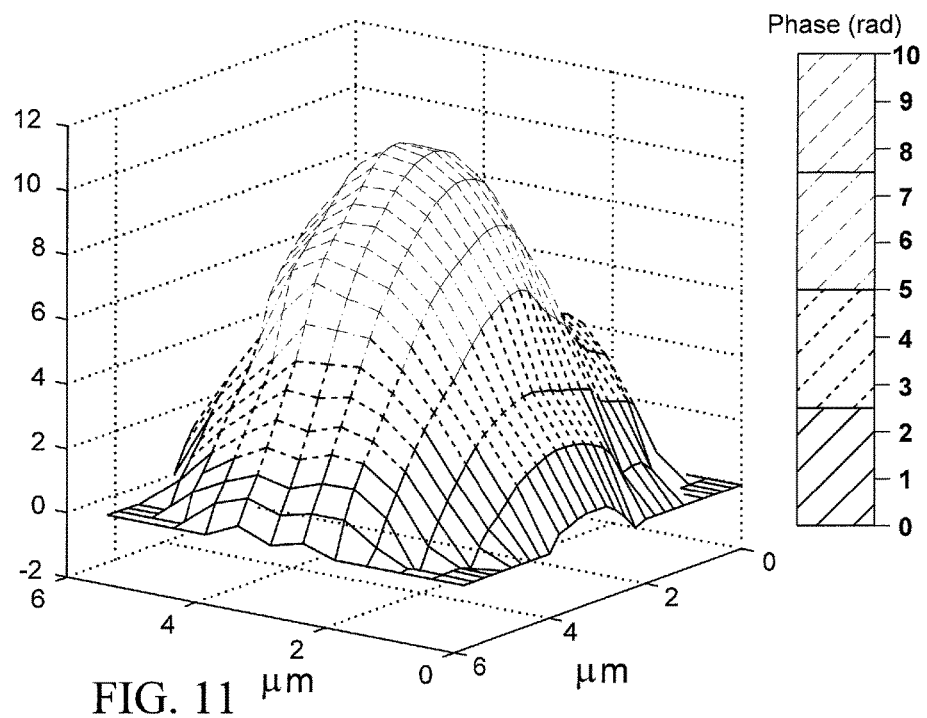
FIG. 11 illustrates the phase map of a polystyrene microsphere.

In one experiment, measurements of polystyrene beads were carried out. The sample consisted of a glass coverslip (thickness, d~170 μm) with polystyrene beads that had been dried from suspension onto the back surface. The phasemap of the microsphere is shown in FIG. 11. The colorbar represents the phase in radian. The diameter of the single microsphere was experimentally determined to be 4.92 μm (with the microsphere refractive index n=1.59), which was close to the manufacturer's specification of the mean diameter of 5.003±0.04 μm.

Figure 12:
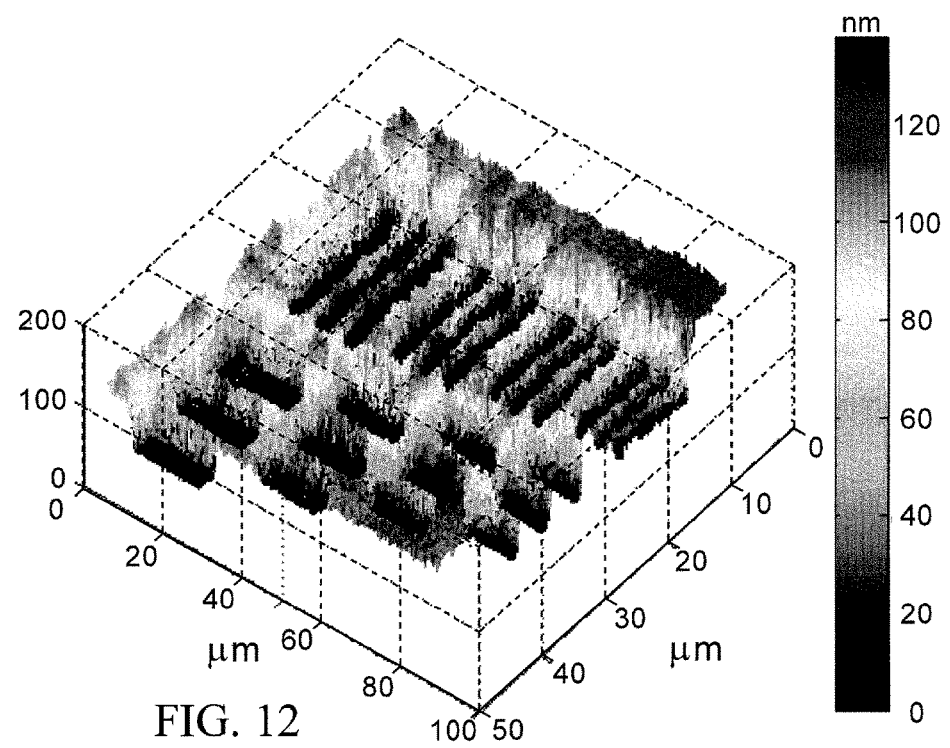
FIG. 12 shows the depth profile of a U.S. Air Force target as obtained via SL-QPM.

In another experiment, discussed in part above, the depth profile of a U.S. Air Force target was obtained via SL-QPM, as shown in FIG. 12. Lateral resolution was demonstrated by the resolving the smallest bar (spatial period of 4.4 μm). The color bar units are nanometers.

Additionally, to analyze how amplitude parameters are affected by the statistical properties of inhomogeneous refractive index distribution of cell internal structures, an experiment was performed involving numerical simulation with a series of biological cell models whose refractive index profile n(z) was modeled by one-dimensional Gaussian random field (GRF), which was described by three physical quantities: the average axial refractive index $n_0$, the standard deviation of axial refractive index (i.e., the average magnitude of refractive index variation) $\langle \Delta n \rangle$ and the spatial correlation length of refractive index $L_c$, as defined above. Additionally, due to the intrinsic variations of cell thickness L, it was considered as another important variable in the numerical model. All values of these physical parameters were chosen to be within the cytologically relevant range, which was determined from experimental data of cytological specimens from animal models and human patients.

Figure 13:
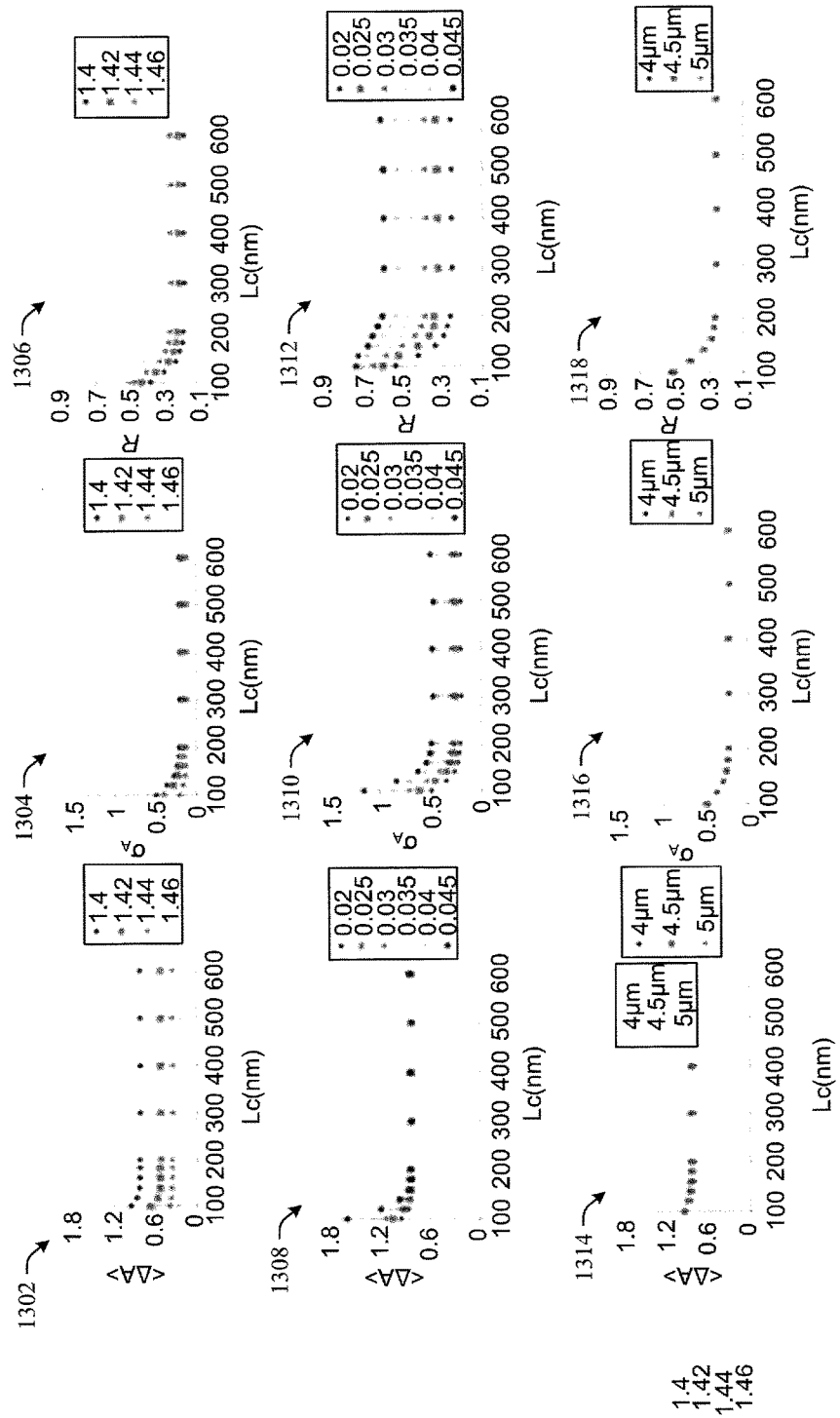
FIG. 13 illustrates the dependence of statistical amplitude parameters on the average refractive index, standard deviation of refractive index and thickness.

Based on the Fourier analysis of one-dimensional interferometric signals, three simple amplitude parameters were derived from techniques described herein, including the average amplitude $\langle A \rangle$, the standard deviation of the amplitude $\sigma_A$, and the fluctuation ratio R ($R = \sigma_A/\langle A \rangle$). FIG. 13 demonstrate the dependence of these three parameters on the statistical properties of refractive index including average axial refractive index $n_0$, the average magnitude of axial refractive index variation $\langle \Delta n \rangle$ and the cell thickness L with different spatial correlation length $L_c$ of the refractive index. Assuming the biological cell had a weakly varying refractive index system, $L_c$ was chosen from a range of 100 nm to 600 nm. The top row of FIGS. 13 (1302, 1304, and 1306) shows the effect of $n_0$ on these three amplitude parameters with fixed $\langle \Delta n \rangle = 0.02$ and thickness L=4 μm. It was evident that with increased $n_0$, $\langle A \rangle$ shows a significant decrease. On the other hand, $\sigma_A$ was slightly decreased and R was moderately increased with the increase of $n_0$. The middle row of FIGS. 10 (1308, 1310, and 1312) shows the dependence of the three SL-QPM-derived parameters on $\langle \Delta n \rangle$ with fixed $n_0 = 1.4$ and thickness L=4 μm. Increasing $\langle \Delta n \rangle$ led to a significant increase in both $\sigma_A$ and R, but it only weakly increased $\langle A \rangle$. The bottom row of FIGS. 10 (1314, 1316, and 1318) revealed the contribution of cell thickness L to the three SL-QPM-derived parameters with fixed $n_0 = 1.4$ and $\langle \Delta n \rangle = 0.02$. Apparently, the variation of cell thickness in the biologically relevant range had very little effect on any of the three parameters.

The results from the numerical simulation showed that although the correlation between amplitude parameters and cell refractive index properties is rather complex, each of the amplitude parameter had a dominating contributor under the configuration emulating the cytology specimens. The average amplitude $\langle A \rangle$ was predominantly affected by the average axial refractive index $n_0$, and increasing $n_0$ will decrease $\langle A \rangle$. The standard deviation of the amplitude $\sigma_A$ was most affected by the average magnitude of axial refractive index variation $\langle \Delta n \rangle$, and increasing $\langle \Delta n \rangle$ will increase $\sigma_A$. The alterations in fluctuation ratio R mainly arose from the changes in $\langle \Delta n \rangle$, with a minor contribution from $n_0$, and was associated with the changes of $\langle \Delta n \rangle / n_0$. All three amplitude parameters were not affected by the correlation length of refractive index $L_c$ when $L_c$ was larger than 200 nm. The fact that the small changes in cell thickness did not alter the amplitude parameters was beneficial for many biomedical applications due to the intrinsic variation of cell thickness.

Animal Models

In one experiment, cytologically normal-appearing intestinal epithelial cells from an animal model from intestinal carcinogenesis—the APC$^{Min}$ mouse model—it was shown that despite their indistinct cytological features, the changes in in situ nanoscale nuclear architectural heterogeneity can be detected using SL-QPM in small intestinal epithelial cells from the 4 to 5-month-old APC$^{Min}$ mice with tumors, compared with the wild-type mice.

Epithelial cells were obtained from visually normal mucosa of the small intestine with a cytology brush. The cytology brush was immersed into the Cytolyt solution (e.g., from Cytec Corporation, Boxborough, Mass.). The slides were prepared by a standard thin prep processor (e.g., from Cytec Corporation). Cells were then stained with Papanicolaou stains and sealed with a mounting medium and coverslip.

Three C57BL APC wild-type mice and three age-matched C57BL APC$^{Min}$ mice at 4 to 5 months old were sacrificed. The small intestines were removed, longitudinally opened, and washed with phosphate-buffered saline (PBS). Cells were examined by an expert cytopathologist and non-cancerous-looking cells were analyzed by SL-QPM. For each mouse, about 20 to 30 cells are randomly selected for SL-QPM analysis.

To explore the ability of nanoscale nuclear architectural characteristics quantified by SL-QPM to identify cancer from cytologically indeterminate cells, some experiments used a well-established animal model of colorectal carcinogenesis—the APC$^{Min}$ mouse model. It is a genetically modified animal model that represents the human condition of familial adenomatous polyposis syndrome in which the adenomatous polyposis coli (APC) gene undergoes a germline mutation leading to a truncation in the APC protein and spontaneous development of intestinal adenomas. One experiment analyzed the cytopathologically indistinguishable intestinal epithelial cells from three age-matched wild-type mice and three APC$^{Min}$ mice at 4 to 5 months with the presence of tumors in the small intestine. FIGS. 14A and 14B show Papanicolaou-stained cytological images (in FIG. 14A) of representative intestinal epithelial cells from the APC$^{Min}$ mice compared to those of the wild-type mice obtained from a bright-field microscope and their corresponding OPL maps (in FIG. 14B) from the cell nuclei. The colorbar shows the magnitude of the OPL in the cell nucleus in micrometers. Although the microscopic cytological images looked similar (as confirmed by an expert cytopathologist), the OPL images that characterize the intranuclear distribution of OPL exhibit distinct differences. Based on these OPL maps, three statistical parameters from the nuclei were calculated: the average OPL $\langle OPL \rangle$ over the 2-D spatial distribution of OPL(x,y); the standard deviation of the OPL $\sigma_{OPL}$ representing a global variation and the entropy $E_{OPL}$—a measure of randomness, representing a more localized heterogeneity. As shown in FIG. 14C, the nuclear heterogeneity quantified by $\sigma_{OPL}$ and $E_{OPL}$ were significantly increased in approximately 20 to 30 randomly selected intestinal epithelial cells from the APC$^{Min}$ mice compared to those from the wild-type mice (p value<0.001). The error bar represents the standard error. However, no statistical difference was found in the average OPL $\langle OPL \rangle$ (p value=0.4). These results suggest that the higher nuclear architectural heterogeneity derived from its in situ nanoscale OPL map was associated with carcinogenesis, underlying the potential of this technique in accurate cancer diagnosis at the level of single cell nucleus.

For comparison with the techniques of the subject innovation, similar texture analysis was performed on conventional bright-field cytology images and it was found that the heterogeneity parameters (i.e., standard deviation σ and entropy E) cannot distinguish cytologically normal-appearing epithelial cell nuclei from the wild-type and APC$^{Min}$ mice (P value=0.30 and 0.29, respectively), underlining the importance of the nanoscale OPL map. Multiple factors showed support for the relevance of increased nuclear architectural heterogeneity parameters to the development of carcinogenesis or malignancy. First, the increased nuclear heterogeneity parameters ($\sigma_{OPL}$ and $E_{OPL}$) were consistently presented in both animal model and human cytology specimens. Second, the progressive increase of these parameters in benign cells, indeterminate cells from cancer patients and frankly malignant cells implies the capability of SL-QPM of detecting the subtle cytologically undetectable "transitional" alterations in cell nuclei in cancer patients. Third, the nuclear heterogeneity parameters from cytologically indeterminate or normal cells from cancer subjects resemble those from frankly malignant cells, distinct from normal cells from their benign counterparts, indicating that these cytological indeterminate cells from cancer subjects may share common biological events with the frankly malignant cells.

Figure 15A:
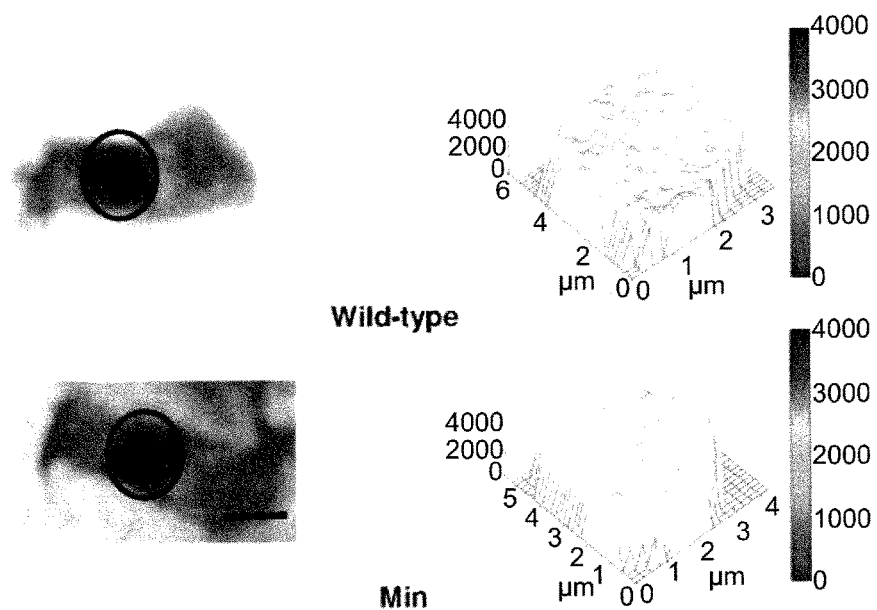
FIG. 15A illustrates representative cytological images and the corresponding amplitude maps of cell nuclei of intestinal epithelial cells from the wild-type and the Min mice.

Additionally, experiments were conducted to determine statistical parameters based on amplitude. FIG. 15A shows their representative Papanicolaou-stained cytological images obtained from a conventional bright-field microscope and the corresponding amplitude maps from the cell nuclei of histologically normal-appearing intestinal epithelial cells from Min mice and those from wild-type mice (control group). Scale bars in the image indicate 5 µm. Although the microscopic cytological images look similar (as confirmed by an expert cytopathologist), the amplitude maps that characterize the refractive index variation of cell internal structures exhibit distinct differences. The three statistical parameters from the cell nuclei were calculated from the amplitude maps: the average amplitude $\langle A \rangle$; the standard deviation of the amplitude $\sigma_A$ over the entire nucleus, and the fluctuation ratio R.

Figure 15B:
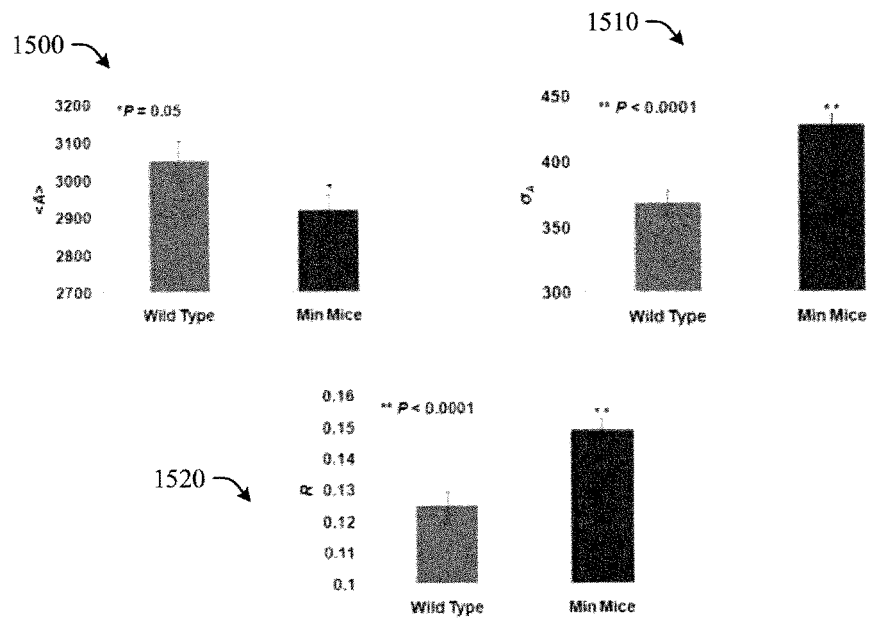
FIG. 15B shows statistical analysis of amplitude parameters in cytologically normal-appearing cell nuclei from wild-type and Min mice.

FIG. 15B shows the statistical analysis of these three SL-QPM-derived amplitude parameters from all epithelial cell nuclei in six mice (approximately 20-30 cells from each mouse and three mice in each group). The error bar represents the standard errors. As seen in graph 1500, $\langle A \rangle$ was significantly decreased in the cell nuclei of Min mice compared with those from wild-type mice (P=0.05) as shown in the left graph, indicating that the average axial refractive index of cell nuclei from Min mice is higher compared to those from the wild-type mice. Graph 1510 shows that $\sigma_A$ is significantly increased from the cell nuclei of Min mice compared to those of wild-type mice with high statistical significance (P<0.0001), revealing a higher axial refractive index fluctuation $\langle \Delta n \rangle$ in the cell nuclei from Min mice. Similarly, 1520 shows that R was also substantially increased in the epithelial cell nuclei of Min mice (P<0.0001), which reveals the higher ratio of axial refractive index fluctuation to the average axial refractive index ($\langle \Delta n \rangle / n_0$). The value R fell within the range from 0.1 to 0.2. Based on the lookup table created by the numerical simulation with a wide range of biologically relevant statistical properties of refractive index ($n_0$, $\langle \Delta n \rangle$, $L_c$ and L), the correlation length $L_c$ was estimated to be larger than 100 nm.

In order to demonstrate the ability of SL-QPM-derived amplitude parameters for sensitive detection of carcinogenesis, a well-established animal model of intestinal carcinogenesis—Min mouse model was studied. The intestinal epithelial cells that appeared normal to the cytopathologist were analyzed with conventional microscopy. The results showed that the normal-appearing cells from Min mice resulted in a decreased $\langle A \rangle$ and increased $\sigma_A$, when compared with those from wild-type mice. This result suggests that intestinal carcinogenesis is associated with increasing average refractive index and refractive index fluctuations in the cell nuclei. A higher average axial refractive index $n_0$ may indicate the higher density of nuclear components (e.g., chromatin), and a higher axial refractive index fluctuation $\langle \Delta n \rangle$ can be associated with increased spatial variation of the concentration of intra-nuclear solids (e.g., DNA, RNA, protein). Notably, the fact that the standard deviation of the amplitude $\sigma_A$ (p-value<0.0001) had a much smaller p-value than the average amplitude $\langle A \rangle$ (p-value=0.05) implies that the refractive index variation may be more sensitive than the average refractive index in detecting the carcinogenesis-associated structural changes. It is worth pointing out that both $\langle A \rangle$ and $\sigma_A$ could be affected by the absorption of the stains that are commonly used in the biological cell, especially for the clinical specimens, as discussed further herein. Due to the well-controlled standardized automated staining protocol, the systemic variation of staining is small. The fluctuation ratio R of axial refractive index can be used as a more experimentally robust parameter to minimize the effect of stain absorption. Such quantitative statistical information about the subtle alterations in nuclear architecture is otherwise undetectable with conventional optical microscopy, and requires systems and methods of the subject innovation. To confirm that these cells were truly indistinguishable with conventional microscopy, quantitative analysis was performed on conventional bright-field cytology images and it was found that the intensity parameters (i.e., average intensity and standard deviation of intensity) cannot distinguish cytologically normal-appearing epithelial cell nuclei from the wild-type and Min mice (p-value=0.10 and 0.26, respectively).

Figure 16:
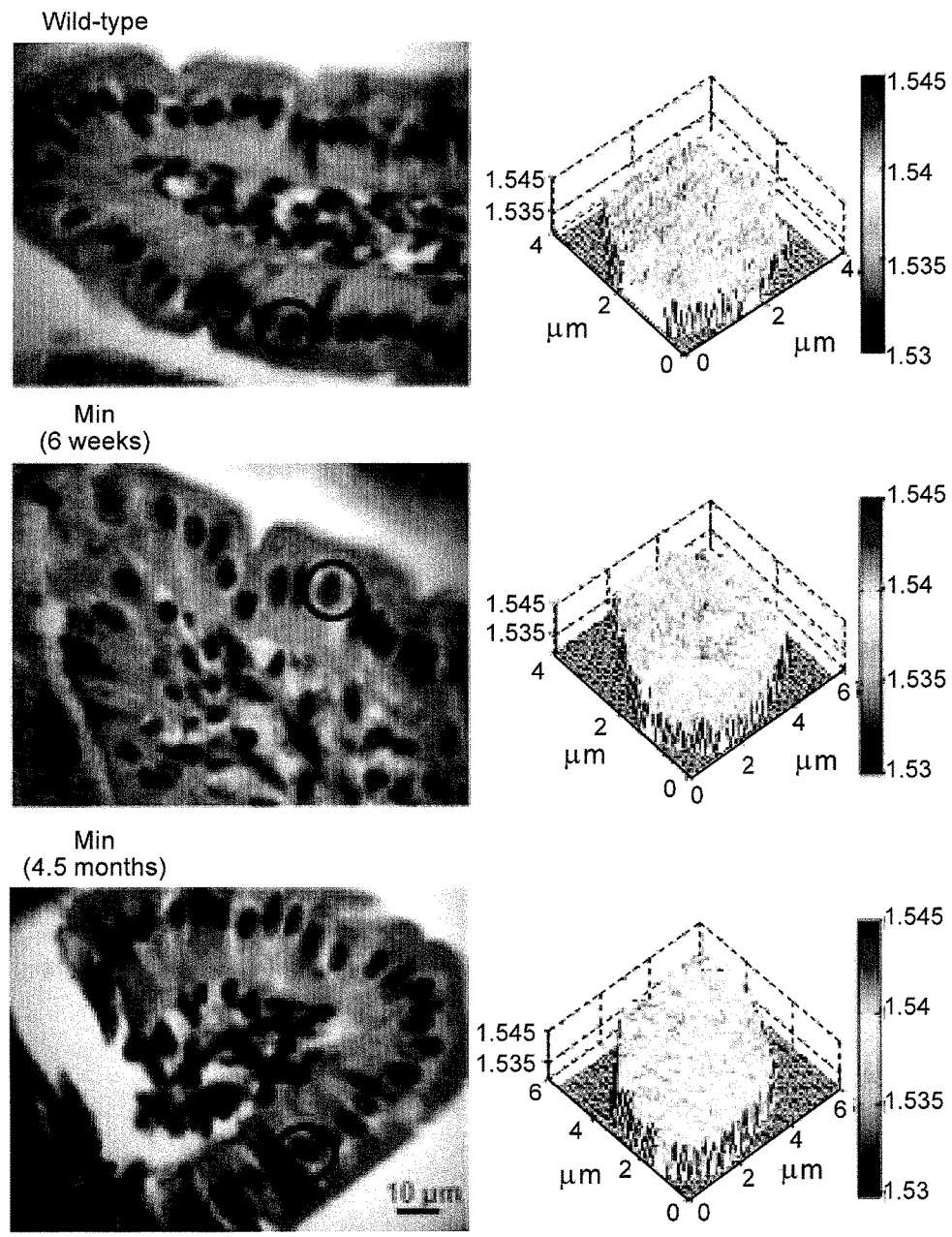
FIG. 16 shows the refractive index maps from the cell nuclei of histologically normal cells from wild-type mice, $APC^{Min}$ mice at 6 weeks and 4.5 months.
Figure 17:
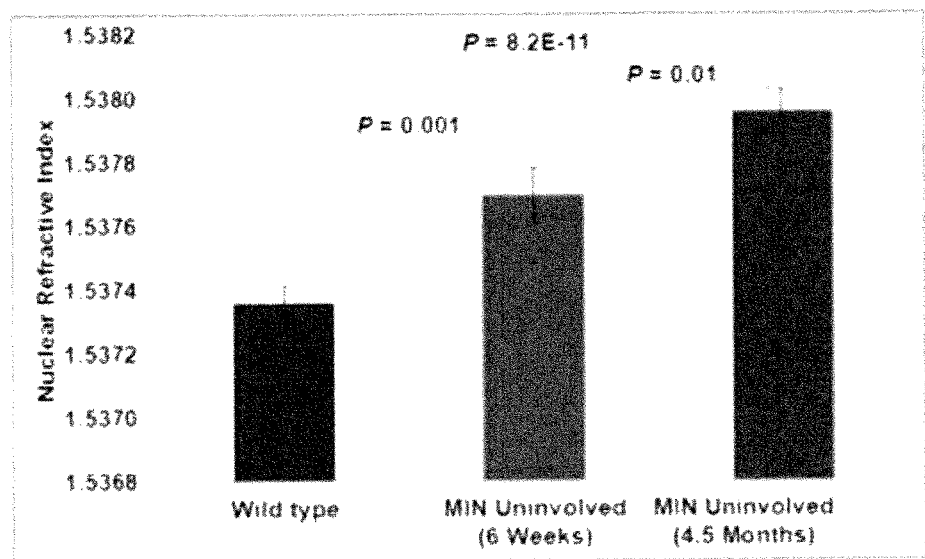
FIG. 17 shows the statistical analysis of average refractive index from cell nuclei in histologically normal-appearing cell nuclei from wild-type mice, $APC^{Min}$ mice at 6 weeks and 4.5 months.

In another study, a total of 12 C57BL mice (6 wild-type, 6 age-matched Min) were studied. A segment of small intestine and colon were cut and processed with standard histology protocol. The nuclear refractive index from small intestine was analyzed at a pre-adenomatous stage (6 weeks) and at 4.5 months when visible multiple adenomatous polyps have been developed in their small intestines. FIG. 16 shows the shows the representative histology images and the corresponding refractive index maps of cell nuclei from histologically normal cells from wild-type and Min mice at 6 weeks and 4.5 months. Although all of those cells were rated as histologically normal by expert gastrointestinal pathologist, the nuclear refractive index maps reveal a progressive change. In FIG. 17, as with the nuclear refractive index maps of histologically normal cells, the statistical means of average nuclear refractive index also showed a progressive change that paralleled the development of intestinal carcinogenesis. As early as week 6 when there was no visible tumor, nuclear refractive index was significantly increased (P=0.001). Such change was further elevated in normal cells from Min mice at 4.5 months (P=8.2E-11). These results demonstrate the promise of SL-QPM-derived nuclear refractive index to detect early-stage carcinogenesis from histologically normal cells.

Barrett's Esophagus and Esophageal Cancer

Barrett's esophagus affects up to 10 million Americans. Careful surveillance is essential to detect esophageal adenocarcinoma (EAC). Current surveillance (i.e., Seattle protocol) is time-consuming, invasive, expensive, and not practical to perform in every affected individual on a regular basis. Importantly, this approach suffers from significant sampling errors with the possibility of missing cancer, due to inability to visually detect intra-mucosal carcinoma and dysplastic lesions in flat Barrett's mucosa. The analysis of normal epithelial cells obtained by endoscopic cytology brushing could potentially simplify the surveillance strategy. An approach based on the concept of field effect was proposed to detect high-grade dysplasia (HGD) or esophageal adenocarcinoma (EAC) through the analysis of non-dysplastic intestinal metaplasia (IM), thus identifying a high risk BE population that warrants intensive endoscopic surveillance. These changes were studied via SL-QPM to allow the discrimination between those high-risk patients with EAC and dysplasia and those low-risk patients without.

In one experiment, a pilot study was performed with 60 patients undergoing scheduled upper endoscopy. The patients were categorized into two groups: low-risk (20 patients; 10 Barrett's intestinal metaplasia, 10 normal esophagus) and high-risk (40 patients; 14 EAC, 18 high-grade dysplasia, 8 low-grade dysplasia). The columnar epithelial cells were obtained via brushing from gastric cardia located at ~2 cm below the gastroesophageal junction. The cells were fixed with Cytolyt and subsequently prepared with Thinprep processor. Optical analysis was done by observers blinded to clinical/endoscopic data.

Figure 18:
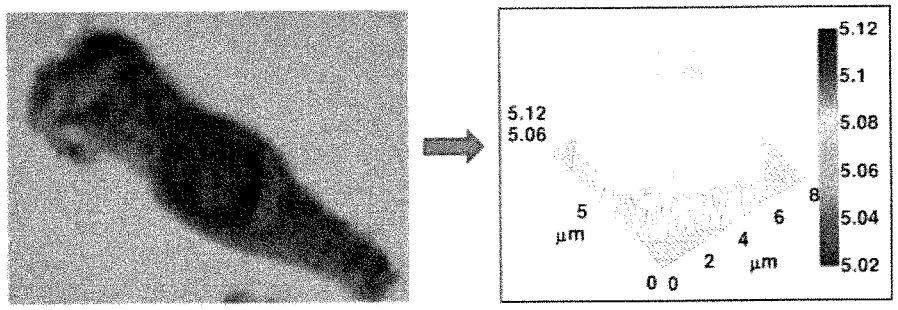
FIG. 18 shows conventional cytology image of columnar gastric cardia cell and corresponding optical path length maps of the cell nucleus from a low-risk patient with Barrett's esophagus without dysplasia and a high-risk patient with Barrett's esophagus with high-grade dysplasia.
Figure 18:
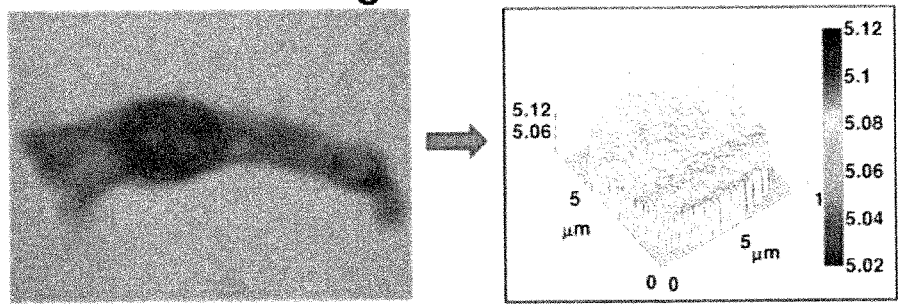
Figure 19:
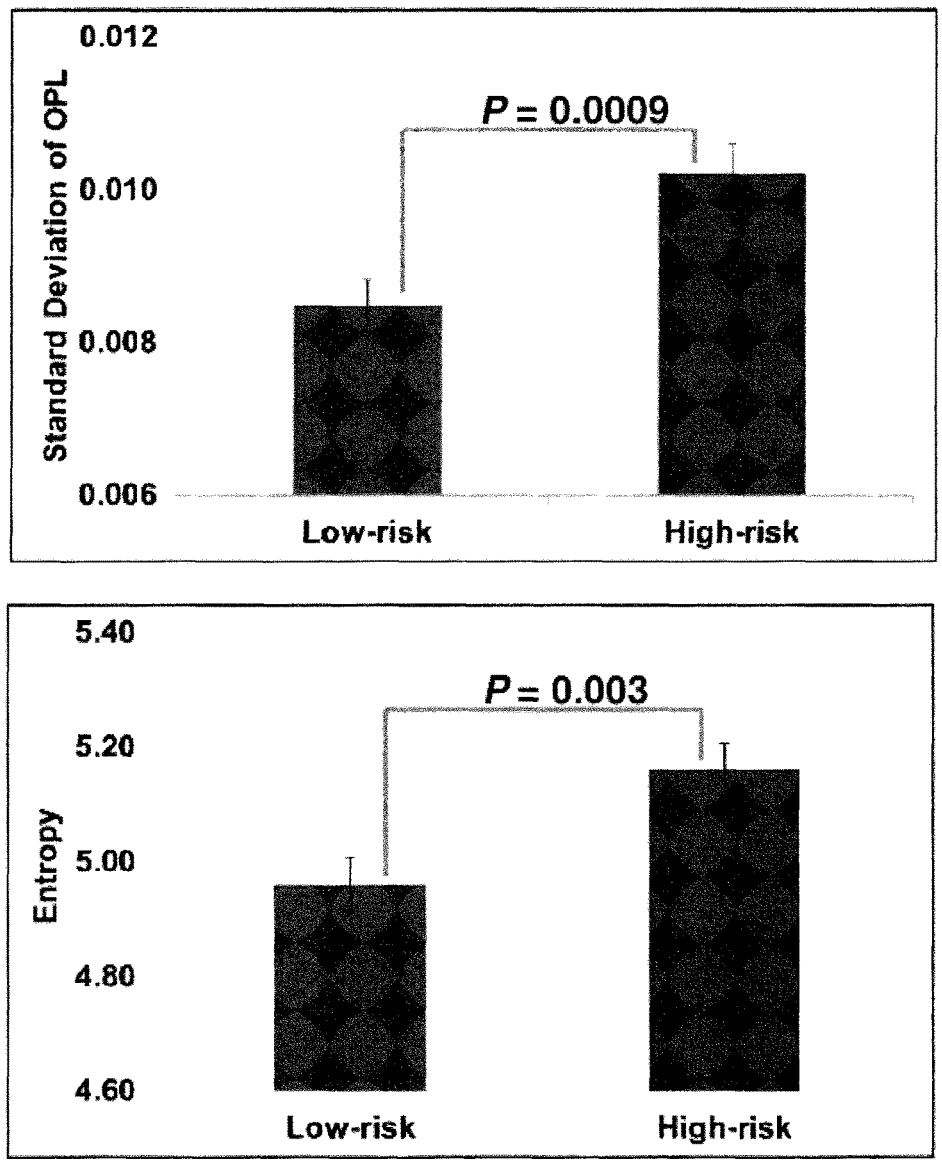
FIG. 19 shows statistical analysis of SL-QPM-derived nanoscale nuclear architecture parameters (standard deviation of optical path length, entropy) of cells from gastric cardia, which were significant in discriminating high-risk esophageal patients with high-grade dysplasia or esophageal adenocarcinoma from low-risk esophageal patients without any dysplasia.

FIG. 18 shows conventional cytology image of columnar gastric cardia cell and corresponding optical path length maps of the cell nucleus from a low-risk patient and a high-risk patient. The nuclear optical path length maps were significantly different in these two cytologically normal-appearing columnar epithelial cells. Several SL-QPM-derived nanoscale nuclear architecture parameters (standard deviation of optical path length, entropy) were significant in discriminating high-risk from low-risk patients, as shown in FIG. 19. A prediction model was developed based on logistic regression by combining SLQPM-derived nuclear architecture parameters. The experiment was able to accurately discriminate patients with neoplasia in 36 out of 40 patients (90% sensitivity) while correctly identifying 12 of 20 low-risk patients (60% specificity).

In another experiment, a retrospective study was performed by selecting a total of 38 BE patients who underwent Seattle protocol biopsies. The patients were separated into two groups: one group of 27 BE patients (11 IM, 16 HGD/EAC) as a training set and another 11 BE patients as a blinded validation set. An expert pathologist reviewed the slides and marked non-dysplastic columnar metaplastic cells, in which nuclear refractive index properties of approximately 40-60 columnar cell nuclei from each patient were analyzed with SL-QPM.

Figure 20A:
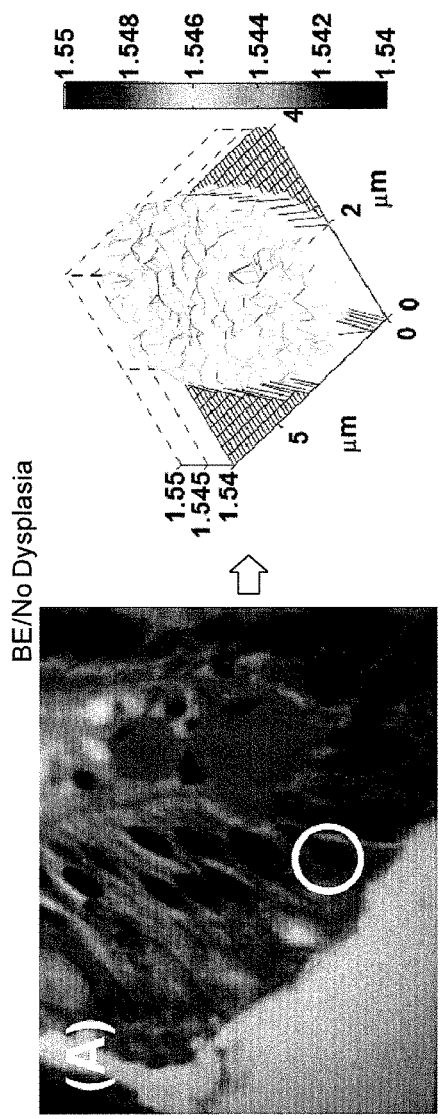
FIG. 20A shows conventional histology images and corresponding refractive index maps of histologically non-dysplastic metaplastic cells of Barrett's esophagus (BE) mucosa from patients without dysplasia.
Figure 20B:
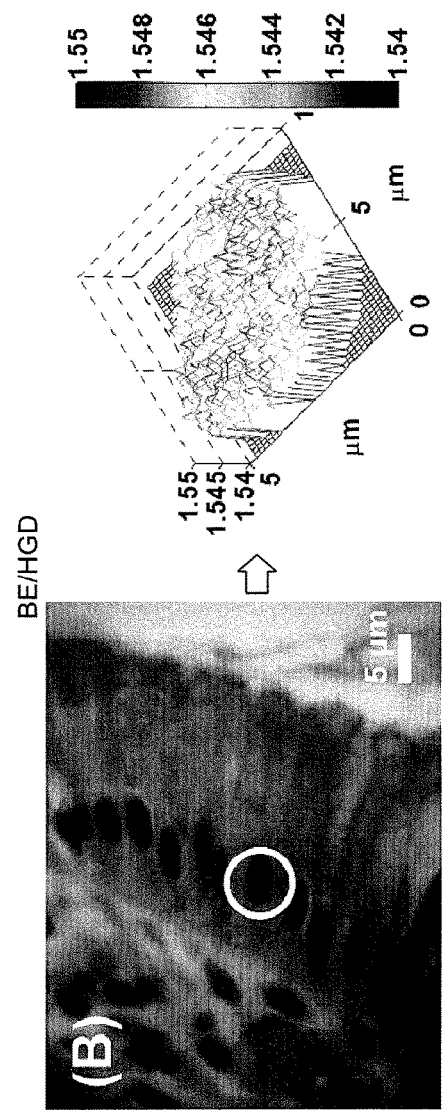
FIG. 20B shows conventional histology images and corresponding refractive index maps of histologically non-dysplastic metaplastic cells of Barrett's esophagus (BE) mucosa from patients with high-grade dysplasia.
Figure 21:
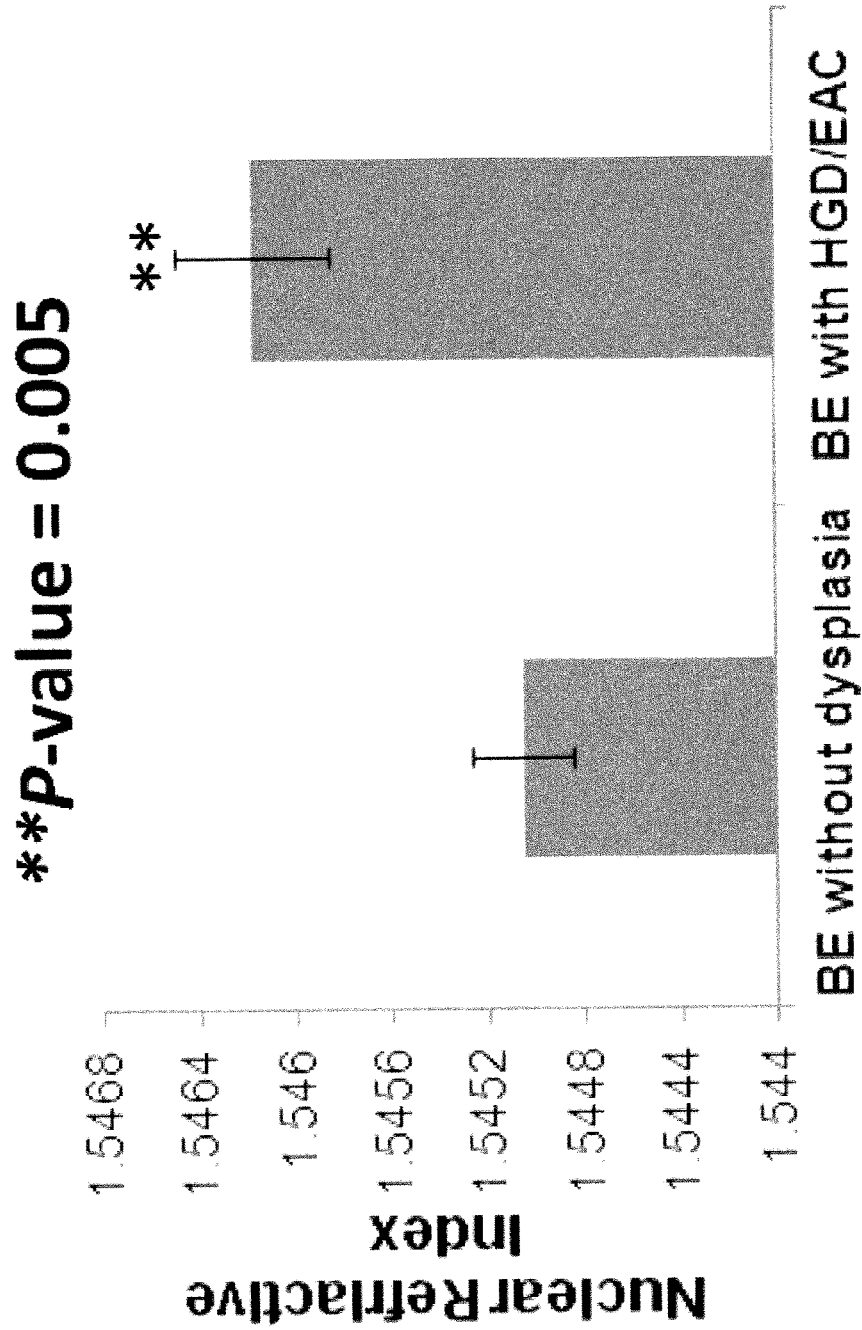
FIG. 21 shows the statistical analysis of nuclear refractive index of histologically non-dysplastic metaplastic cells of BE, which was significantly elevated in patients with BE high-grade dysplasia or adenocarcinoma compared to those BE without dysplasia.

FIGS. 20A-B show the representative histology images and corresponding refractive index maps of histologically non-dysplastic metaplastic cells of BE mucosa from patients without and with dysplasia. Despite their similar histological representation, their refractive index maps exhibited a distinct difference. The statistical analysis further confirmed that nuclear refractive index was significantly elevated in patients with HGD and EAC (P<0.05), as shown in FIG. 21. This parameter can distinguish BE patients with HGD/EAC from those without dysplasia at 91% sensitivity and 77% specificity. The nuclear refractive index properties show great promise to detect BE patients with dysplasia from non-dysplastic columnar metaplastic cells.

The accurate assessment of nanoscale-sensitive nuclear refractive index properties by SL-QPM demonstrates its feasibility for detecting dysplastic/neoplastic Barrett's esophagus from non-dysplastic IM. This approach can potentially simplify BE surveillance by limiting the need for a meticulous FIG. biopsy protocol to a subset of high-risk BE patients.

Modified Cell Lines

Figures 22A, 22B:
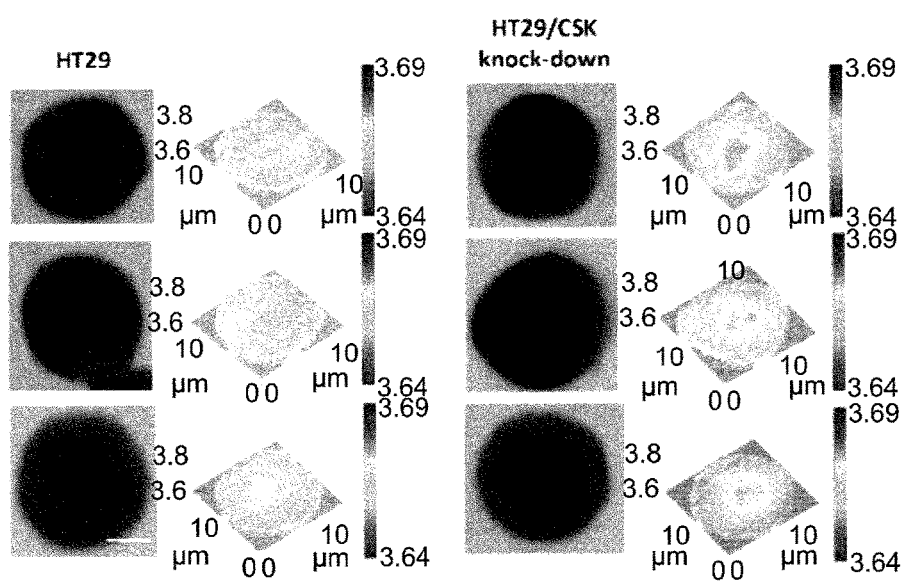
FIG. 22A shows representative cytological images and corresponding OPL maps from HT29 cells.
FIG. 22B shows representative cytological images and corresponding OPL maps from HT29 cells with C-terminus Src kinase (CSK) knock-down.

Multiple experiments were conducted to explore the ability of SL-QPM to quantify the nuclear architectural characteristics in cancer cells. In one such experiment, genetically modified cancer cells with a type of human colonic adenocarcinoma cell line (HT29) were used as a model system, with two variants of HT29 cells: the original HT29 cell lines transferred with empty vector and HT29 cells with a tumor suppressor gene C-terminus Src kinase (CSK) knock-down, which increases the cell proliferation. Importantly, these two cell lines did not exhibit any morphological features that can be distinguished cytopathologically. FIG. 22A shows representative cytological images obtained from bright-field microscope and corresponding OPL maps from HT29 cells and their corresponding OPL maps with the same magnification. FIG. 22B shows representative cytological images and corresponding OPL maps from HT29 cells with C-terminus Src kinase (CSK) knock-down. Scale bars in the image indicate 5 μm. Although the microscopic cytological images look similar (as confirmed by an expert cytopathologist), the OPL images that characterize the intracellular distribution of optical path length were distinctly different in these two types of HT29 cell lines. Colorbar shows the magnitude of optical path length in a cell in microns. As seen by comparing FIGS. 22A and 22B, the OPL maps from HT29 cells with CSK knock-down that have greater cell proliferation, showed significantly elevated OPL values in the nucleus compared with the cytoplasm. In comparison, the nuclear OPL maps showed more homogenous patterns with a slight increase in nucleus versus cytoplasm in HT29 cells.

Figure 22C:
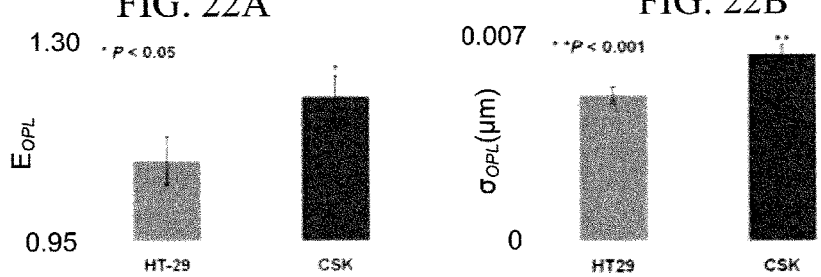
FIG. 22C shows graphs indicating that the nuclear heterogeneity was significantly increased in HT29 cells with CSK knock-down cell lines in comparison with HT29 cells.

Based on these OPL maps, three statistical parameters from the nuclei were quantified: $\langle OPL \rangle$, $\sigma_{OPL}$ and $E_{OPL}$, as explained in greater detail elsewhere herein. As shown in FIG. 22C, the nuclear heterogeneity quantified by $\sigma_{OPL}$ and $E_{OPL}$ were significantly increased in 50 randomly selected HT29 cells with CSK knock-down cell lines compared with 50 randomly selected cells from HT29 (p-value=0.001 and 0.04, respectively), consistent with the increased cell proliferation of this cancer cell line. No statistical difference was found in the average optical path length ($\langle OPL \rangle$) (p-value=0.8). These results indicate that the higher nuclear architectural heterogeneity derived from the nanoscale optical path length map is associated with increased cell proliferation, underlying the potential of this technique in accurate cancer diagnosis at the nuclear level.

The results provided herein indicated that the increased heterogeneity of nuclear density (including $\sigma_{OPL}$ and $E_{OPL}$) provide an important diagnostic parameter for subtle changes of malignancy. The increase in nuclear heterogeneity was clearly seen in the cell line HT29 with CSK knock-down that has increased cell proliferation and may be associated with the higher nuclear density and large chromatin aggregates, as observed in transmission electron microscopic images. Progressively increasing nuclear heterogeneity was further shown in benign cells, indeterminate abnormal cells from cancer sites, and frankly malignant cells from cancer patients. On the other hand, the increased average nuclear density in frankly malignant cells agreed with conventional pathological diagnostic criteria, such as hyperchromasia. However, the elevated average nuclear density did not show a high efficacy in distinguishing cytologically indeterminate malignancy from benign condition.

The techniques of the subject innovation should not be considered as advanced image analysis of conventional digital microscopic images. The OPL map provides quantitative nanoscale information about the nuclear architecture that is otherwise undetectable with conventional optical microscopy. For example, similar texture analysis was performed on conventional phase contrast microscopic images and it was found that the heterogeneity parameters (i.e., standard deviation $\sigma$ and entropy E) cannot distinguish HT29 from HT29/CSK knock-down, as shown in FIGS. 22A-22B, indicating the importance of the nanoscale OPL map.

Ulcerative Colitis and Colorectal Cancer

To further confirm the significance of nanoscale nuclear architecture in human cells and the applicability of OPL analysis in clinical cancer diagnosis, human cytology specimens from patients with colorectal cancer and pancreatic cancer were analyzed using systems and methods discussed herein. The cytology slides were prepared with the standard clinical protocol, as explained in greater detail elsewhere herein. OPL analysis was performed on those epithelial cells of interest selected by an expert cytopathologist.

Experimental results discussed herein show that changes in the nanoscale-sensitive architectural heterogeneity of a cell nucleus can be used to differentiate benign and malignant cells in human cytological specimens from patients with colorectal cancer, demonstrating the capability of systems and methods of the subject innovation to identify malignancy even in cells characterized by pathologists as cytologically indeterminate.

Banked frozen mucosal biopsies were obtained from a group of seven patients with ulcerative colitis who underwent colectomy or colonoscopy, four of whom had no evidence of dysplasia, and three of whom were diagnosed with colorectal cancer. Among the three cancer cases, one patient had frankly malignant cells obtained from the cancer site, while the other two patients had abnormal cells from cancer sites, classified as indeterminate by an expert cytopathologist. The cytology slides were made from frozen mucosal biopsies using a Touch preparation (TP) method, subsequently stained by Diff-Quik stains. These slides were reviewed by an experienced cytopathologist who dotted the colon epithelial cells of interest. Approximately 30-40 cell nuclei per patient were evaluated for OPL analysis.

Cytology specimens were obtained from a group of seven patients with ulcerative colitis (UC), an inflammatory bowel disease, undergoing colonoscopy or colectomy; three patients had been diagnosed with colorectal cancer, while four had no evidence of dysplasia or cancer. The OPL maps from three groups of colon epithelial cells were analyzed: (1) normal cells (i.e., cytologically normal cells from uninvolved tissue site (no active colitis) in the four patients without dysplasia or cancer); (2) cytologically indeterminate abnormal cells obtained at the cancer site (i.e., cells classified by an expert cytologist as being indeterminate in patients with colorectal cancer); and (3) malignant cancer cells obtained at the cancer site (i.e., cytologically classified as malignant cells by cytologist using conventional diagnostic criteria).

Figure 23A:
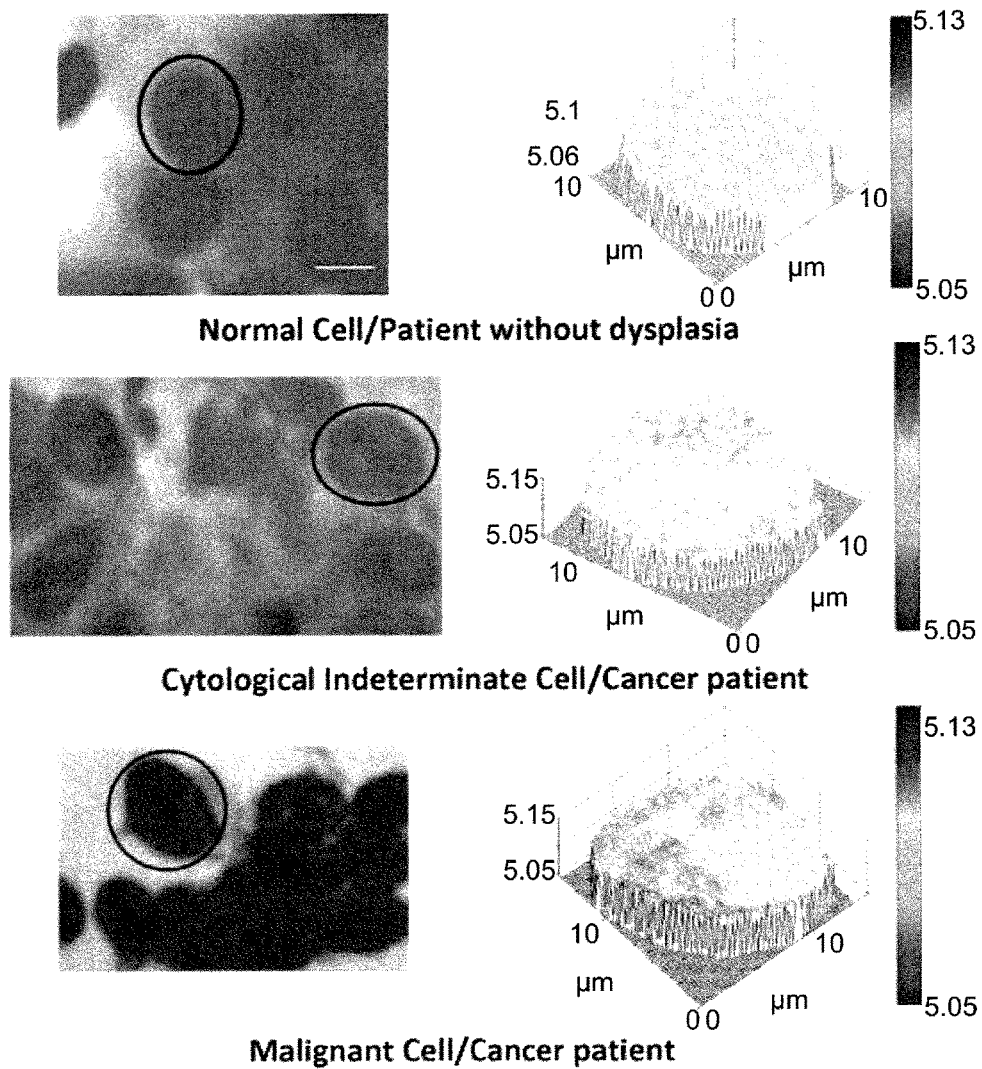
FIG. 23A presents representative cytological images and the representative OPL maps of benign epithelial cells and indeterminate or malignant cells from ulcerative colitis patients.

FIG. 23A presents representative cytological images and the representative OPL maps of benign/normal colonic epithelial cell nuclei in a patient with ulcerative colitis, abnormal cell nuclei from a cancer UC patient (colonic carcinoma) that was called indeterminate by cytological diagnosis, and abnormal malignant cell nuclei that cytologically called malignant from a UC patient with colonic carcinoma. OPL maps reveal the significantly increased intra-nuclear heterogeneity and average optical path length in the malignant cancer cell.

Figure 23B:
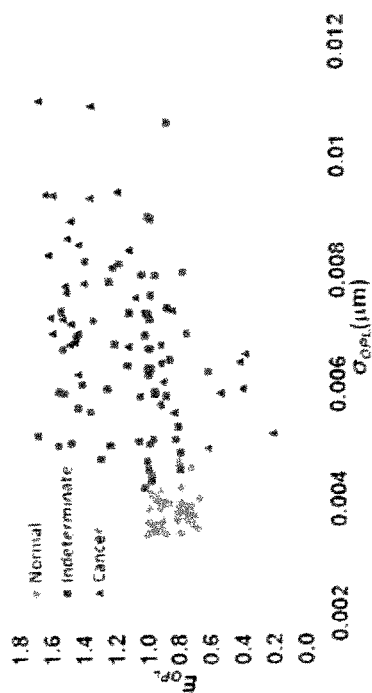
FIG. 23B shows the scatter plot of heterogeneity parameters $\sigma_{OPL}$ vs. $E_{OPL}$ obtained for all the cells from one representative patient in each group shown in FIG. 23A.

To illustrate the inter-nuclear variation, FIG. 23B shows the scatter plot of heterogeneity parameters $\sigma_{OPL}$, vs. $E_{OPL}$ obtained for all the cells from one representative patient in each group: (1) normal epithelial cells from an ulcerative colitis (no cancer) patient; (2) cytologically indeterminate abnormal cells from a cancer patient; and (3) malignant tumor cells from a cancer patient, with each cell nucleus represented by a point ($\sigma_{OPL}$, $E_{OPL}$). Despite the intrinsic variations among different nuclei, the malignant cells and normal cells were well separated. Notably, the majority of cytologically indeterminate abnormal cells in cancer patient were clearly distinguishable from normal cells from patients without dysplasia. These abnormal cells, classified as indeterminate by an expert cytopathologist from a cancer site, resembled the nuclear architectural heterogeneity of the malignant cells.

Figure 23C:
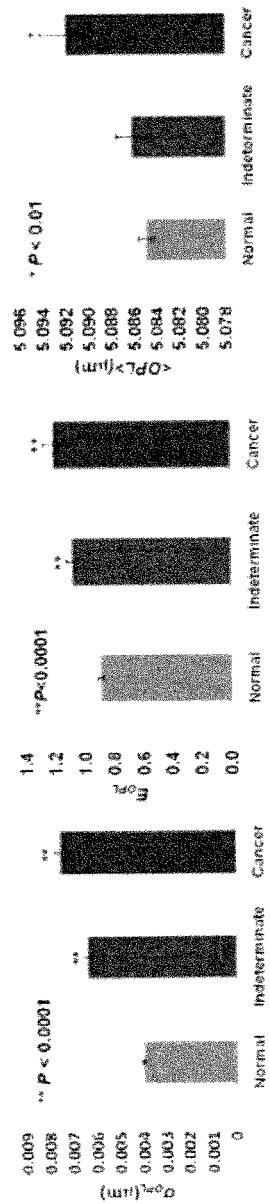
FIG. 23C shows the results obtained from analysis of three statistical parameters from all cells in seven patients from the groups shown in FIG. 23A.

FIG. 23C shows the results obtained from analysis of three statistical parameters from all cells in seven patients (approximately 30-40 cells from each patient). The heterogeneity parameters—$\sigma_{OPL}$, and $E_{OPL}$—were significantly increased in cytologically malignant cancer cells (p-value<0.0001) compared with those in non-cancerous cells. The same heterogeneity parameters were also able to distinguish cytologically indeterminate abnormal cells in cancer patients from those in patients without dysplasia with a high level of statistical significance (p-value<0.0001). Although ⟨OPL⟩ was significantly increased in malignant cancer cells (p-value<0.01), ⟨OPL⟩ did not present any statistical difference in abnormal cells (cytologically indeterminate) obtained at the cancer site when compared with normal appearing epithelial colon cells obtained from patients without cancer or dysplasia. These results suggest the importance of the nanoscale nuclear heterogeneity in detecting subtle changes in tumor malignancy.

Pancreatic Studies

A definitive preoperative diagnosis of pancreatic adenocarcinoma is critical for clinical management, particularly for the appropriate use of neoadjuvant treatment strategies. Endoscopic ultrasound-guided fine needle aspiration (EUS-FNA) is performed on a routine basis for suspicious pancreatic lesions, and while cytology has a relatively high specificity (approaching 100%), the sensitivity remains suboptimal, in part due to the relative rarity of frankly malignant cells.

Ideally, a cytopathologist should be present on site to ensure that an accurate diagnosis is achieved while limiting the number of needle passes if diagnostic tissue is obtained with an early aspiration. Otherwise, 5-7 passes are needed to ensure that diagnostic material is obtained. In this latter scenario, the patients' diagnostic accuracy is compromised by a 10-15% reduction in definitive cytologic diagnoses, longer procedure time, and increased risk for complications. The sensitivity of EUS-guided FNA cytology for pancreatic solid lesions can be significantly compromised by the difficulty in obtaining a diagnostic specimen, a limited number of needle passes, and the absence of an on-site cytopathologist.

The reported diagnostic accuracy of EUS-FNA cytology varies widely, from 64% to 90%. The biggest challenge in diagnosing pancreatic cancer from EUS-FNA cytology is identifying an adequate number of cells that meet cytologic criteria of malignancy. Due to the sampling error and the presence of a desmoplastic response, the small number of sampled cells may not necessarily come directly from the tumor. Furthermore, the cytopathologist looks for morphological features characteristic of malignant cells using a conventional bright-field light microscope, whose resolution is limited by diffraction that detects structural alterations at the scale of ~1 micron.

The systems and methods discussed herein, however (e.g., SL-QPM), are capable of detecting changes in cell architecture as small as 0.9 nm, approximately 1000 times smaller than what a conventional microscope reveals. SL-QPM can use the ultra-high sensitivity of light interference effect, while effectively suppressing multiple noise sources in conventional interferometer-based microscopy and accurately quantifies the nanoscale-sensitive optical path length distribution within each individual cell nucleus. Importantly, this technique can be suitable for analyzing nanoscale architecture characteristics of cell nuclei on original unmodified cytology and histology specimens prepared with the standard clinical protocols without any additional processing or staining.

As explained, systems and methods such as those described herein can be used for various biomedical applications, such as improving the cytological diagnostic accuracy of various cancers, and quantitative mapping of cell mass changes at sub-cellular level. Multiple examples are described herein. For example, as described in greater detail elsewhere, the systems and methods herein can be used to quantify changes during cell cycles, which can be applied in cancer detection.

For the first set of pancreatic results discussed herein, archived cytology specimens obtained at University of Pittsburgh Medical Center by endoscopic ultrasound-guided fine needle aspiration (EUS-FNA) of suspicious pancreatic solid lesions from 45 patients were evaluated, including 13 patients with chronic pancreatitis, and 32 patients with pancreatic malignancy (27 patients with pancreatic adenocarcinoma (PC) and 5 patients with neuroendocrine tumor (NET)). Each diagnosis had been confirmed by surgical pathology. Cytology had correctly identified 23 of 32 patients with malignancy: 18 of 27 pancreatic adenocarcinomas (PC) and all 5 neuroendocrine tumors (NET). All cases were confirmed by surgical pathology or at least 5-year clinical follow-up. All samples were prepared as air-dried smears, and then stained by Diff-Quik stains. The slides were reviewed by an experienced cytopathologist who dotted the epithelial cells of interest on the slides. About 50 cell nuclei per case were analyzed with SL-QPM.

This cohort consisted of a training set of 27 patients and a validation set of 18 patients. The training set consisted of 27 patients: 5 were cytologically diagnosed as NET, and 13 were diagnosed as pancreatic adenocarcinomas; the remaining 9 initially received indeterminate cytological diagnosis; of these, 4 were subsequently confirmed to have adenocarcinoma, while 5 had chronic pancreatitis. The validation set consisted of 18 cases: 5 were cytologically diagnosed adenocarcinoma and 13 were initially interpreted as indeterminate; of these, 5 were subsequently confirmed to have pancreatic adenocarcinoma, while 8 were diagnosed with chronic pancreatitis.

Figure 24A:
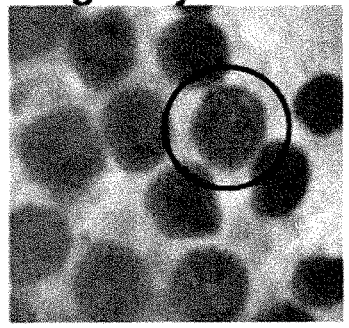
FIG. 24A shows the distinct OPL maps obtained from representative cells from benign, indeterminate, and malignant pancreatic lesions.
Figure 24A:
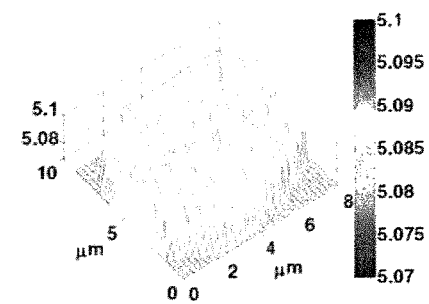
Figure 24A:
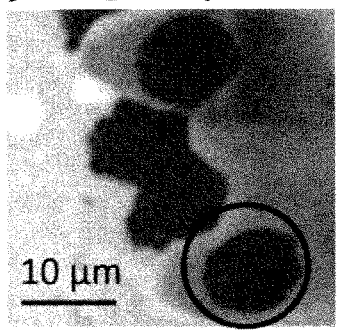
Figure 24A:
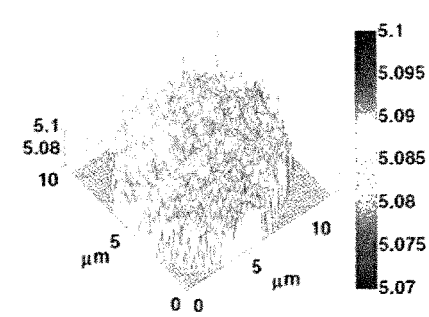
Figure 24A:
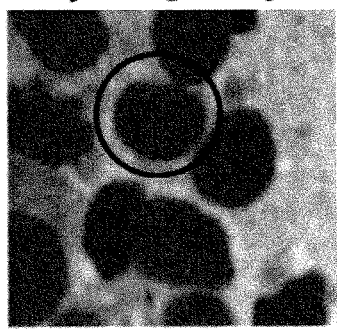
Figure 24A:
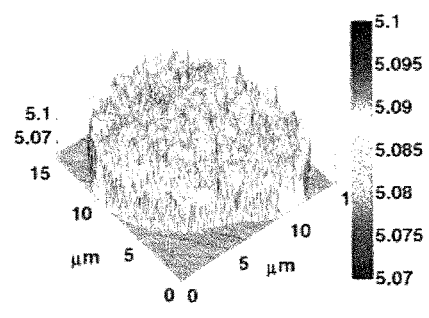

The cytopathologist identified frankly malignant cells and nonmalignant appearing epithelial cells from PC patients and nonmalignant-appearing epithelial cells from benign patients for SL-QPM analysis. Since cytology is only considered to be truly positive when a cytopathologist can provide a definitive diagnosis of malignancy, the cytological diagnoses of atypical, suspicious, and negative were all categorized as "indeterminate". All samples were prepared as air-dried smears followed by Diff-Quik stains. The Diff-Quik method was chosen since it is the simplest and quickest cytology preparation, most commonly used for on-site cytological diagnosis. The slides were reviewed by an experienced cytopathologist who dotted the epithelial cells of interest on the slides for SL-QPM analysis. The individuals who performed the SL-QPM acquisition and analysis were blinded to the patient's diagnosis. The experiment analyzed approximately 30-40 cell nuclei per patient with SL-QPM. To define the efficacy and characteristics of SL-QPM-derived nanoscale-sensitive nuclear architecture, three groups of pancreatic epithelial cells were analyzed for a training set: (1) cells from patients who were who were subsequently confirmed to have chronic pancreatitis; (2) cells labeled as "indeterminate" by the expert cytopathologist from patients who were subsequently confirmed to have adenocarcinoma upon surgery; and (3) malignant cells from cancer patients. FIG. 24A shows the distinct OPL maps obtained from representative cells in these three groups. The malignant cell exhibited a more heterogeneous OPL distribution, in agreement with other findings discussed herein, such as those in connection with colorectal cancer cell lines and human cytology specimens.

To analyze the nucleus-to-nucleus (or cell-to-cell) variation within the same patient, a scatter plot of these three statistical parameters for characterizing the nuclear architecture—$\langle OPL \rangle$, $\sigma_{OPL}$ and $E_{OPL}$—from all the cells in a representative patient from each of the three groups was obtained. All cells from patients with chronic pancreatitis and all the cytologically malignant cells are well separated, with almost no overlap. Notably, the distribution in those cells from cancer patients originally labeled as "indeterminate" by the expert cytopathologist was similar to that seen in malignant cells and distinct from those cells from chronic pancreatitis.

To obtain a diagnostic parameter for each patient, the statistical average of the three nanoscale nuclear architecture parameters ($\langle OPL \rangle$, $\sigma_{OPL}$ and $E_{OPL}$) was calculated over approximately 30-40 cells for each patient, denoted as $(\langle OPL \rangle)_p$, $(\sigma_{OPL})_p$ and $(E_{OPL})_p$, respectively.

Figure 24B:
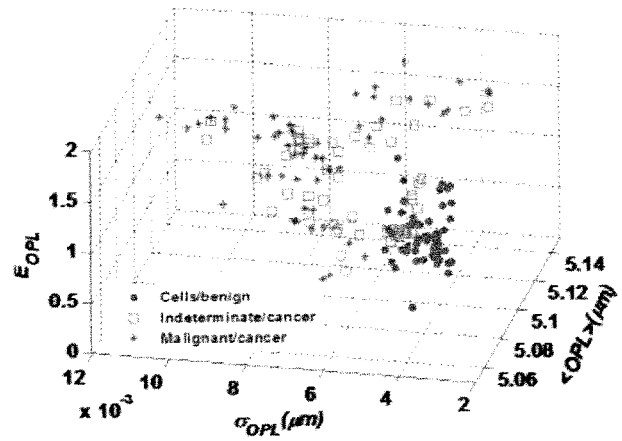
FIG. 24B shows the scatter plot of three statistical parameters used to characterize the nuclear architecture for all cells from one patient in each group shown in FIG. 24A.
Figure 24C:
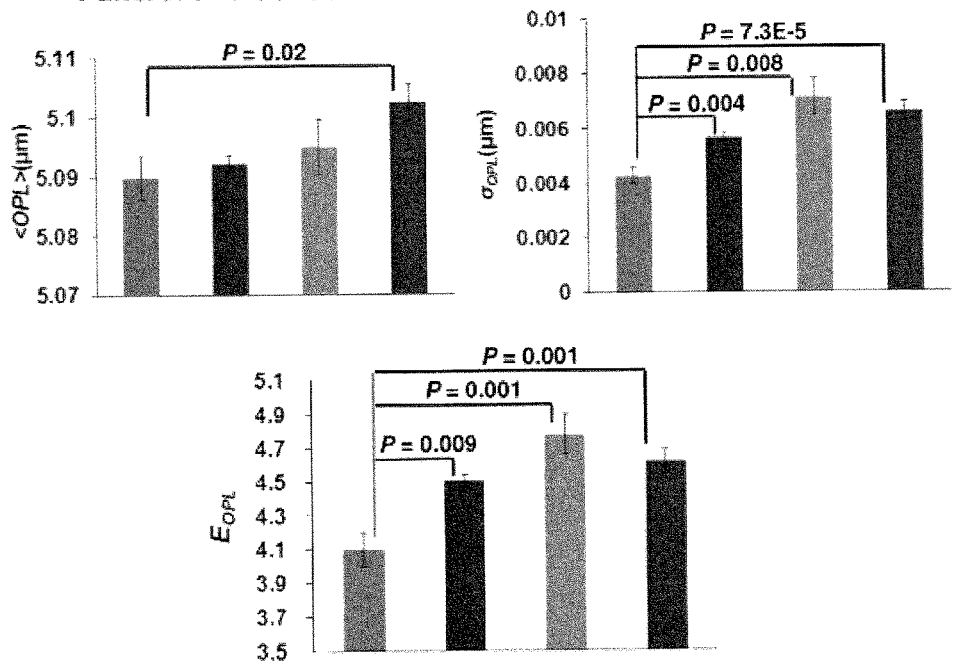
FIG. 24C shows the statistical analysis of optical parameters that was performed using approximately 30-40 cells for each patient for a total of 27 patients in the training set in the study shown in FIG. 24A.
Figure 24D:
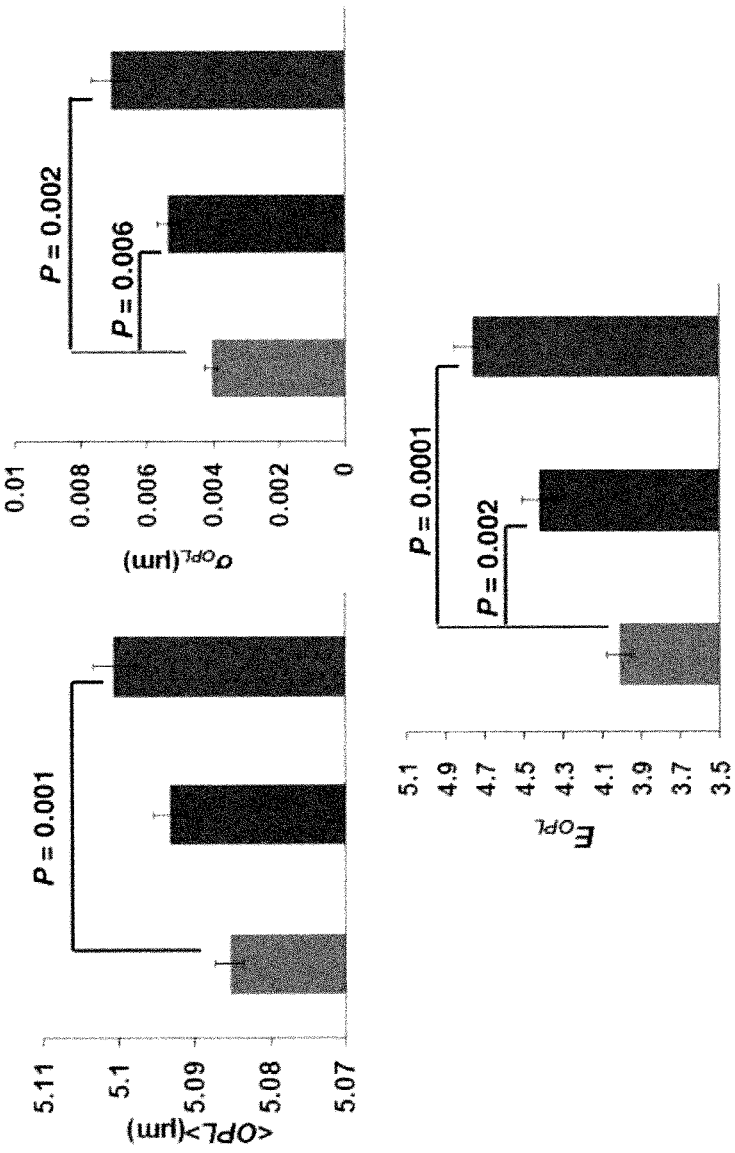
FIG. 24D shows the statistical analysis of optical parameters that was performed using approximately 30-40 cells for each patient for a total of 18 patients in the validation set in the study shown in FIG. 21A.

Statistical analysis was performed on the results from the 27 patients in the training set, who were categorized as: (1) patients who received "indeterminate" cytological diagnosis but were surgically confirmed to have chronic pancreatitis; (2) patients who received "indeterminate" cytological diagnosis but were subsequently found to have pancreatic adenocarcinoma; (3) patients who were cytologically diagnosed and surgically confirmed to have a neuroendocrine tumor; and (4) patients who were cytologically diagnosed and surgically confirmed to have pancreatic adenocarcinoma. All three nanoscale-sensitive nuclear OPL parameters (i.e., $(\langle OPL \rangle)_p$, $(\sigma_{OPL})_p$ and $(E_{OPL})_p$) were significantly increased in cytologically malignant cells from patients with adenocarcinoma compared with those from patients with chronic pancreatitis. FIG. 24B shows the scatter plot of three statistical parameters used to characterize the nuclear architecture: $\langle OPL \rangle$, $\sigma_{OPL}$ and $E_{OPL}$ for all cells from one patient in each group. The majority of cells from benign patients and malignant tumors were well separated, irrespective of their cytological diagnosis. Statistical analysis of all the cells from these 14 patients showed that nuclear heterogeneity expressed by $\sigma_{OPL}$ and $E_{OPL}$ were significantly increased in pancreatic cancer patients (p-value<0.0001), even for those with indeterminate cytological diagnosis, while $\langle OPL \rangle$ only showed a significant increase in cytologically malignant cells, without a high level of statistical significance in cytologically indeterminate cancer cells. Therefore, this nanoscale OPL analysis of nucleus can be used to improve the diagnostic accuracy of pancreatic cancer and further demonstrates the importance of the nanoscale nuclear heterogeneity in detecting subtle changes in tumor malignancy. FIG. 24C and FIG. 24D show the statistical analysis of $E_{OPL}$, $\sigma_{OPL}$ and $\langle OPL \rangle$ that was performed using approximately 30-40 cells for each patient from the patients in the training set and validation set, respectively. The nuclear heterogeneity derived from $E_{OPL}$, and $\sigma_{OPL}$ was progressively increased from normal cells to cytologically indeterminate abnormal cells to frankly malignant cells. The $\langle OPL \rangle$ in malignant cells from cancer patients is significantly increased compared with that in normal cells (student's t-test, P<0.05). However, there was no statistically significant difference in $\langle OPL \rangle$ between normal and cytologically indeterminate abnormal cells. It should be noted that for those patients who received indeterminate cytological diagnosis, the nuclear heterogeneity parameters—$(\sigma_{OPL})_p$ and $(E_{OPL})_p$—were capable of distinguishing pancreatic adenocarcinoma from chronic pancreatitis with statistical significance (P-value<0.01). Therefore, the nanoscale nuclear architecture parameters show great promise to improve the diagnostic accuracy of pancreatic cancer.

A logistic regression model was developed using just the most effective OPL parameter—in this study, nuclear architectural randomness or entropy $(E_{OPL})_p$—with a maximal specificity (minimized false positives) from the 27 patients in the training set. This model achieved 100% specificity and 95% sensitivity.

The prediction rule from the training set was applied to another 18 patients in whom 5 initially were given a correct cytological diagnosis of pancreatic adenocarcinoma and 13 received an "indeterminate" cytological diagnosis on EUS-FNA cytology specimens but were subsequently were found to have pancreatic cancer or chronic pancreatitis upon surgical pathology. The SL-QPM-derived nuclear architectural characteristics discriminated between patients with pancreatic adenocarcinoma and chronic pancreatitis with 90% sensitivity and 100% specificity. The nuclear entropy $(E_{OPL})_p$ correctly identified all four pancreatic adenocarcinoma patients who received a correct cytological diagnosis.

When combining both training and validation sets, the SL-QPM-derived nuclear entropy increased the sensitivity of cytology for identifying pancreatic cancer from 72% to 94% while maintaining 100% specificity. Table 1 summarizes the results:

|  |  | Training Set (%) | Validation Set (%) | Combined Set (%) |
|---|---|---|---|---|
| Cytology | Sensitivity | 82 | 50 | 72 |
|  | Specificity | 100 | 100 | 100 |
| SL-QPM | Sensitivity | 95 | 90 | 94 |
|  | Specificity | 100 | 100 | 100 |

Compared with conventional cytology, SL-QPM can offer a novel approach of assessing the architecture properties of cell nuclei through the characterization of in-situ nuclear architectural properties with a sensitivity of less than a nanometer, which can be extremely responsive to even minute changes in the sub-cellular structures, well beyond what conventional microscopy reveals. Notably, this technique can be directly applied to the original unmodified format (i.e., cytology slides) without any special sample preparation. Additionally, this technique requires only a small number of cell nuclei (~30-40 per patient) and is thus ideally suited for the FNA cytology specimens for which a limited number of cells are available for analysis. Therefore, the ability to analyze the subtle, nanoscale alterations in nuclear architecture on the original cytology specimens represents a significant technical advancement, which allows us to target the biggest challenge in FNA cytology of pancreatic lesions: sampling error.

The nanoscale nuclear architecture properties were quantified by the product of refractive index and the physical thickness of the cell (OPL=nL). If assuming a monolayer of cells has consistent physical thickness for the same cell type, the alterations in optical path length are essentially due to the changes in nuclear refractive index. The increased refractive index has previously shown to arise from the increased mass density (i.e., macromolecular concentration). The finding of increased average optical path length (i.e. $(\langle OPL \rangle)_p$) in the cell nuclei of malignant cells is likely due to the increased density of the nuclear components, such as chromatin and nuclear matrix. Indeed, the increased nuclear density (i.e., hyperchromasia) in cancer cells has been well documented as one of the important pathological criteria for cancer diagnosis.

A progressively increased nuclear heterogeneity in FNA cytology specimens of pancreatic solid lesions was also found in benign cells, indeterminate cells from cancer patients, and frankly malignant cells from cancer patients, quantified by $(\sigma_{OPL})_p$ and $(E_{OPL})_p$. The most important aspect of these nanoscale nuclear heterogeneity parameters is their ability to detect pancreatic cancer from those cells considered as "indeterminate".

The distribution of nuclear architectural parameters from cytologically indeterminate pancreatic cancer cells was found to resemble those of frankly malignant cells, distinct from cells diagnosed with benign conditions, suggesting that these cytological indeterminate cells from cancer patients may share certain common biological characteristics with the frankly malignant cells. Although the specific biological events responsible for the increased nuclear architectural parameters in cancer cells are currently not known, experiments discussed elsewhere herein with cancer cells synchronized at distinct cell cycle phases have demonstrated a significant increase in nuclear density (or nuclear refractive index) and its heterogeneity in cells arrested at $G_2/M$ phases in which there is increased DNA content. This result indicates that increased cell growth may be one possible mechanism responsible for the nuclear architectural changes detected by SL-QPM. These subtle changes in the nuclear structure could also be the results of complex genetic and molecular events from multiple molecular pathways, such as chromatin clumping, nucleolar alterations and genetic instability.

Figure 25:
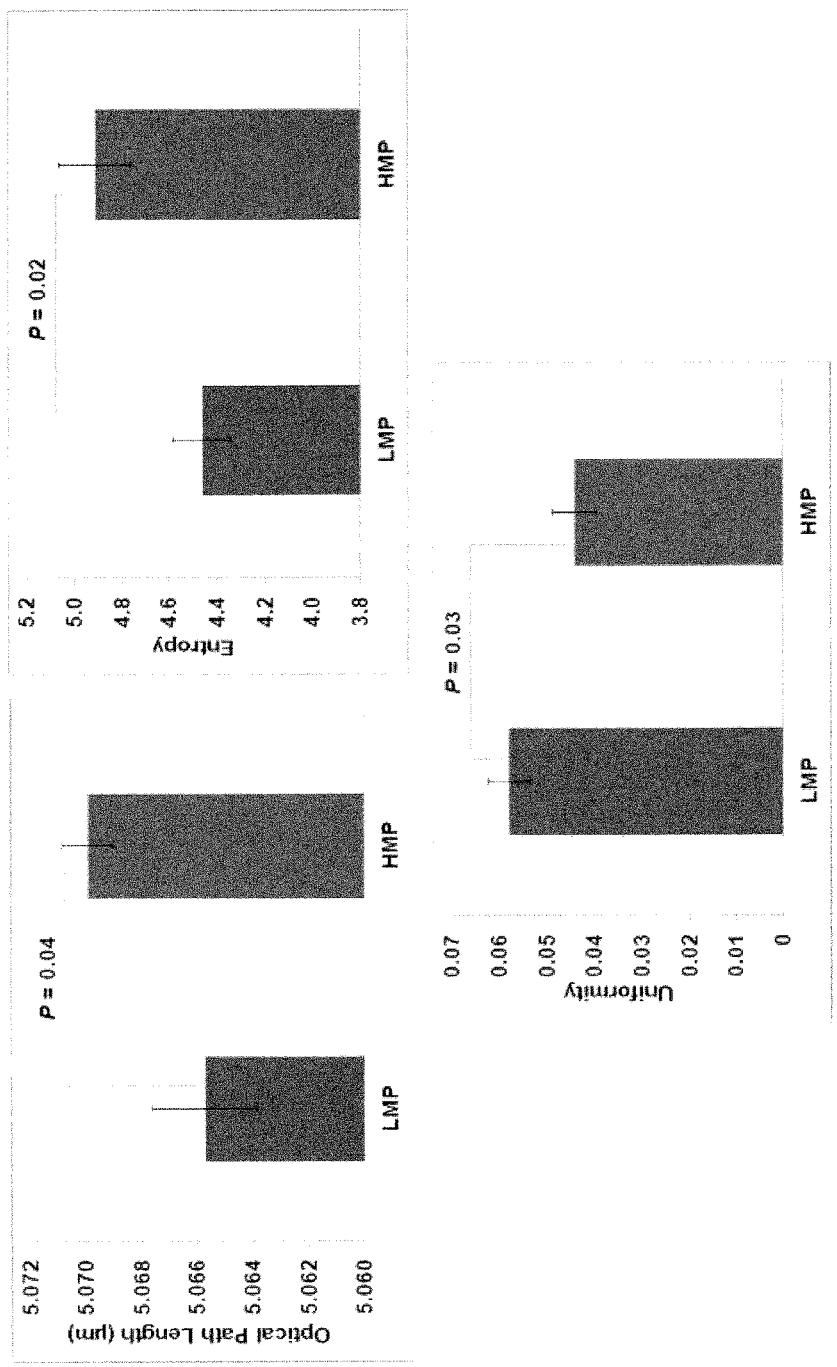
FIG. 25 illustrates a graph that shows a statistically significant increase in the intra-nuclear optical path length and entropy and a decrease in intra-nuclear uniformity in pancreatic cyst patients with high malignant potential (HMP) when compared with those in patients with low malignant potential (LMP).

Another specific example of an application is to improve the diagnostic accuracy of endoscopic ultrasound (EUS) guided fine needle aspiration biopsy (FNA) cytology for risk stratification of pancreatic cysts (i.e., to distinguish cysts with high malignant potential (HMP) from those with low malignant potential (LMP)). Use of endoscopic ultrasound (EUS)-guided fine-needle aspiration (FNA) cytology to detect pancreatic cancer is limited by a high false negative rate largely due to the relative rarity of frankly malignant cells. The widespread use of radiological imaging has identified pancreatic cysts at an increasing rate. Accurate identification of cystic lesions that already harbor cancer or have a high risk to become a cancer presents a unique opportunity for early detection. As shown in FIG. 25, there is a statistically significant increase in the intra-nuclear optical path length and entropy and a decrease in intra-nuclear uniformity in pancreatic cyst patients with high malignant potential (HMP) (n=11) when compared with those in patients with low malignant potential (LMP) (n=16), with statistical significance ($p<0.05$).

Clinically, the SL-QPM-based nuclear analysis could be used in cases for which conventional cytopathology cannot make a definitive diagnosis. Since SL-QPM can be directly applied to original cytology specimens without any additional modification, it can rapidly be integrated into clinical practice. This technique may also reduce the number of needle passes required, thus potentially reducing FNA-associated complications, procedure time, and cost.

Breast Cancer

Using systems and methods of the subject innovation, progressive change in nuclear refractive index properties were found to parallel breast tumorigenesis. More importantly, the nuclear refractive index properties from histologically normal cells adjacent to the tumor can indicate the presence of invasive breast cancer with a high accuracy (~95%). Thus, these nuclear refractive index properties have a potential role in the early detection and management of breast cancer.

Breast cancer is one of the most common cancers and is a second leading cause of cancer death in women. One in eight women in the United States will develop breast cancer during her lifetime. The preoperative core needle biopsy (CNB) is the standard of care for the initial evaluation of breast lesions in patients with abnormal imaging findings, but it has well-known limitations. The central concern for CNB is that patients may harbor malignant disease not captured in the limited biopsy specimen due to sampling errors. This recognized sampling limitation can also lead to unnecessary surgery when certain pre-cancerous lesions (e.g., atypical ductal hyperplasia, papillary lesions) are found on CNB: only 10-20% of these cases are upgraded to cancer following surgical excision. Further, the breast conserving surgery is associated with a significant ipsilateral breast tumor recurrence rate (as high as 40%) despite apparent negative pathologic margins.

Because a complex series of stochastic genetic events via distinct and divergent pathways progress toward invasive breast cancer, specific molecular alterations characteristic of tumorigenesis could offer early and more sensitive means of detecting cancer than visual morphologic abnormalities currently used. Genetic and epigenetic changes such as loss of heterozygosity, microsatellite instability, altered gene expression, altered DNA methylation, and other genetic mutations have been found in histologically normal tissue adjacent to the tumor and in malignant cells themselves. These molecular events provide biological plausibility for the use of molecular markers for the early detection and subsequent monitoring of carcinogenesis in normal tissue adjacent to tumor and in precancerous lesions.

Recognizing that the nanoscale structural changes must accompany such genomic and epigenetic alterations, an experiment examined the refractive index properties of the cell nucleus. The refractive index is a basic optical property that has been widely used to identify a substance or to quantify the concentration or density of particular macromolecules. Changes in refractive index are sensitive to subtle structural changes, even at the scale of just a few molecules. In surface plasma resonance-based biosensors, the binding of biomolecules (e.g., protein, DNA) to a substrate can be assessed by measuring the refractive index near the surface of sensor substrate; changes as small as 0.00001 or a mass density of $10^{-9}$ grams/mm$^2$ can be detected. Due to its high sensitivity at the molecular level, refractive index in the cell nucleus could be used to detect molecular alterations during tumorigenesis.

In an experiment, original unmodified histology specimens of breast biopsies processed with standard clinical protocol (formalin fixed, paraffin embedded, and stained with hematoxylin and eosin) were evaluated. The slides were reviewed by an expert pathologist who marked the region of interest. The refractive index was determined by dividing the measured OPL by the known physical thickness of the tissue section (i.e., 4 µm) controlled by the microtome. It was confirmed that the selected OPL of the cell nucleus was not affected by the absorption profile of the histology stain, with a distinct spatial frequency peak in the Fourier-transformed spectrum from that of the stain alone. The cell nuclei were analyzed within the marked region of interest and the pathological status of all the cells (normal, uninvolved, or malignant) were confirmed by the expert pathologist.

This experiment investigated the nuclear refractive index properties in cell nuclei from normal breast tissue, benign and proliferative breast lesions, tissue adjacent to breast tumors, and invasive breast carcinoma.

The experiment used unmodified archived histology specimens from core-needle biopsies processed according to standard clinical protocol (i.e., formalin-fixed, paraffin-embedded, sectioned at 4 micron thickness and hematoxylin & eosin (H&E)-stained and coverslipped). The specimens came from a total of 136 women categorized into 5 groups according to the criteria in the published literature, including 24 healthy patients undergoing reduction mammoplasty; 14 patients with benign breast lesions; 12 patients with proliferative lesions (with and without atypia); and 86 patients with invasive breast cancer. The tumor staging information for the "Uninvolved" group was as follows: Stage I: 16 patients; Stage II: 10 patients; Stage III: 2 patients; no staging information: 4 patients. The tumor staging information for the "Malignant" group was: Stage I: 26 patients; Stage II: 18 patients; Stage III: 15 patients; Stage IV: 1 patient; no staging information: 5 patients. An experienced pathologist with expertise in breast pathology (Bhargava) evaluated each slide and marked cells of interest. The nuclear refractive index properties were analyzed for at least 40-60 cell nuclei per patient.

TABLE 2

Details of five categorized patient groups and characteristics of core needle biopsy (CNB) specimens.

| Patient group | Number of Patients | Pathology diagnosis of cells analyzed by SL-QPM | Most advanced pathology diagnosis | Mean Age (Mean ± standard deviation) |
|---|---|---|---|---|
| Healthy | 24 | Normal | Normal | 38.3 ± 10.9 |
| Benign | 14 | FCC (2), FCCA (3), FA (9) | FCC (2), FCCA (3), FA (9) | 44.4 ± 15.9 |
| Proliferative* | 12 | IDP (3), DEH (2), SA (2), ADH (2), ALH (3) | IDP (3), DEH (2), SA (2), ADH (2), ALH (3) | 48.1 ± 10.9 |
| Uninvolved** | 32 | Normal | Malignant | 60.4 ± 14.4 |
| Malignant** | 65 | Malignant | Malignant | 59.7 ± 12.4 |

FCC: fibrocystic changes; FA: fibroadenoma; FCCA: apocrine metaplasia; IDP: intraductal papilloma; DEH: ductal epithelial hyperplasia; SA: sclerosing adenosis; ADH: atypical ductal hyperplasia; ALH: atypical lobular hyperplasia.
*The "Proliferative" group was further divided into two sub-groups: without atypia (including IDP, DEH, SA) and with atypia (including ADH and ALH).
**The "Uninvolved" group and "Malignant" group came from 86 invasive cancer patients, including 11 patients from whom both tumor-adjacent normal cells and malignant cells were analyzed.

To provide a quantitative measure of the nuclear refractive index map, two statistical parameters were extracted: average nuclear refractive index $\langle n_{nu} \rangle$ over the two-dimensional refractive index map $n(x, y)$ of the entire cell nucleus, and intra-nuclear standard deviation of refractive index $\sigma_n$, which describes the structural heterogeneity within the cell nucleus. To obtain the characteristic value for an individual patient, the mean value of $\langle n_{nu} \rangle$ and $\sigma_n$ was obtained by taking the average value of 40-60 cell nuclei per patient.

Statistical analysis was performed using SAS statistical software package 9.1.6 (SAS Institute Inc., Cary, N.C.). The statistical comparison between two patient groups was obtained using student t-test, and two-sided P-values were used for all analyses. A multivariate logistic regression using two variables—average nuclear refractive index $\langle n_{nu} \rangle$ and intra-nuclear standard deviation of refractive index $\sigma_n$—is developed as a prediction model to calculate the receiver operating characteristic (ROC) curves.

Figure 26:
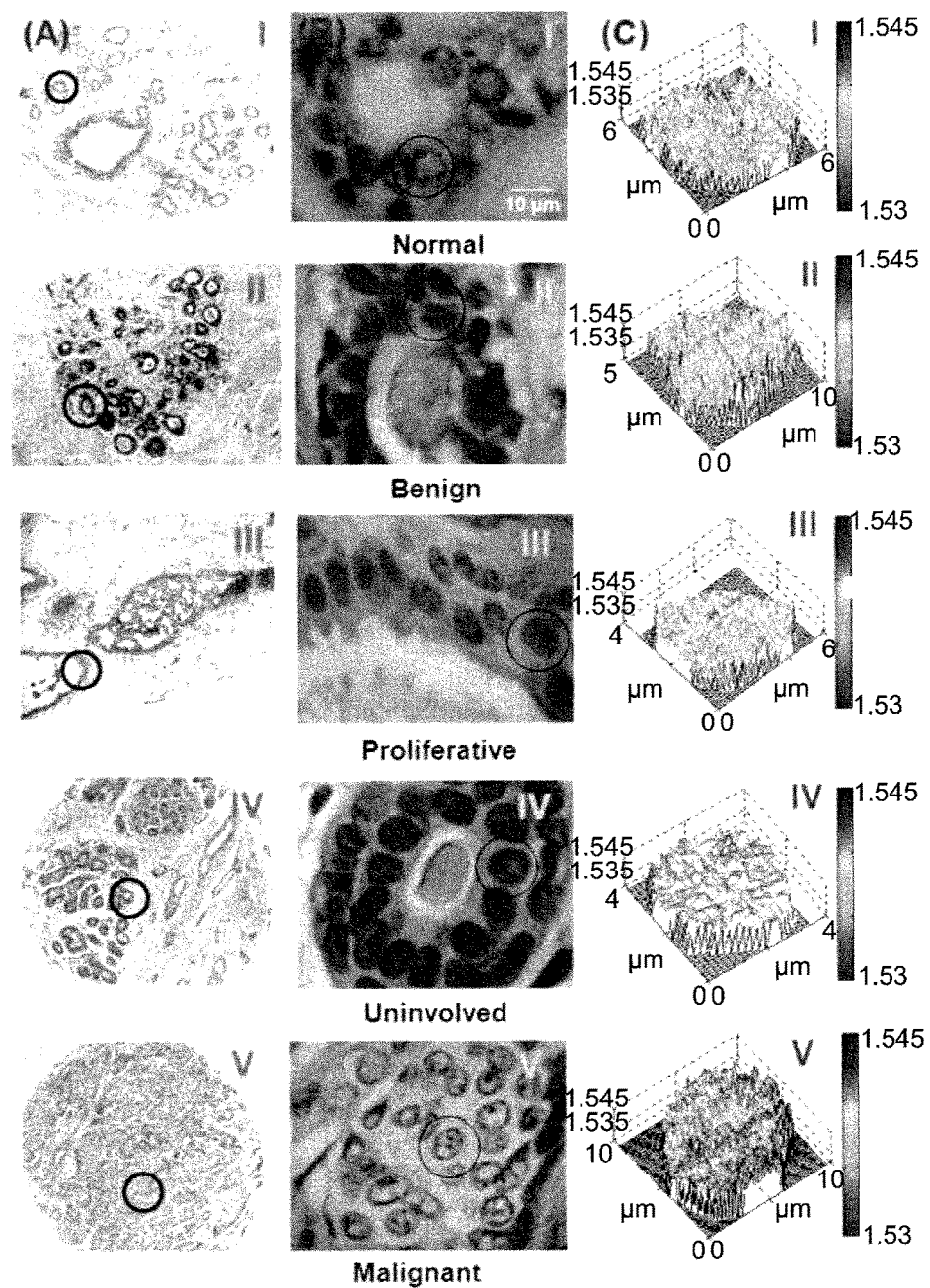
FIG. 26 shows a representative pseudo-color nuclear refractive index map for each of 5 patient groups.

The nuclear refractive index map was the two-dimensional spatial distribution of refractive index from the cell nucleus. Each pixel of the refractive index map represented the average refractive index along the longitudinal direction of the tissue section (i.e., around 4 μm thick). FIG. 26 shows a representative pseudo-color nuclear refractive index map for each of the 5 patient groups. The nuclear refractive index maps revealed a progressive change in the overall value (i.e., color) and spatial distribution of nuclear refractive index from normal cells from the healthy patient to the patient with proliferative lesions to the patient with malignant tumors. It is important to note that more similarities are observed between uninvolved (i.e., histologically normal cells adjacent to malignant tumor) and malignant cells from the invasive breast cancer patients. To quantitatively characterize these changes in the maps, statistical analyses of the nuclear refractive index properties were performed.

Figure 27:
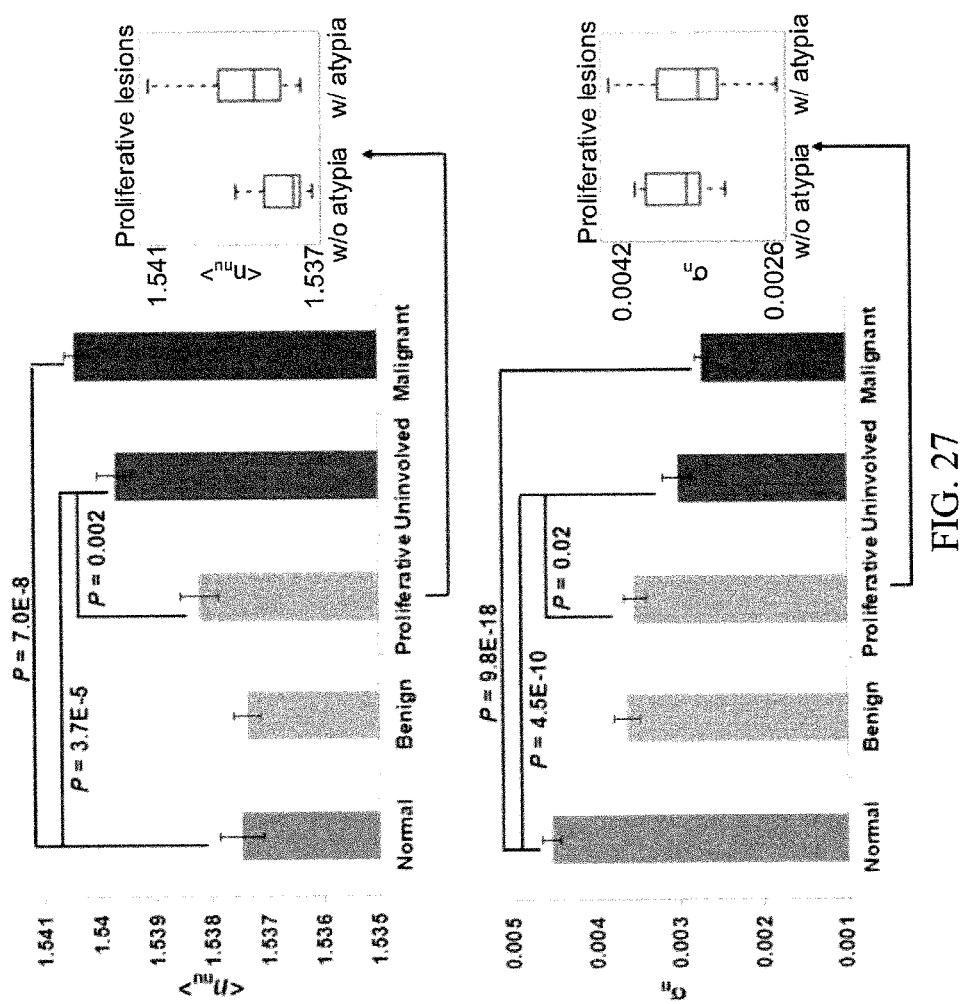
FIG. 27 shows the results of statistical analyses of the nuclear refractive index properties for each of the 5 patient groups in the study of FIG. 26.

FIG. 27 shows the results of statistical analyses of the nuclear refractive index properties for each of the 5 patient groups. As with the nuclear refractive index maps, the statistical averages of $\langle n_{nu} \rangle$ and $\sigma_n$ in the 5 patient groups reveal a progressive change that parallels stage of tumorigenesis. Normal cells from healthy patients and malignant cells from patients with invasive cancer show the most significant statistical difference (P<1E-7), while similar values of nuclear refractive index $\langle n_{nu} \rangle$ are seen in normal patients with reduction mammoplasty and benign breast lesions. A slightly higher nuclear refractive index $\langle n_{nu} \rangle$ was observed in proliferative lesions, but $\langle n_{nu} \rangle$ in cell nuclei from patients without cancer was significantly lower than in those from histologically normal cells adjacent to tumor and from malignant cells (P<0.005). There was also a slight increase of nuclear refractive index ($\langle n_{nu} \rangle$) in proliferative lesions with atypia compared to those without. For each patient, the mean value of nuclear refractive index and intra-nuclear standard deviation of refractive index were calculated by averaging approximately 40-60 cell nuclei. The error bar represents standard error. Box-and-whisker plots show the changes in nuclear refractive index properties in patients with proliferative lesions without atypia (n=7) and with atypia (n=5). It did not reach statistical significance due to small sample size.

The intra-nuclear standard deviation of refractive index $\sigma_n$ also showed a statistically significant difference between normal cells from reduction mammoplasty and normal cells adjacent to tumor (P=4.5E-10), and between normal and proliferative lesions (P=0.02). Most importantly, for those cells marked as "normal" by the expert breast pathologist, their nuclear refractive index properties exhibited a distinct and highly statistically significant change between normal and invasive cancer patients, suggesting SL-QPM was better able to detect the presence of malignancy than conventional pathology.

Figure 28:
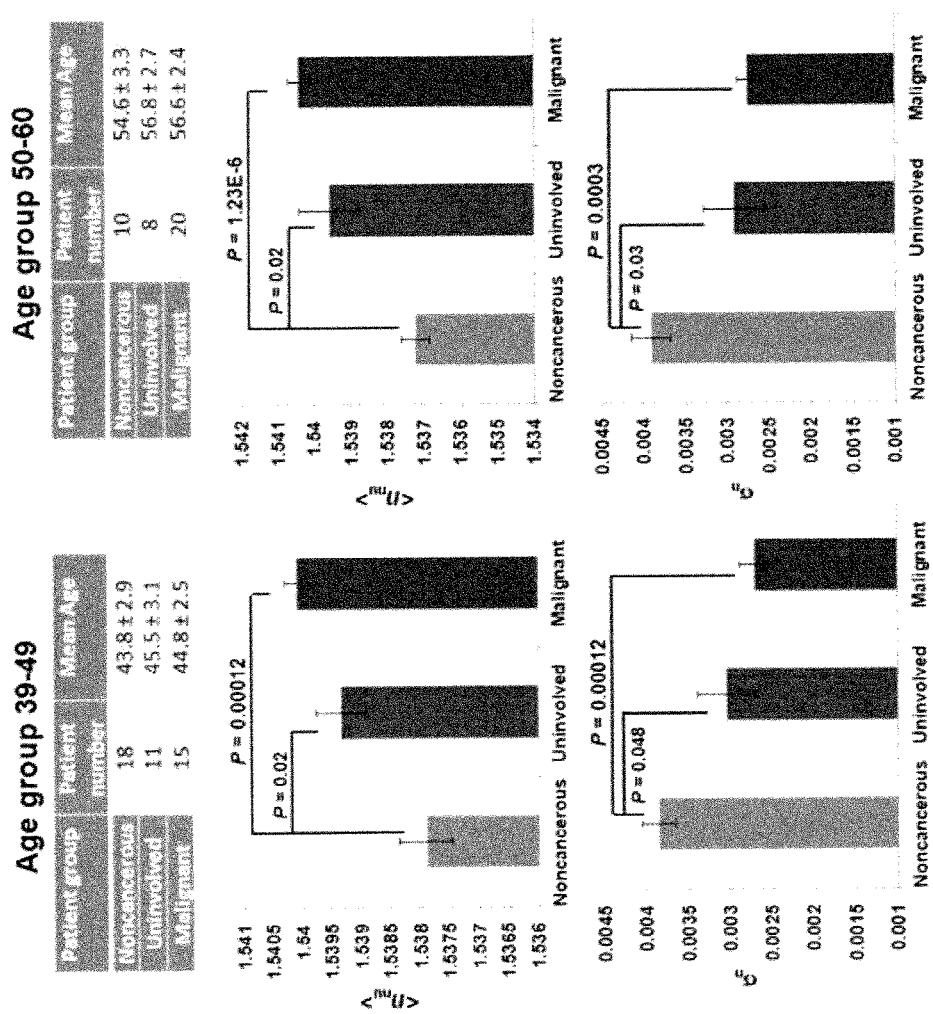
FIG. 28 shows the nuclear refractive index properties of the noncancerous group in the study of FIG. 26 differ significantly from those for age-matched patients in the uninvolved group and from those for age-matched patients in the malignant group.

Because age can be an important confounding factor, it was important to ensure that the observed changes in nuclear refractive index properties reflect breast tumorigenesis rather than age difference. The experiment compared the nuclear refractive index properties for patients divided in two age groups: 39-49 year-olds and 50-60 year-olds. To ensure sufficient statistical power, the normal, benign and proliferative groups were combined into a noncancerous group. As shown in FIG. 28, the nuclear refractive index properties of the noncancerous group differ significantly from those for age-matched patients in the uninvolved group (histologically normal cells adjacent to tumor) and from those for age-matched patients in the malignant group (P<0.001), consistent with what was observed in the mixed patient groups.

Clinically, it is important to predict the early stage tumors. The nuclear refractive index properties ($\langle n_{nu} \rangle$ and $\sigma_n$) in histologically normal-appearing cells from invasive cancer patients who only had Stage I tumor (uninvolved group—Stage I) was compared with those of normal and proliferative groups. The statistical significance for both nuclear refractive index properties was confirmed between normal and uninvolved-Stage I groups (P<1E-6) and between proliferative and uninvolved (Stage I) groups (P<1E-4).

The experiment also looked for potential differences in nuclear refractive index properties based on the common breast tumor subtypes: estrogen receptor (ER), progesterone receptor (PR), and human epidermal growth factor receptor 2 (HER2). Spearman's rank correlation method was used to analyze the correlation of nuclear refractive index properties of cell nuclei from patients with invasive cancer to the expression status of ER, PR, and HER2 (positive vs. negative). The results showed no correlation between nuclear refractive index or intra-nuclear standard deviation of refractive index and ER, PR, and HER2 status (P>0.1).

Figure 29:
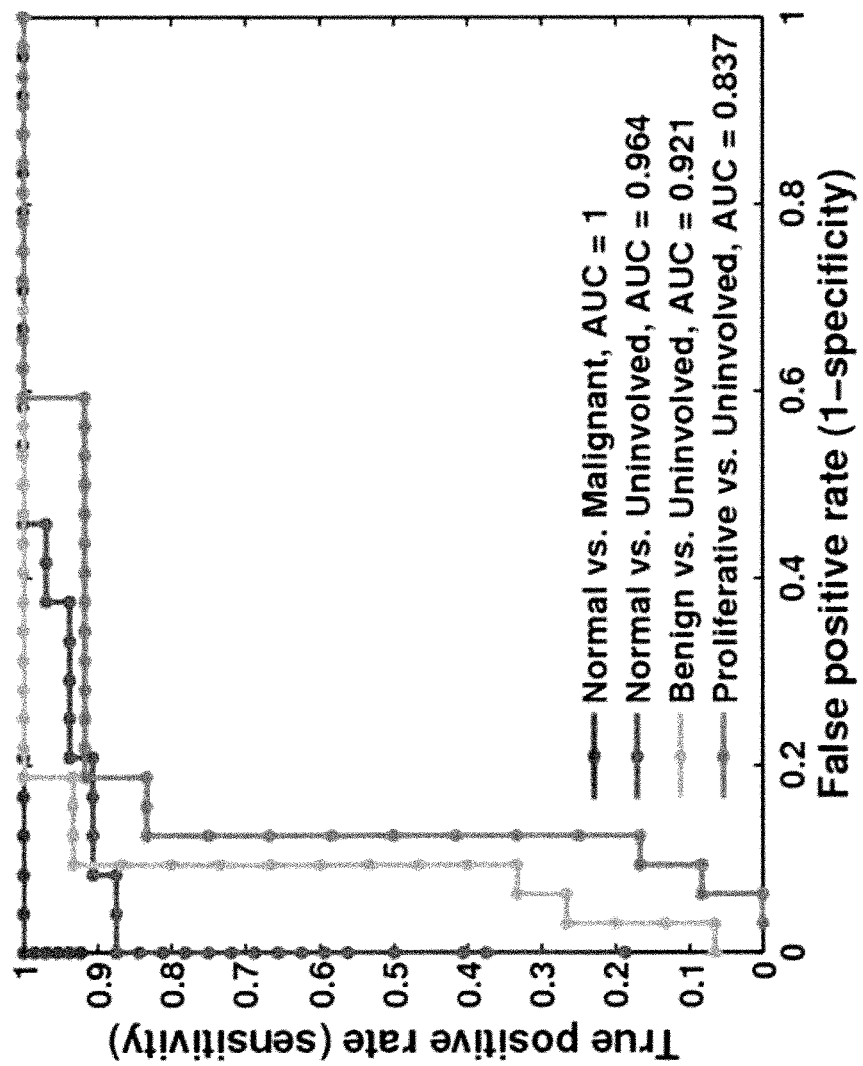
FIG. 29 shows receiver operating characteristic (ROC) curves calculated by using two nuclear refractive index properties for the study of FIG. 26.

To evaluate the potential of nuclear refractive index properties as clinically useful biomarkers for the early detection and risk stratification of breast cancer, receiver operating characteristic (ROC) curves were calculated by using two nuclear refractive index properties in a logistic regression model, as shown in FIG. 29. As the ROC curves show, the nuclear refractive index properties can distinguish normal patients from malignant patients, with malignant cells identified with 100% accuracy (area under curve [AUC]=1). For clinical applications, it is especially important to predict malignancy in histologically normal-appearing cells. The nuclear refractive index properties can achieve an AUC of 0.964 when distinguishing histologically normal cells adjacent to invasive breast cancer from normal cells from healthy patients; from benign lesions (AUC=0.921); and from proliferative lesions (AUC=0.837). Further, leave-one-out cross-validation results in 100% accuracy in discriminating normal and malignant groups, 94.4% accuracy in discriminating normal and uninvolved groups, 88.8% accuracy in discriminating benign and uninvolved groups and 79.4% accuracy in discriminating proliferative and uninvolved groups. Overall, the histologically normal-appearing cells in the setting of invasive breast cancer have distinct nuclear refractive index properties from patients with cells in other settings (healthy, benign and proliferative), with 88.7% accuracy in the leave-one-out cross-validation test.

Applying SL-QPM to unmodified archived histology specimens, it was observed that nuclear refractive index properties can detect breast cancer even in histologically normal-appearing cells adjacent to the tumor, as demonstrated by the high accuracy (~95%) in distinguishing malignant but normal-appearing cells (cancer patients) from normal cells (healthy patients). Furthermore, the nuclear refractive index properties show progressive changes—from normal breast epithelial tissue, to benign lesions, to proliferative lesions (including precancerous lesions), to malignant cells—that parallel the progression of tumorigenesis. Thus, the changes that were observed in nuclear refractive index properties could reflect early events during the neoplastic transformation of breast epithelial cells.

One unique aspect of the nuclear refractive index properties is their nanoscale sensitivity, which allows for the ability to detect subtle changes in nuclear structures at a sensitivity of 0.9 nm (corresponding to a refractive index change of 0.0002). Such high sensitivity is critical in detecting subtle changes in the cell nucleus during breast tumorigenesis. For example, the nuclear refractive index difference between normal cells from healthy and cancer patients is only 0.003, corresponding with an optical path length difference of 12 nm (4 μm tissue section thickness). Similarly, the difference in nuclear refractive index of histologically normal cells from healthy versus cancer patients is only 0.0023, or an optical path length difference of ~9 nm. Such subtle nanoscale and quantitative difference are not easily detected using conventional microscopy techniques.

The fact that histologically normal cells adjacent to tumors display distinct nuclear refractive index properties characteristic of cancer supports the concept of "field effect" or "field cancerization" in breast carcinogenesis. Substantial evidence supports the biological basis of such an effect, including loss of heterozygosity, gene mutations, genomic instability, DNA hypermethylation, and telomerase expression aberrations. These molecular changes could alter cellular processes during neoplastic transformation, such as suppression of growth, repair, apoptosis, and cell cycle regulation. One or more of these molecular events could partially account for the changes observed in nuclear refractive index properties in the tumor-adjacent histologically normal cells and proliferative lesions.

Nuclear refractive index properties can be adopted as novel cellular characteristics to evaluate for the presence of tumorigenesis. The refractive index is a fundamental optical property, a change in which has been shown to be proportional to macromolecular concentration or mass density, with a higher refractive index corresponding to increased density or higher macromolecular concentration. Since cancer is ultimately characterized as uncontrolled cell growth, the accompanying increase in DNA content could contribute to the higher nuclear refractive index. This hypothesis was tested by characterizing nuclear refractive index in HeLa cells throughout cell cycle. Indeed, it was found that the nuclear refractive index is significantly higher in those cells synchronized at $G_2/M$ phase and that 4n DNA content was comparable with those arrested at $G_1/S$ phase with 2n DNA content, suggesting a correlation between increased nuclear refractive index and increased DNA content during cell cycle. These results corroborate the findings of a higher nuclear refractive index in proliferative lesions and malignant cells, which are well known to have increased cell growth. However, nuclear refractive index is not specific to DNA and could reflect changes in nuclear density changes from any macromolecules (e.g., DNA, RNA, protein) in the cell nucleus.

The potential clinical use of these nuclear refractive index properties may be in a broad base regarding the diagnosis, prognosis, and clinical outcome of breast cancer, such as precancerous lesion management, personalized risk assessment and breast tumor recurrence. For example, a diagnosis of atypical ductal hyperplasia on CNB specimen can be further triaged to identify if it has nuclear refractive index properties similar to normal breast tissue or malignant tissue. A subsequent surgery can be avoided if the nuclear refractive index properties are similar to normal breast tissue and excision could be limited only to cases with nuclear refractive index properties of malignant tissue. The addition of other nuclear refractive index or structural properties may further improve the performance characteristics.

This experiment demonstrated that nuclear refractive index properties can detect the presence of breast cancer in histologically normal-appearing cells adjacent to the tumor and can quantify progressive changes in the cell nucleus that parallel the progression of tumorigenesis. Thus, nuclear refractive index properties represent a novel class of biomarker with high sensitivity in detecting the onset of malignancy based on cellular characteristics that cannot be appreciated using traditional histopathology. Validation of their ability to reliably detect such carcinogenic changes would support the rapid translation of SL-QPM to the clinic using routinely collected, unmodified histology slides. As shown by these results, evaluation of nuclear refractive index properties can be applied in the diagnosis and management of breast cancer, including more sensitive assessment of precancerous lesions.

Cholangiocarcinoma (CCA)

The accurate diagnosis of cholangiocarcinoma (CCA) on bile duct biopsies is essential in managing patients with biliary strictures. The accuracy of pathological diagnosis is often challenged by the limited amount of available tissue, rarity of frankly malignant cancer cells and identification of neoplastic cells in the setting of inflammation. This pilot study was conducted to demonstrate the feasibility of SL-QPM-derived nuclear refractive index properties to improve the diagnostic accuracy of bile duct biopsies by detecting neoplastic changes not identified by conventional histology.

Figure 30:
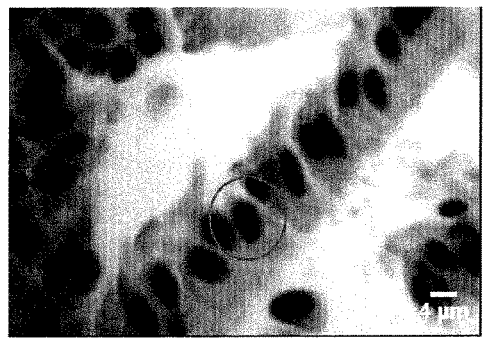
FIG. 30 shows the refractive index maps from a cell nucleus from a benign patient, a cell nucleus of a histologically normal cell (uninvolved) from a patient with cholangiocarcinoma, and a cell nucleus of a malignant cell from a patient with cholangiocarcinoma.
Figure 30:
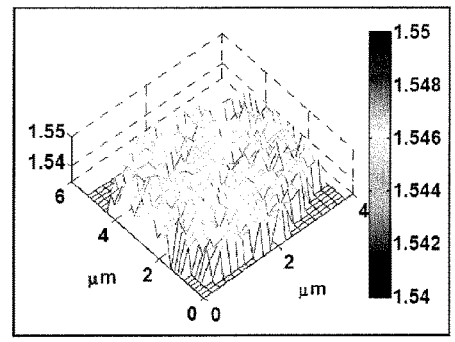
Figure 30:
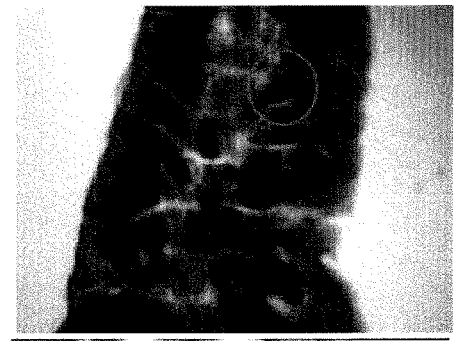
Figure 30:
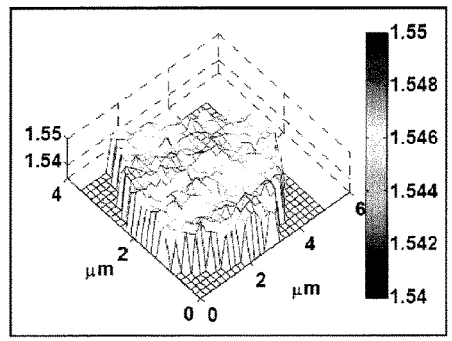
Figure 30:
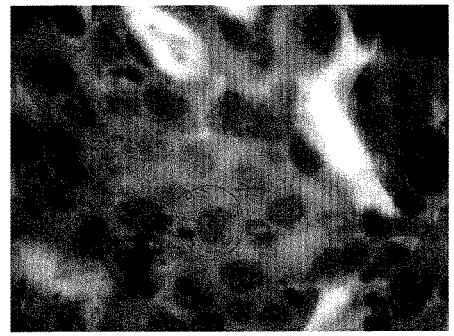
Figure 30:
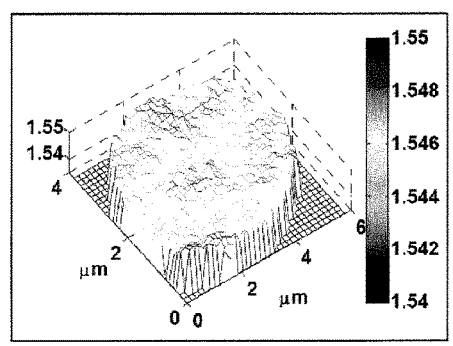

SL-QPM was performed on bile duct biopsies obtained from either ERCP-guided (random) or SpyGlass-directed Spybite® biopsies. The diagnosis was confirmed by a surgical pathologist. The study analyzed three groups of columnar epithelial cells: benign cells from 14 patients with benign strictures, histologically benign cells from 16 patients with CCA, and histologically malignant cells from 13 patients with CCA. Histology specimens processed with the standard clinical protocol (formalin fixed, paraffin embedded and stained with hematoxylin and eosin) were used for nuclear refractive index analysis. The refractive index maps from cell nuclei were shown in FIG. 30. There was a distinct difference between cell nuclei from benign patients and those from malignant patients. It should be noted that the nuclear refractive index maps showed a great similarity between uninvolved cells (i.e., histologically normal cells) and malignant cells from patients with cholangicarcioma.

Figure 31:
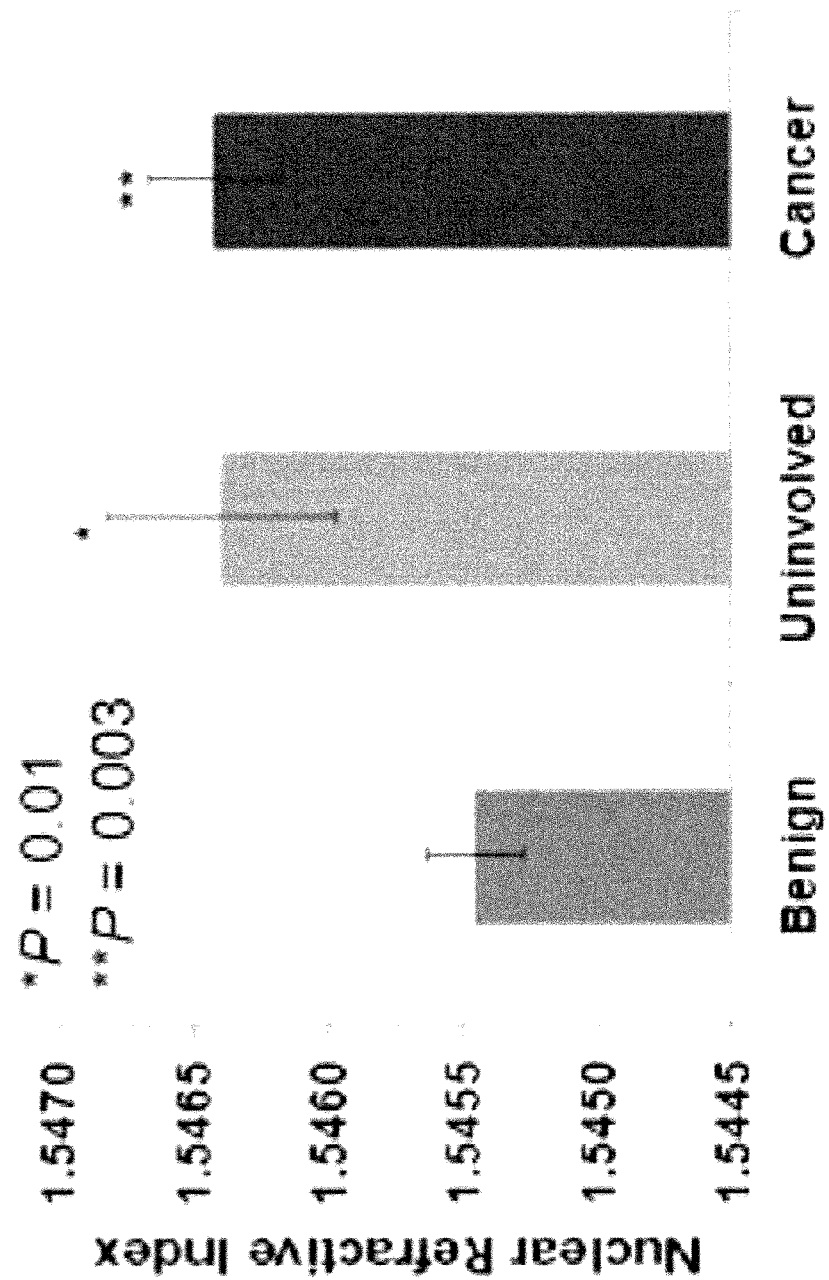
FIG. 31 shows a graph indicating that the SL-QPM-derived nanoscale nuclear refractive index of uninvolved and malignant cells from cholangiocarcinoma patients was significantly increased.

The SL-QPM-derived nanoscale nuclear refractive index of malignant cells from cancer patients was significantly increased (P-value=0.003), as shown in FIG. 31. More importantly, the nuclear refractive index from histologically benign cells from cancer patients is distinctly different from patients with benign disease (P-value=0.01) with a 69% sensitivity and 93% specificity.

The use of SL-QPM derived nuclear refractive index represents a novel type of biomarker for detecting malignancy in histologically benign appearing cells. This optical biomarker can be incorporated into a diagnostic algorithm in which those patients not diagnosed with malignancy would undergo SL-QPM analysis. Additional optical or molecular markers can also be incorporated to further improve the prediction accuracy.

Quantification of Nanoscale Nuclear Refractive Index Changes During Cell Cycle

Cell cycle is a fundamental biological process underlying cell proliferation, division, and DNA repair within a biological system. The investigation of cell cycle is crucial in understanding various important biological processes in living organisms, especially cancer. Due to the significant role of cell cycle in cancer development, results were obtained characterizing the refractive index from cell nucleus in a human cancer cell line in both synchronized cell population and throughout a full cell cycle. Experimental results discussed herein demonstrate that the change in nuclear refractive index has a strong correlation with alterations in DNA content characterized by the standard flow cytometric analysis. Therefore, the altered DNA content and increased cell growth may be one of the possible mechanisms responsible for the increase in nuclear refractive index of cells from cancer patients.

Cell cycle, a process of replicating DNA and dividing a cell, represents a fundamental biological process underlying cell proliferation, division, DNA repair and apoptosis in biological systems. Investigation of cell cycle is crucial for understanding many pathophysiological or pharmacological processes, especially in cancer. Dysregulation of cell division, leading to uncontrolled cell growth with abnormal DNA content is a common biological feature in human cancer. Quantitative characterization of cell cycle is an important tool in cancer detection and development of cancer-targeted chemotherapy.

The eukaryotic cell progresses through four distinct phases of the cell cycle during cell division, including $G_1$, S, $G_2$, and M phases. Cells in the inactive state containing 7.14 pg of DNA enter the cell cycle in $G_1$ phase in which the cell is prepared for DNA replication. During the synthesis phase (S phase), chromosomes are replicated and cells increase their DNA content continuously from 7.14 to 14.28 pg per cell until they reach the state with twice the original DNA content in $G_1$ phase. In the next phase $G_2$, the cell is prepared for mitosis (M phase) during which two cells are produced with half of the DNA contents as in S and $G_2$ phase. The 2N (or 46 chromosomes) DNA content is characteristic of cells in $G_1$ phase, while cells at the end of S phase and the entire $G_2$ phase feature a 4N DNA content (or chromosome number of 92).

Since alteration in DNA content is one of the most prominent characteristics during the cell cycle, the DNA content is often used to determine the cell cycle phases. Several techniques have been used to quantify the DNA content, such as DNA-intercalating fluorescent markers or light-absorbing stains. Using systems and methods of the subject innovation, experiments were conducted that focused on the characterization of an important optical property of cell nucleus—the nuclear refractive index during the cell cycle phases and its relation to DNA content. The refractive index can be used to identify a substance, or quantify the concentration and density of particular macromolecules. This parameter provides fundamental biophysical information about the composition and organizational structure of cells. The refractive index from the cell nucleus on clinical histology tissue specimens from patients with various types of cancer has been quantified with SL-QPM. Experiments have found that the nuclear refractive index is significantly increased in malignant cells from cancer patients compared to those in normal patients or benign diseases. More importantly, it has been found that such increased nuclear refractive index can also be detected even in those cells that are labeled as "normal" or "indeterminate" by expert pathologists, but the patients were subsequently confirmed to have cancer. Further, since SL-QPM can be directly applied on the clinical pathology specimens, it can be used for clinical translation. Therefore, the nuclear refractive index can be used as a biomarker for tumorigenesis, and offers an opportunity for early cancer detection, improving the diagnostic accuracy and risk stratification.

To put the nuclear refractive index on a firmer biological basis, experiments were conducted to determine the biological mechanisms to explain why increased refractive index in cancer patients is observed in both histologically normal and in malignant cells. Since abnormal alterations in cell growth are considered as one of the hallmarks of cancer, the first focus was to characterize the nuclear refractive index in the cell cycle. In the study, the most widely used cancer cell line—HeLa cells, a type of human cervical cancer cell line—was used as the model system. The refractive index from the cell nucleus was quantified at different phases of the cell cycle, which were then compared and correlated with the results from standard flow cytometric analysis.

The cell population was first synchronized at two distinct cell cycle phases, $G_1/S$ and $G_2/M$ phases, using a double thymidine block (an inhibitor of DNA synthesis) followed by treatment of cells with nocodazole (a mitotic inhibitor) according to the standard method. Specifically, HeLa cells were grown in Dulbecco's Modified Eagle Medium (DMEM) supplemented with 10% fetal bovine serum (FBS) (Mediatech, Inc) and 1% penicillin-streptomycin in a 70% humidified incubator at 37° C., 5% $CO_2$. Cells were first blocked at $G_1/S$ phase using a double thymidine block with an exposure to 2 mM Thymidine (Sigma) in the growth media for 17 hours, followed by an 8 hours release period, and a second round of exposure to 2 mM thymidine for 15 hours. At the end of the second exposure to thymidine, there was a $G_1$/S-phase arrested cell population owing to an inhibition of DNA synthesis. Four hours after the cells were released from the block, 100 ng/ml nocodazole was added to the medium for 11 hours to arrest cells at $G_2/M$ transition due to the inhibition of cell mitosis.

To mimic the conditions of clinical histology specimens, a cell block was made from the cells synchronized at $G_1/S$ phase and $G_2/M$ phase. Briefly, cells were trypsinized and resuspended in Cytolyt® solution (Cytec), then they were concentrated by spinning cells in a centrifuge tube until a cell pellet is formed. Then the HistoGel (Thermo Scientific) was added to the cell pellet. After the histogel embedded with cell pellet solidifies, 10% formalin was added to remove the cell block (gel button with specimen cells) from the container. Individual slides from the cell block were then prepared following the standard tissue histology processing protocol with paraffin-embedding, sectioning at 4 μm thickness, mounting on a glass slide, removal of paraffin followed by staining with hematoxylin and eosin, and coverslipped. Data was acquired for approximately 150-160 cells from each sample via SL-QPM system, and the nuclear refractive index was extracted using Fourier analysis, as described in detail elsewhere.

To confirm the status of distinct phases and DNA content during cell cycle, the standard flow cytometric analysis was performed. Specifically, HeLa cells grown and processed in duplicate following the aforementioned cell culture and synchronization protocols were trypsinized and fixed in 70% ethanol. Cells were then washed in PBS, permeabilized with 0.25% Triton X-100 in PBS, and stained with 6% propidium iodide (PI) for 15 min in the presence of RNase (100 μg/mL) in a sodium citrate buffer (40 mM) and 0.1% Trition X-100 in PBS. Stained cells were then passed through the CyAN Flow Cytometer (Beckman Coulter Inc). Since PI is a DNA intercalating dye, the fluorescence intensity is directly proportional to the DNA content in the nucleus. Because different amounts of DNA within the cell depend on the phases of the cell cycle, the intensity distribution of PI fluorescence can be used to determine what percentage of cells are in different phases of the cell cycle.

Figure 32:
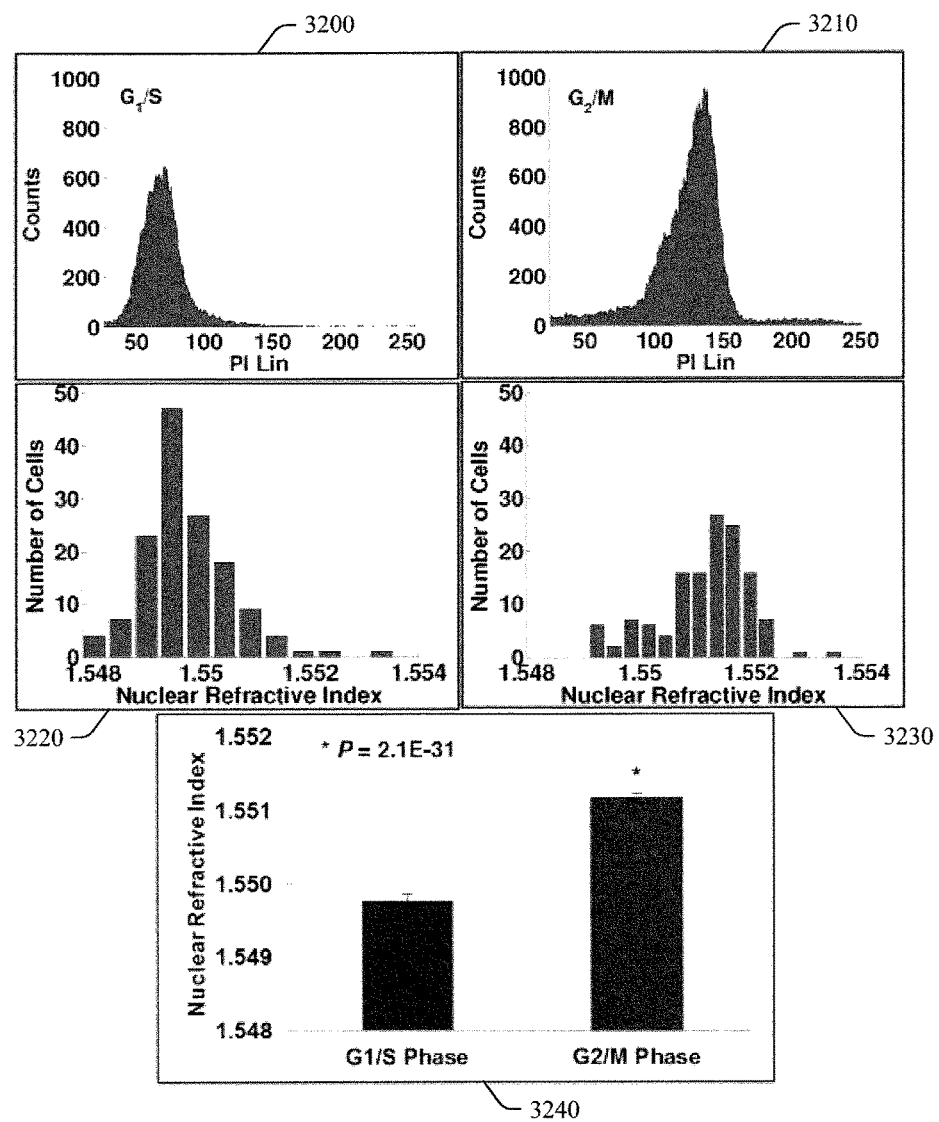
FIG. 32 shows the comparison of nuclear refractive index and flow cytometric analysis of cells synchronized at $G_1/S$ and $G_2/M$ phases.

FIG. 32 shows the comparison of nuclear refractive index and flow cytometric analysis of cells synchronized at $G_1/S$ and $G_2/M$ phases. Graphs 3200 and 3210 show the flow cytometric analysis of fluorescent intensity—a surrogate marker for DNA content, and the corresponding histogram of nuclear refractive index of HeLa cells is shown in 3220 and 3230. Cells arrested at $G_1/S$ phase have 2N DNA content due to an inhibition of DNA synthesis with excess thymidine; while those cells arrested at $G_2/M$ phase have 4N DNA content, having completed DNA duplication during the S phase but without undergoing a cell division, due to the disruption of the microtubules required for cell mitosis by nocodazole treatment. Evidently, the nuclear refractive index distribution resembles the histogram of fluorescence intensity from the flow cytometric analysis. HeLa cells arrested at $G_2/M$ phase with 4N DNA content exhibit a significantly higher nuclear refractive index, as further confirmed by the statistical analysis (P<1E-30) shown in 3240.

Figure 33:
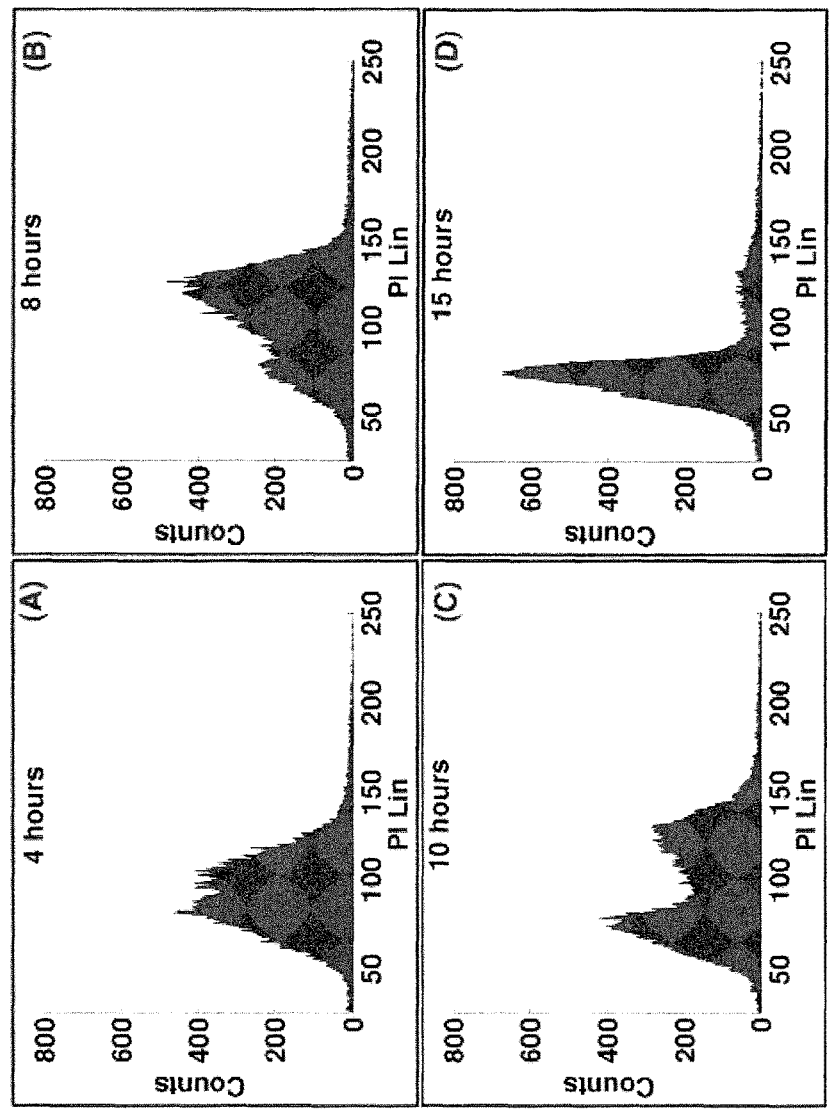
FIG. 33 shows flow cytometric analysis of HeLa cells at 4, 8, 10 and 15 hours to monitor a full cell cycle.
Figure 34:
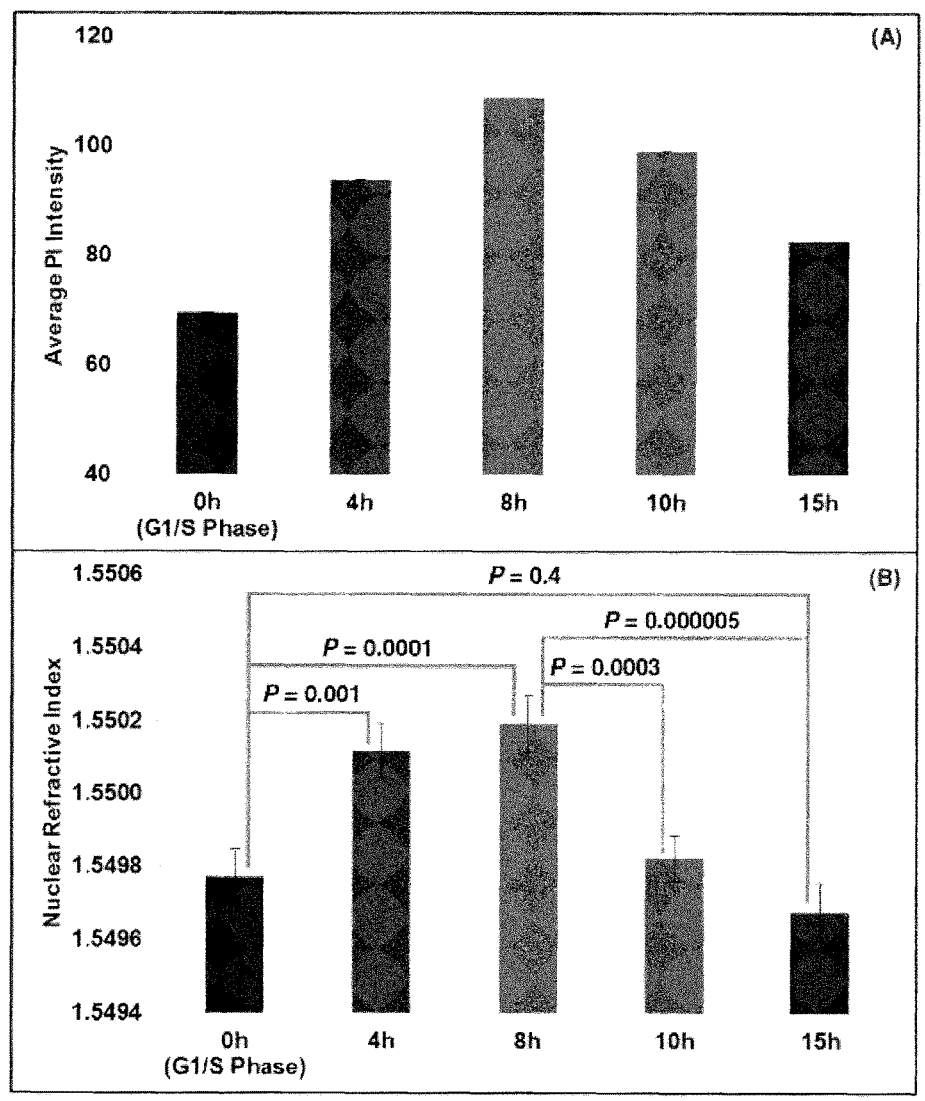
FIG. 34 shows statistical averages of fluorescence intensity and nuclear refractive index at different time points during a full cell cycle.

To further confirm the relationship between the nuclear refractive index and the changes in DNA content, the progression of nuclear refractive index was monitored during a full cell cycle. Cells that were cultured in separate tissue culture dishes were first synchronized using the aforementioned double thymidine block protocol, and then released from the block. Cells from different dishes were then trypsinized and resuspended in Cytolyt® solution at different time points (4, 8, 10, 15 hours) following the second release from thymidine for cell block processing. The nuclear refractive index was quantified, which was compared with the flow cytometric analysis at 4, 8 10 and 15 hours after the release from the second thymidine treatment (arrested at $G_1/S$ phase), as shown in FIGS. 33 and 34. FIG. 33 shows flow cytometric analysis of HeLa cells at 4, 8, 10 and 15 hours to monitor a full cell cycle. FIG. 34 shows statistical averages of fluorescence intensity and nuclear refractive index at different time points during a full cell cycle. There was a clear correlation between nuclear refractive index and DNA content at different phases of the cell cycle. At 4 hours following the $G_1/S$ transition, approximately 50% cells had progressed into the S phase, undergoing DNA replication, as indicated by the increased peak at 4N DNA content. Such change was clearly reflected in the elevated average nuclear refractive index compared to that at $G_1/S$(P=0.001). At 8 hours, only ~25% cells were left with 2N DNA content, and the majority of cells were presented with 4N DNA content, implying that most cells had completed S phase and may have progressed into $G_2$ phase. The corresponding nuclear refractive index showed a further increase (P=0.0001). At 10 hours, more cells (~44%) returned to 2N DNA content, a result of cell mitosis that split the replicated DNA content to half and also led to a significant reduction in nuclear refractive index (P=0.0003). At 15 hours, when most cells (~80%) had completed the mitosis, they showed a prominent peak at 2N DNA content and a further reduced nuclear refractive index (P=0.000005). At this time point, the percentage of cells with 2N DNA content were similar to those arrested in $G_1/S$ phase, as was the nuclear refractive index (P=0.4). These results further confirm that the alteration in the average nuclear refractive index was associated with the amount of DNA content.

These results show a strong correlation between nuclear refractive index and alterations of DNA content during the cell cycle. The refractive index alteration was shown to be proportional to macromolecular concentration or mass density based on a well-established linear dependence: $n=n_0+\alpha C$, where C represents the mass density, and the proportionality coefficient α (specific refraction increment) can be approximated as 0.185 ml/grams for most biological molecules, such as nucleic acid and protein. Therefore, the nuclear refractive index is essentially a sensitive measure of nuclear mass density or concentration caused by the alterations in DNA content during the cell cycle. For example, when DNA content doubles from $G_1/S$ to $G_2/M$ phase, the average refractive index of the cell nucleus increases by 0.0014, corresponding to a nuclear mass density change of approximately 7.6 femtograms/$\mu m^3$. Since cancer is characterized as uncontrolled cell growth that is often associated with higher DNA content, the increased DNA content is one of the likely mechanisms responsible for increased nuclear refractive index which was observed in histologically normal cells and malignant cells from cancer patients. However, cancer or tumorigenesis involves complex biological processes. The observed changes in nuclear structures could also result from other complex genetic and epigenetic events, which need to be further investigated.

In this experiment, the characterization of nuclear refractive index was shown during the cell cycle and the results indicated that altered DNA content and increased cell growth may be one of the possible mechanisms responsible for the observed differences in nuclear refractive index. Furthermore, the nuclear refractive index can serve as an alternative parameter to characterize the distinct phases of cell cycle from simple glass-slide-based cell and tissue specimens. However, the nuclear refractive index should not be considered as a DNA specific biomarker. It can be used to detect cumulative nuclear density changes arising from any macromolecule (e.g., DNA, RNA, protein) in the cell nucleus. Additionally, the nuclear refractive index can also be used as a novel biomarker for cancer detection.

Effects of Stains

To improve image contrast—for better diagnostic visualization of inter-cellular architecture and intra-cellular structure of biological samples—staining agents are commonly used in a clinical diagnostic protocol. In histology samples, for example, (also used in this work) hematoxylin and eosin (H&E) staining is most common. Hematoxylin is a nuclear dye and, along with an oxidizing agent and mordant, stains the nucleus to a deep purplish blue. The cytoplasm on the other hand is eosinophilic and is counterstained by the alcoholic solution of eosin to an orange-pink color. The introduction of color into the histological samples provides the contrast required for their categorical diagnostic evaluation by a pathologist without resorting to surgical biopsy in every case. There are, however, numerous instances where pathologist diagnosis is indeterminate. In such scenarios, if an early cancer detection technique is able to integrate seamlessly with the clinical protocol and provide a correct determinate diagnosis, then the proposed technique has considerable relevance in the clinical setting. Ability to work in a clinical setting has the additional advantage of benchmarking the performance of the technique for pathologically determinate samples by comparing its diagnostic results with that of the pathologist.

To further improve and validate these results, however, the effect of H&E stain on the measured nuclear refractive index was considered. Hematoxylin, the dominant dye in H&E stain, has been documented as a difficult stain to control and standardize. To further complicate matters, hematoxylin is a nuclear dye. Consequently, the inevitable inter-sample variations in hematoxylin lead to corresponding variations in the measured nuclear refractive index. This is because oxidized and alum-enriched hematoxylin binds with nuclei acids and nucleoproteins (e.g. histones) to produce a complex, referred to herein as H&E complex. The presence of this complex alters the structural properties of the nucleus leading to stain-induced changes in the measured nuclear refractive index. Thus, the presence of H&E stain is the cost of working within the histology-based diagnostic protocol. This is true not just for the techniques discussed herein, but for any technique designed for clinical use.

In aspects of the subject innovation, a correction method to remove the stain-induced nuclear refractive index variations can be used. Moreover, the method is not limited to the particular technique disclosed herein, but can be adapted to other phase-based quantitative microscopy methods. The only requirement is the capability to make reflection- and transmission-mode measurements.

In a cell nucleus, the variation in H&E stain manifests as a variation in the concentration of the H&E complex within the cell nucleus (the cell nucleus uptake). Cell nuclei with low uptake appear lightly stained, while cells with high uptake appear darkly stained. The technique discussed herein is based on linearly relating this variation in cell uptake to the corresponding variation induced in nuclear refractive index. This linear relation results from a simple modification to the well-established empirical linear model relating changes in dry cell nuclear mass to the corresponding nuclear refractive index changes.

As discussed above, for SL-QPM, the spectroscopic interference intensity data cube of the cell nucleus under study ($I(x,y,k)$; k=free space wavenumber) can be acquired by (x-direction) horizontal scanning of the (y-direction) vertical slit of the spectrograph. Specifically, at each scanning step x, a CCD camera can record a slice of the data cube corresponding to the y and k directions. The spectroscopic interference data cube can mathematically approximated by $$I(x,y,k)=|E_r(x,y,k)|^2+|E_s(x,y,k)|^2+2|E_r(x,y,k)||E_s(x,y,k)|\cos(\varphi(x,y,k)) \quad (9)$$

where, $E_r(x,y,k)$ and $E_s(x,y,k)$ are the reference and sample beam electric fields respectively, and $\varphi(x,y,k)$ is the phase difference between them. The pixel-wise Fourier transform of $I(x,y,k)$ along the k direction—after removing the bias term—gives $I_F(x, y, z')$, where z' is the optical path length. The amplitude of $I_F(x, y, z')$, $|I_F(x, y, z')|$, can be used to find the prominent peak corresponding to the OPL of interest, $z_p$. The depth-resolved phase map image of the cell nucleus can then given by equation 10:

$$\Phi_r(x,y)=I(x,y,z')|_{z'=z_p} \quad (10)$$

This phase map captures the phase changes corresponding to subtle nuclear structural changes. The total phase, however, has to also account for absolute phase $\Phi_a(x,y)=kz_p$. Therefore, total phase can be written as $$\Phi(x,y)=\Phi_a(x,y)+\Phi_r(x,y) \quad (11)$$

and the corresponding OPL image can be written as $$opl(x,y)=\Phi(x,y)/(2k) \quad (12)$$

The factor 2 in the denominator accounts for the double path length due to the reflectance-mode configuration. The free-space wavenumber k corresponds to $\lambda=550$ nm, the center wavelength of the source. Given the knowledge of sample thickness L, the refractive index image of the cell nucleus is finally obtained using $$opl(x,y)=(n(x,y)+\Delta n(x,y))L \quad (13)$$

where n(x, y) is the refractive index associated with the absolute change in the optical path length, while the intrinsic structure of the cell nucleus is captured by $\Delta n(x,y)$. It is through the sensitive measurement of $\Delta n(x, y)$ that systems and methods of the subject innovation are able to classify the sample under observation.

The variation induced in nuclear refractive index by variation in the H&E complex affects the measurement of $\Delta n(x,y)$. Therefore, the correction model discussed herein modifies the observed $\Delta n(x, y)$ such that the inter-sample nuclear refractive index variations arising due to inter-sample H&E stain variations are removed and all the samples are standardized to the same reference. Mathematically it is described as $$\delta n = \alpha_r C_r \quad (14)$$

where, δn is the change in nuclear refractive index due to nucleoprotein or nuclei acid concentration C, and α, is a constant of proportionality referred to as the specific refraction increment. The specific refraction increment measures the increase in refractive index of the protein solution for a 1% increase in protein concentration.

Equation 14 can be re-interpreted in accordance with the Beer-Lambert law because the presence of H&E complex results in absorption of incident light in accordance with it. Specifically, the right hand side of equation 14 can be divided and multiplied by the unknown, but constant, molar absorptivity ε of H&E complex to get $$\delta n = \left(\frac{\alpha_r}{\varepsilon}\right)(\varepsilon C) = \beta \alpha. \quad (15)$$

This operation does not change equation 14, but allows it to express C in terms of the absorption coefficient α=εC, and a constant of proportionality β that can be referred to as the absorptivity-modified specific refraction increment. The value of α can be computed by operating the SL-QPM system in the transmission-mode and employing the Beer-Lambert law $$A = \varepsilon L C. \quad (16)$$

The absorbance A can be calculated from the incident and transmitted light intensity, while the sample thickness L is experimentally controlled using microtome sectioning. The absorption coefficient can then be given by α=A/L.

The applicability of the Beer-Lambert law assumes a uniform absorbing material. In practice this is not always true because the H&E complex is present only where the nucleoprotein and nucleic acids are present for hematoxylin to bind with. To mitigate this problem and ensure stricter conformity to the assumption, small regions can be considered within the nucleus and the absorption coefficient can be computed for each region. This can result in an absorption coefficient image α(x,y) where each pixel corresponds to one single nuclear region. Therefore, equation 15 can be re-written as $$\delta n(x,y) = \beta(x,y)\alpha(x,y). \quad (17)$$

δn(x,y) can be referred to as the absorption dependent refractive index correction factor that can be expressed as δn(x,y)=$n_o$(x,y)−$n_c$(x,y), where $n_o$(x,y)=n(x,y)+Δn(x, y) is the observed refractive index, and $n_c$(x,y) is the refractive index after correcting for stain variation. Substituting this expression in equation 17 can obtain the final form of the correction model $$n_c(x,y) = n_o(x,y) - \beta(x,y)\alpha(x,y). \quad (18)$$

The absorption-modified specific refraction increment is a constant that can be determined based on techniques described herein.

The refractive index correction factor developed above corrects on the basis of the absorption coefficient. The absorption, however, can change due to two factors: change in the concentration of nucleoproteins and nucleic acids, or change in the hematoxylin concentration. The former is a pathological effect, while the latter is a result of limitations in the clinical protocol. Together they give the measured Δn(x,y). Which effect is corrected for in Δn(x, y) depends on the experiment designed to estimate the absorption-modified specific refraction increment. As the goal is to remove the effect of variations in H&E stain, an experiment was designed where the changes in the nucleoproteins and nuclei acids were kept to a minimum by considering serial sections of a small intestine tissue from a healthy mouse, while the hematoxylin level is varied. However, even though hematoxylin is the dominant nuclear stain and eosin is a counterstain for the cytoplasm, the potential effect of eosin on the nucleus cannot be discarded. Therefore, along with hematoxylin, varying eosin staining levels were also considered.

In this experiment, a small intestine tissue removed from a healthy (wild type) mouse sacrificed at the age of six weeks was used. The small intestine was washed with phosphate buffered saline (PBS) before processing. A segment of PBS washed small intestine was cut and processed with standard histology protocol with 10% formalin fixation, paraffin embedded and cut into 15—4 micron thick—serial sections using a microtome. The tissue sections were mounted onto separate glass slides and deparaffinized.

Figure 35:
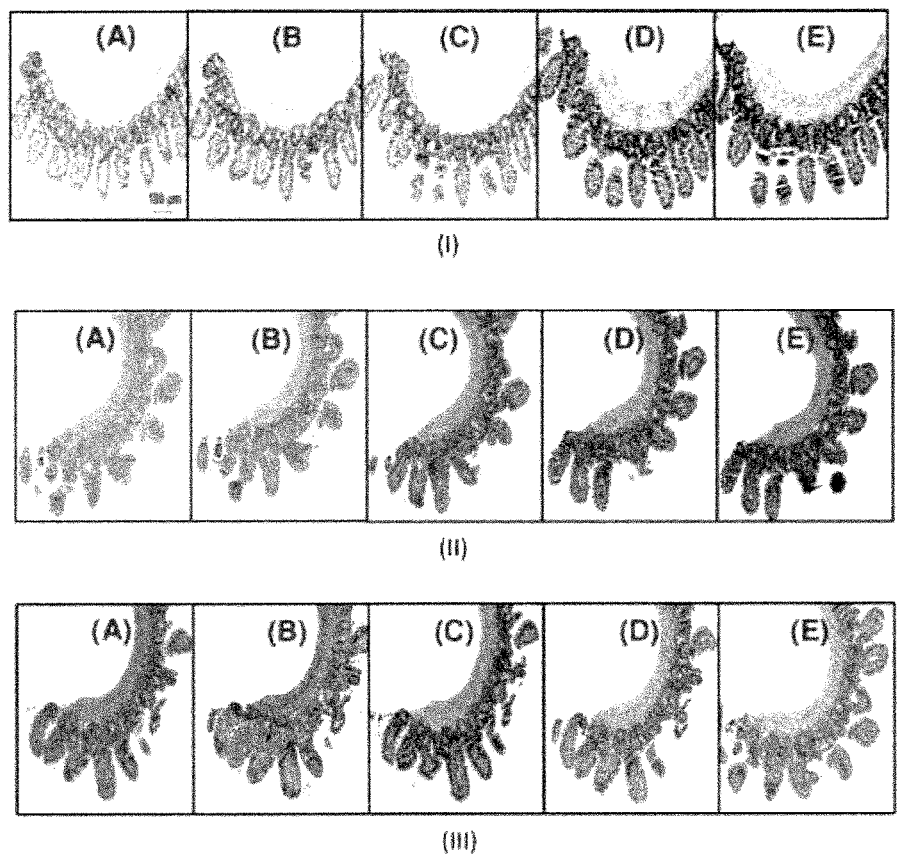
FIG. 35 shows fifteen slides with varying amounts of hematoxylin and eosin (H&E).

The 15 slides were grouped into 3 groups of 5 slides each, and were stained with different amounts of hematoxylin and eosin that cover the plausible range of variation in regular clinical specimens. Specifically, the experiment considered three different eosin levels for the three groups, with five different hematoxylin levels for the five slides within each group. The eosin levels were: no eosin, light eosin and normal eosin, while the hematoxylin levels were: very light hematoxylin, light hematoxylin, normal hematoxylin, dark hematoxylin, and very dark hematoxylin. After this graded staining, the H&E stained slides were coversliped using a mounting media. FIG. 35 shows the fifteen slides. The variations in hematoxylin and eosin are visually discernible. The serial sectioning of the same healthy tissue sample ensured that the variation was not pathological but due to variation in stain uptake.

For each of the 15 slides, reflection- and transmission-mode measurements were taken. The reflection-mode allowed for computation of the observed refractive index, while the transmission-mode allowed for the computation of the absorption coefficient. Both were calculated for the central wavelength of 550 nm.

Figure 36:
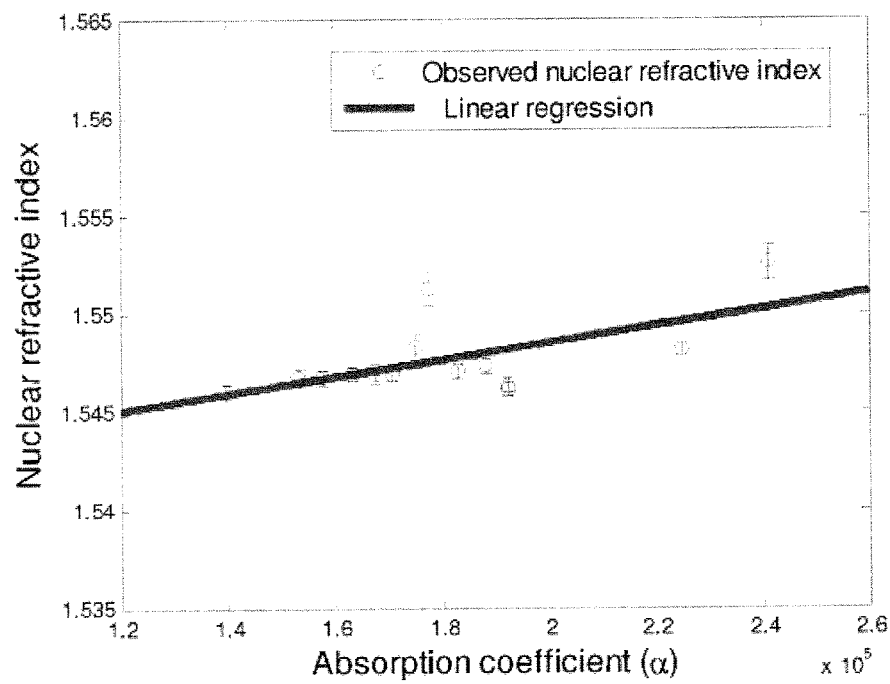
FIG. 36 shows the observed refractive index plotted as a function of the absorption coefficient, along with the regression fit.

From equation 19 it can be seen that the observed refractive index and the absorption coefficient are the dependent and independent variables respectively, while the corrected refractive index and the absorption-modified refraction increment are the model parameters. As is well known, however, cells vary in shape and size. Consequently, computing a constant pixel-wise β image to correct the observed nuclear refractive index image of different cells with different morphologies may not be desired. Therefore, equation 19 can be simplified by correcting for the average nuclear refractive index. This is a reasonable simplification as in most cases the average nuclear refractive index of a cell is of interest. However, it should be noted that this simplification is not a limitation of the method, but was done to simplify the calculations shown herein. The simplification results in $$\langle n_o(x,y) \rangle = \langle n_c(x,y) \rangle + \hat{\beta}\langle \alpha(x,y) \rangle \quad (19)$$

where ⟨ ⟩ denotes the averaging. Therefore, a solution could be obtained by estimating the model parameters $\hat{\beta}$ and ⟨$n_c$(x,y)⟩ from 15 observations. This was an over-determined problem, and using simple linear regression $\hat{\beta}$ and ⟨$n_c$(x,y)⟩ were determined to be 4.3221326E-08 and 1.539922 respectively. FIG. 36 shows the observed refractive index plotted as a function of the absorption coefficient, along with the regression fit. For a significance level of 0.05, the p-value for the model parameters $\hat{\beta}$ and ⟨$n_c$(x, y)⟩ respectively were 0.0223 and 2.088E-27.

Based on the above, an absorption dependent correction method can be applied: measure the average absorption coefficient of a given histology sample and multiply it with the model parameter $\hat{\beta}$. This product is the correction that accounts for variation in stain. Subtracting this absorption dependent correction factor from the observed nuclear refractive index gives the corrected nuclear refractive index.

To study the efficacy of the linear correction model, the method was first validated using a set of test slides obtained in a manner similar to those in the above experiment. Specifically, the test histology slides were obtained from serially sectioning a wild-mouse small-intestine tissue sample and staining the slides with unknown variations in H&E stain. The corresponding measured refractive indices were plotted as a function of the absorption coefficients. The fluctuations in the refractive index were clearly visible. The success of the model is shown by the extent to which, based on the model parameter $\hat{\beta}$ estimated above, these variations are accounted for. The computed correction factors, when applied to the observed refractive indices, gave the corrected refractive indices. Once the variations have been removed, and the nuclear refractive index was constant for varying absorptions. The model was also applied to two more sets of data: mouse model and breast cancer.

Figure 37:
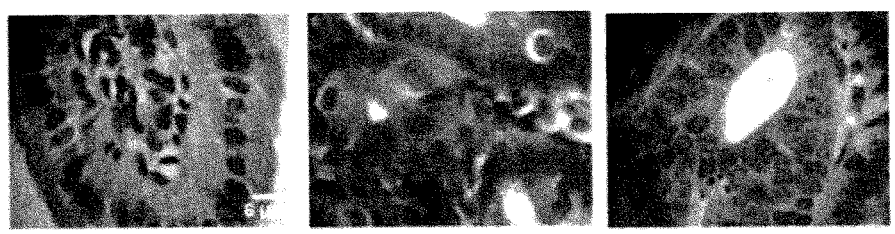
FIG. 37 visually depicts variations in stains in Min mice and breast cancer.
Figure 37:
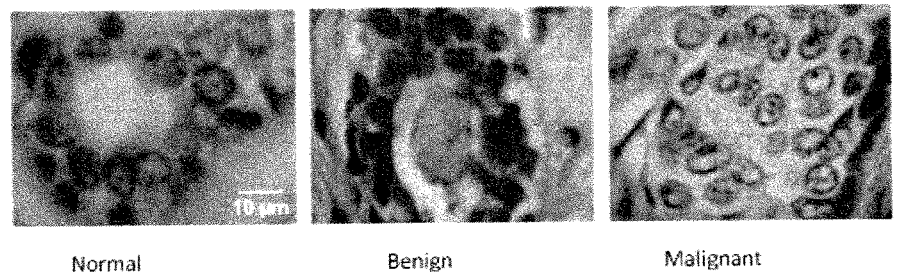
Figures 38A, 38B:
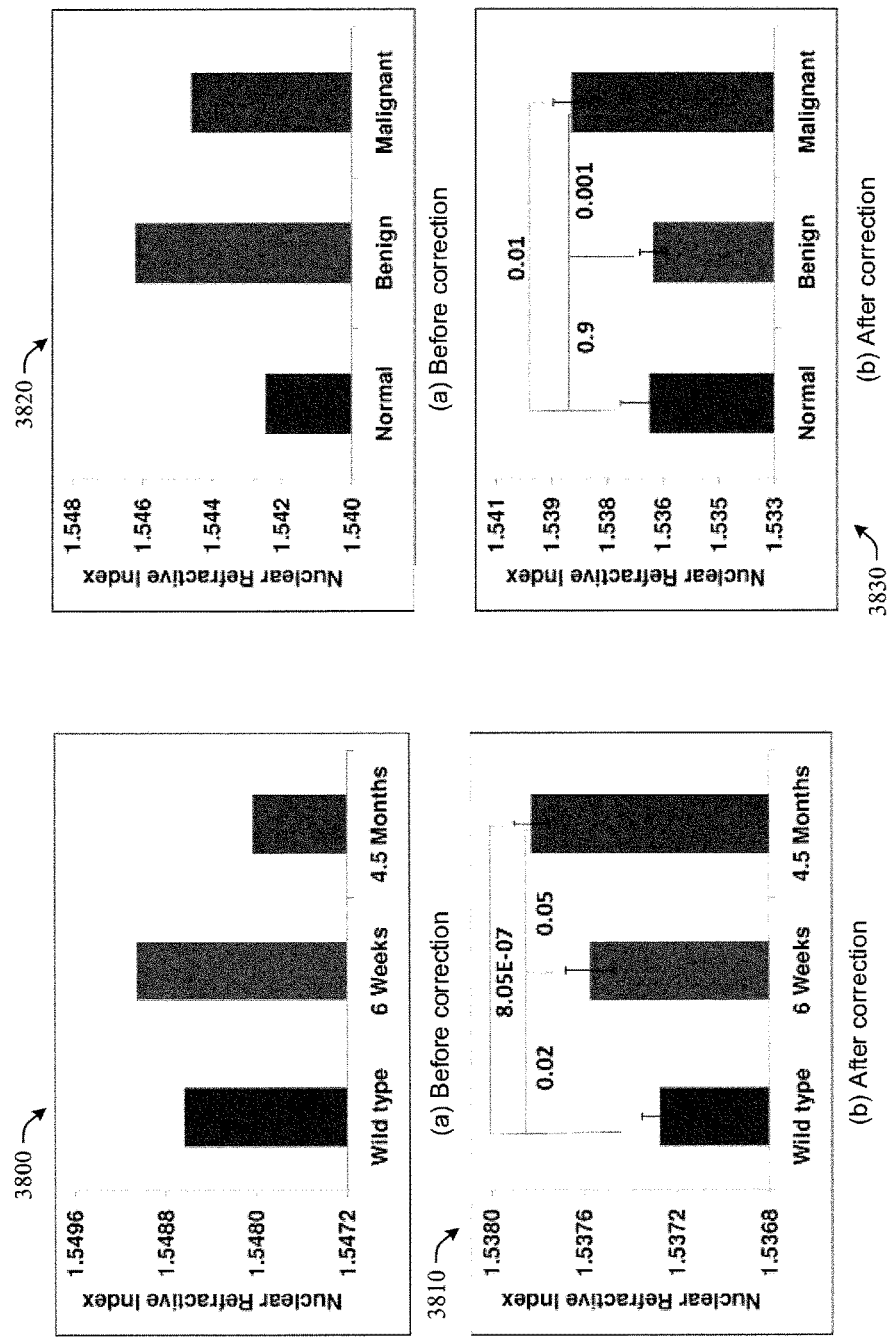
FIG. 38A shows nuclear index variations in intestinal tissue of an animal model.
FIG. 38B shows nuclear index variations in tissue from core needle biopsies of human breast.

Animal models of human diseases are extensively used for basic research in medicine and biology to study the nature of these diseases. The experiment considered the $APC^{Min}$ mouse model that represents the human condition of familial adenomatous polyposis coli (APC) gene that undergoes a germ-line mutation leading to a truncation in the APC protein and spontaneous development of intestinal adenoma. The study considered 60 cells from each of the 3 sets of 3 aged-match mice: 6 week wild-type mice to mimic the healthy condition, and 6 week and 4.5 month $APC^{min}$ mice to mimic two stages of carcinogenesis/dysplasia. The H&E stain histology slides from small intestine epithelial tissue of the mice were obtained following the protocol described above. Due to clinical limitations, there are variations in staining. FIG. 37 visually depicts variations in stains in Min mice on the top row, and breast cancer on the bottom row. The corresponding nuclear refractive index variations are shown in FIG. 38A. From a biological perspective the progression of dysplasia should increase nuclear refractive index due to an increase in nuclear heterogeneity. This pathological trend is not visible in 3800. After applying the correction, however, the pathological trend was clearly visible in 3810 at a significance level of 0.05.

As the next example, breast cancer was considered. Breast cancer is the second leading cause of death in women in United States with an estimated one in eight women predicted to develop it in her lifetime. The preoperative core needle biopsy (CNB) is the standard of care for the initial evaluation of breast lesions in patients with abnormal imaging findings, but it suffers from sampling errors due to sampling the area surrounding the lesion and not the lesion itself. In such a scenario, SL-QPM has shown great potential in identifying dysplasia from the surrounding uninvolved region. Here, the focus was on studying stain variations in three histopathological breast cancer classes: normal (10 patients), benign (10 patients) and malignant (10 patients). Normal refers to cells from healthy patients, benign refers to healthy cells from patients with carcinoma, and malignant refers to cells from malignant tumor.

As in the animal model, clinical staining protocols have variations in H&E staining leading to corresponding variations in nuclear refractive index. This scenario is shown in FIG. 37. It can be seen that the samples from the three classes are stained to different degrees. The corresponding fluctuations in the nuclear refractive index are shown in FIG. 38B. These fluctuations result in an unexpected large difference in the refractive index between normal and benign cells. It is unexpected because both cells being healthy, they would be expected both to have similar nuclear refractive index. Furthermore, the average nuclear heterogeneity of malignant cells captured by the nuclear refractive index was unexpectedly less than that of benign cells. These discrepancies do not follow the expected pathological trend, as shown in 3820. After correction, however, it can be seen in 3830 that the difference between the nuclear refractive indices of normal and benign cells is not statistically significant at a significance level of 0.05, corroborating the truth that both are healthy cells. Moreover, the difference between their nuclear refractive indices and that of the malignant cells was statistically significant with p-values of less than 0.05. Thus it can be seen that the above-described method for correcting variations in stain does indeed remove the effect of stain while retaining the pathological changes.

Figure 39:
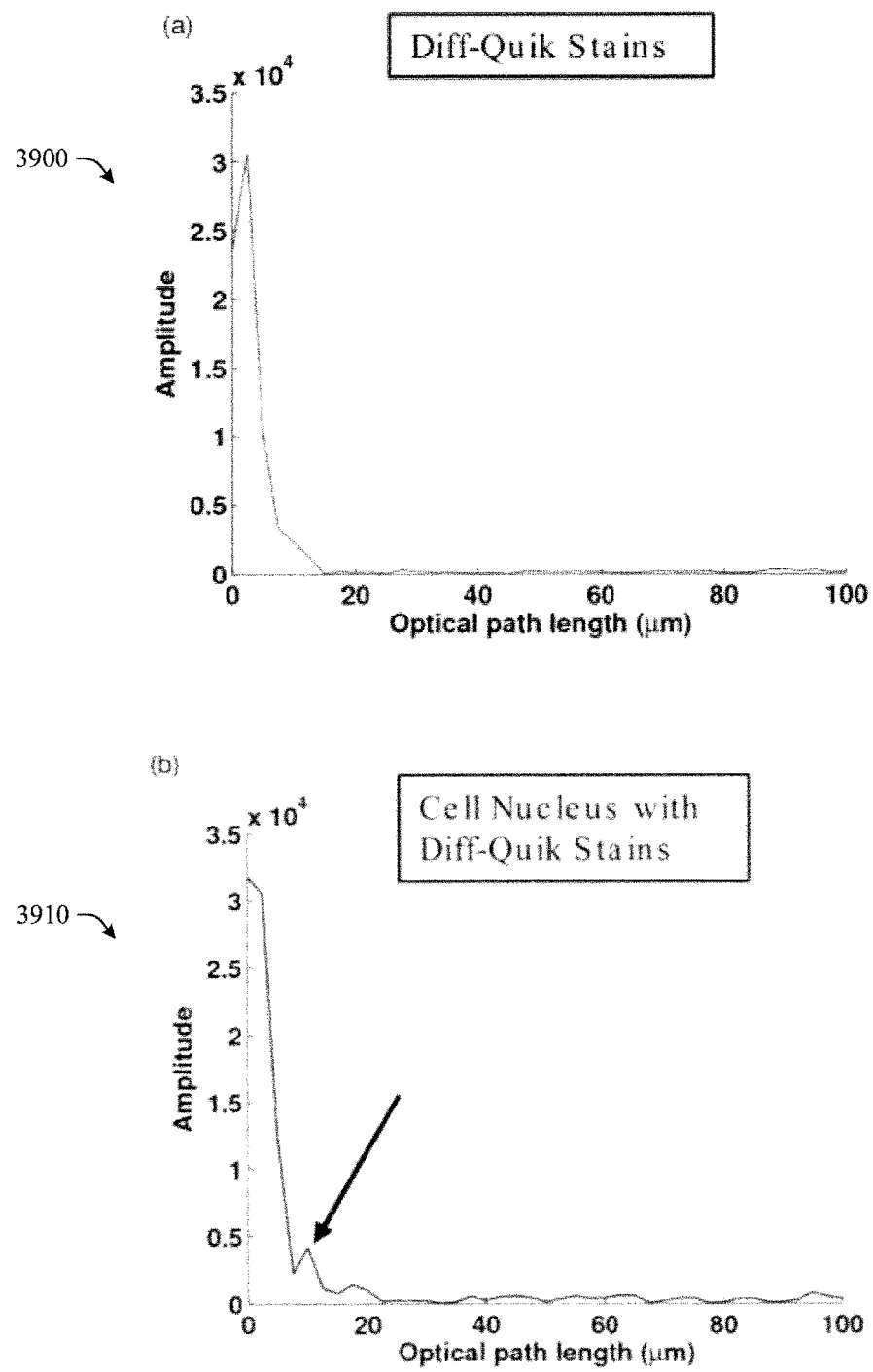
FIG. 39 shows results indicating that the selected optical path length of interest is not affected by the absorption profile of the Diff-Quik staining solution.

In another experiment discussed herein, further results were obtained regarding the effects of staining. FIG. 39 shows results indicating that the selected optical path length of interest is not affected by the absorption profile of the Diff-Quik staining solution. Fourier transformed spectrum |F(OPL)| of the original backscattering spectrum I(x, y, k) from the Diff-Quik staining solution at 3900 and a cell nucleus stained with Diff-Quik stains at 3910. The prominent peak at the low-spatial-frequency component of |F(OPL)| came from the absorption profile of the Diff-Quik staining solution. Additionally, the |F(OPL)| from the Diff-Quik-stained cell nucleus has a distinctly different peak, corresponding to the optical path length of the cell nucleus (as indicated by the black arrow).

Depth-Resolved Nanoscale Structural Changes in Regulated Cell Proliferation and Chromatin Decondensation A further study involved depth-resolved spatial-domain low-coherence quantitative phase microscopy (SL-QPM), an approach that utilized coherence gating to construct a depth-resolved structural feature vector quantifying sub-resolution axial structural changes at different optical depths within the sample. As discussed below, this feature vector was independent of sample thickness variation, and identified depth-resolved three-dimensional nanoscale structural changes in clinically prepared samples. Numerical simulations and experimental validation discussed below demonstrated the feasibility of the approach. Experiments were also performed using unstained cells to investigate the nanoscale structural changes in regulated cell proliferation through cell cycle and chromatin decondensation induced by histone acetylation.

The ability to identify structural changes in cells and tissue, especially at the nanometer scale during disease processes (e.g., cell differentiation, proliferation, gene expression, malignant transformation) has important implications in biomedical research and clinical diagnosis. Cellular nanoscale structural properties have received increasing attention as promising markers for pre-cancerous and cancerous cells. Recent studies suggest that nanoscale structural changes occur early in carcinogenesis and precede microscopically detectable cytological abnormalities. The analysis of nanoscale structural properties has shown great promise in early diagnosis and cancer risk assessment for different types of cancers, as discussed herein. Towards this end, interferometric techniques discussed herein—e.g., spatial-domain low-coherence quantitative phase microscopy (SL-QPM)—have been developed and show potential to detect malignancy at a higher sensitivity than conventional pathology, and to quantify cancer risk.

SL-QPM can uses a reflection-mode common-path low-coherence interferometric setup equipped with a broadband light source and spectroscopic detection. It can quantify changes in the optical path length (OPL), with nano scale sensitivity, to capture the sub-resolution structural changes within the cell nucleus. The OPL can be obtained by measuring the phase of the Fourier-transformed spectral interference signal at a specific optical depth of interest. The reflection-mode common-path setup suppresses the common-mode phase noise, while the spatial low-coherence of the light source prevents back-scattered light from one location within the sample from coherently combining with back-scattered light from another displaced location, resulting in the suppression of coherence-dependent speckle noise. A broadband light source can be used for improved axial resolution.

Similar interferometric phase microscopy techniques have been successfully used to measure transient structural changes in nerve cells, perform real-time molecular detection, and measure cellular dynamics. These techniques detect the sub-resolution change in OPL at a specific depth of interest corresponding to a distinct physical interface of interest with a strong refractive-index mismatch within the sample. As with these similar techniques, the implicit coherence gating allows the rejection of contributions to phase from locations outside the coherence length. Although these techniques have proven to be very valuable in tracking dynamic structural changes, their use in analyzing the nanoscale structural properties of static clinical specimens at different disease stages has been limited. If phase microscopy can be used to reliably analyze nanoscale cellular structural properties directly on clinically prepared human cell (cytology) or tissue (histology) samples, it could have significant implications in both basic understanding of structural alterations during disease processes and clinical disease diagnosis. According to the standard clinical protocol, cells or tissue are first fixed (e.g., using formalin), and then embedded in paraffin to prepare the cell or tissue block. For structural analysis, thin sections—a few microns thick—are cut from a cell or tissue block using a microtome, mounted on a microscope slide, deparaffinized and finally cover-slipped using a mounting medium. One of the biggest challenges in using phase microscopy for structural analysis of such clinically-prepared cell and tissue samples is decoupling the variation in section thickness from the actual structural changes within the cell or tissue.

However, as described herein, SL-QPM can be used to provide depth-resolved quantification of internal structural changes within the cell nucleus with regulated cell proliferation and chromatin decondensation—directly using clinically prepared unstained cell samples—where the structural changes associated with these biological processes can be decoupled from those due to sample thickness variations. Both depth-resolved quantification and removal of the effect of thickness variation can be achieved by exploiting the coherence gating implicit in the spectral-domain interferometry. The resulting thickness-independent depth-resolved structural feature vector can capture the sub-resolution structural changes at different, but fixed sample depths inside the sample.

As discussed below, an SL-QPM optical setup was used to implement the approach. The underlying theory is presented first, followed by numerical simulations that show the independence of the depth-resolved structural feature vector from variation in sample thickness, study the effect of noise on the feature vector, and illustrate why the approach has the ability to capture depth-resolved structural changes. After that, experimental results are presented that validate the use of implicit coherence gating to obtain the depth-resolved structural features that are independent of section thickness. Then results from using clinically prepared cell blocks show the depth-resolved nanoscale structural alterations within the cell nucleus during the regulation of cell proliferation through cell cycle and chromatin decondensation induced by histone acetylation with altered chromatin density and structure. These experimental results indicate that the depth-resolved approach has direct applicability in analyzing samples prepared using standard clinical protocol, and can provide new insights into the structural transformation of cell nuclei during cell proliferation and chromatin decondensation.

Depth-Resolved Structural Characterization

The experimental setup of SL-QPM has been described above. In brief, a collimated broadband light (e.g., from a Xenon-arc lamp) can be focused onto the sample by an objective (e.g., NA=0.4, as used in experimental results discussed herein). The sample itself forms a reflection-mode low-coherence common-path interferometry configuration. The reference and back-scattered waves from the sample can be collected and projected (e.g., by a tube lens) onto the slit of an imaging spectrograph coupled to the CCD camera mounted on a scanning stage, or can be collected via an AOTF, as discussed in connection with system 500, above. The temporal coherence length of the example system used to obtain results discussed below was 1.225 μm and the probing depth of the system was estimated to be 79 μm.

Figure 40:
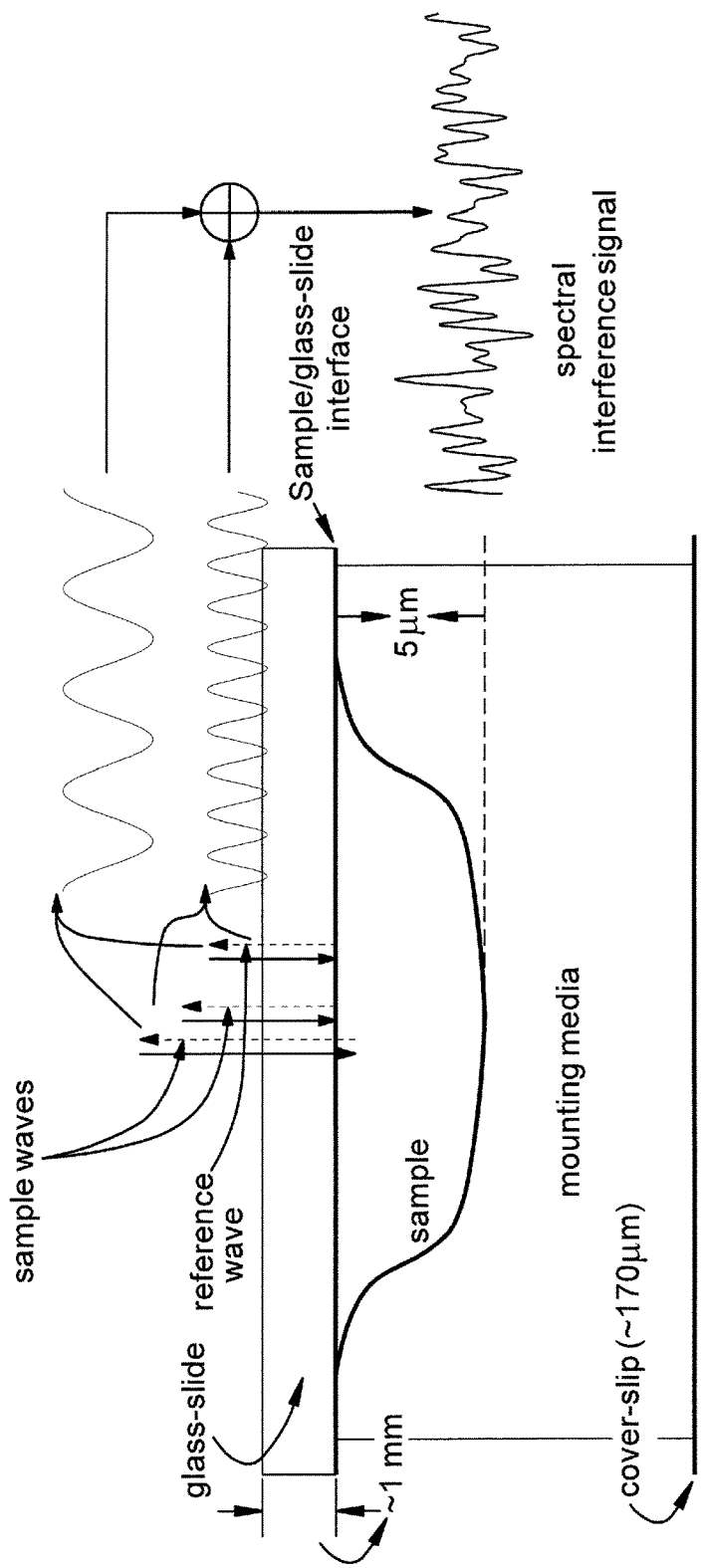
FIG. 40 illustrates a reflection-mode common-path interferometry setup of experiments discussed herein based on a clinically prepared glass slide.

The sample consisted of an unstained cell section with 5 μm thickness obtained by sectioning a paraffin-embedded cell block with a microtome, mounted on a coated glass-slide (80T/20R, although other ratios can be used in various embodiments), and then cover-slipped using mounting medium with a refractive index of 1.50, as seen in FIG. 40, which illustrates the reflection-mode common-path interferometry setup of these experiments based on a clinically prepared glass slide. The setup dimensions and the axial refractive index profile have been exaggerated for clarity. The coated glass-slide on the top of the sample was approximately a millimeter thick. However, due to the small depth of field (~4 μm) and limited probing depth of the system, when the incident light was focused onto the sample, the reference wave was generated by the reflection at the sample and the coated glass-slide interface. The reference wave was enhanced by the reflection coating on the glass slide. As the refractive index mismatch between the sample and the mounting medium was small, the sample wave consisting of backscattered waves from the heterogeneous components inside the scattering sample was not dominated by the reflection from the sample-mounting medium interface. The detected spectral signal can be written as in equation 1, above (reproduced here):

$$P(k) = S(k)\left[r_r^2 + \int_0^z r_s^2(z')dz' + 2\int_0^z r_s(z')r_r\cos(2kn(z')z')dz'\right], \quad (1)$$

where $S(k)$ is the power spectrum of the source, $r_r$ is the reflection coefficient of the reference wave, $r_s(z)$ is the scattering coefficient of the sample at depth z, Z is the total sample thickness and $n(z)$ is the refractive index distribution along the axial z-direction and $k=2\pi/\lambda$ is the wavenumber, with $\lambda$ being the wavelength.

In the context of spectral-domain interferometry, Fercher et al. showed that under the Born approximation and the far-field assumption, the 3D spatial frequency corresponding to a monochromatic wave, after being scattered from the object of interest, is given by $K=(k_s-k_i)/2\pi$. For the incident wave at normal illumination and collection, the back-scattered components are restricted to the axial z-direction, and the spatial frequency reduces to $$K = \left(\frac{k}{\pi}\right)z,$$

where z is the unit vector in the positive z-direction in frequency space.

Therefore, equation 1 can be re-written as equation 20, $$P(K) = S\left(\frac{K}{2}\right)\left[R_r + R_s + 2\int_0^z r_s(z')r_r\cos\left(4\pi\frac{K}{2}n(z')z'\right)dz'\right], \quad (20)$$

where $R_r = r_r^2$ and $R_s = \int_0^z r_s^2(z')dz$. The Fourier inverse of equation 20 results in equation 21:

$$p(z_{opl}) = 2\Gamma * \left[(R_r + R_s)\delta(0) + 2r_r\mathcal{F}^{-1}\left(\int_0^z r_s(z')\cos\left(4\pi\frac{K}{2}n(z')z'\right)dz'\right)\right], \quad (21)$$

which is a convolution of the source correlation function F with the superposition of the reference wave and the back-scattered sample wave. As a result, the amplitude and the phase of the Fourier-transformed signal at any given optical depth of interest has contributions only from the back-scattered waves within the coherence length around the given optical depth of interest. Choma et al. showed that the phase of the Fourier transform of the spectral signal with respect to a fixed optical-depth location captures the sub-resolution change in OPL at that location. This sub-resolution change in OPL can be calculated using equation 3 (reproduced here), $$\delta p(z_{opl}) = \frac{\lambda_0}{2\pi}\arctan\left(\frac{\text{Im}(p(z_{opl}))}{\text{Re}(p(z_{opl}))}\right) \quad (3)$$

where $z_{opl}$ is the fixed optical depth location, and Im and Re denote the imaginary and real parts of the complex convolution $p(z_{opl})$, respectively. Note that the factor of 2 accounts for the double OPL due to the reflection configuration.

Figure 41:
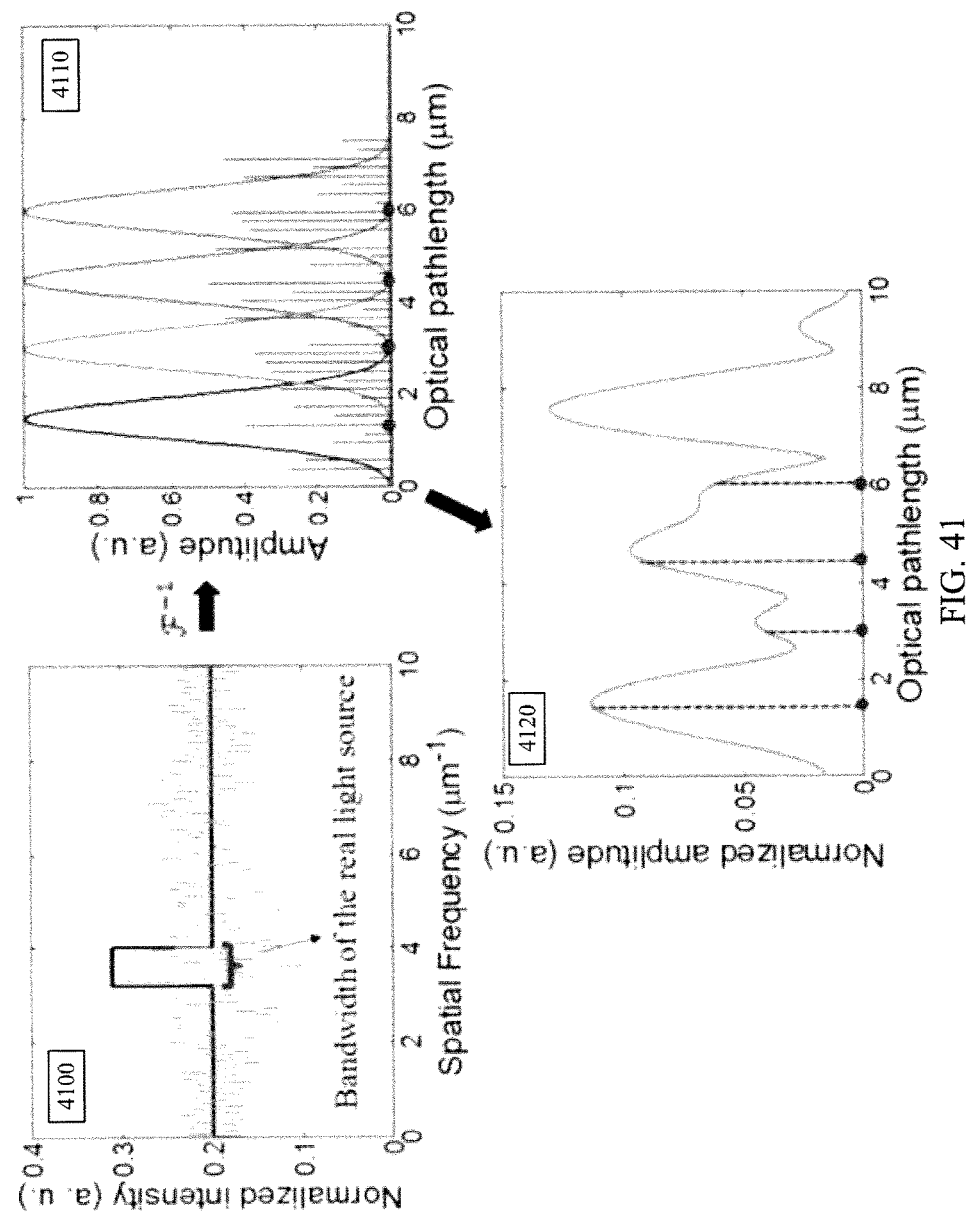
FIG. 41 illustrates depth-resolved SL-QPM via coherence gating at fixed depth locations.

For conventional spectral-domain interferometry approaches, the implicit coherence gating has been used to extract the value of sp at a peak location that corresponds to a distinct physical interface of interest (due to a strong refractive index mismatch within the sample). In contrast to this traditional approach, aspects of the subject innovation can instead exploit the implicit coherence gating by obtaining δp at fixed optical depths within the samples that have small refractive index gradient (no strong interfaces), thereby removing the effect of sample thickness (as discussed below). The fixed optical depth locations can be chosen such that the distance between them is at least one coherence length of the correlation function. FIG. 41 illustrates this approach, showing depth-resolved SL-QPM via coherence gating at fixed depth locations (shown as dots). A representative spectral interference signal from a given scattering object for an ideal light source with nearly infinite bandwidth is shown in 4100. The corresponding OPL profile, obtained by Fourier transforming this spectral interference signal, represents the true OPL profile of the scattering object, and is depicted by the distinct stem-plot in 4110. However, due to the limited spectral bandwidth of the light source, only a limited range of the spatial frequencies from the scattering object are captured, as visualized through the windowing function in 4100. As a result, the Fourier relation between spatial frequency and OPL manifests as a convolution between the source correlation function (i.e., Fourier transform of the power spectral density of the source) and the actual OPL profile of the scattering object derived from an ideal light source with nearly infinite bandwidth. The resulting coherence gating implicit in this convolution is illustrated in 4110. The final OPL profile using a light source with a limited bandwidth is shown in 4120, with the original distinct peaks in the true OPL profile significantly broadened.

Note that in clinically prepared samples, there is no predominant physical interface with a significant refractive index mismatch. As a result, the OPL profile has contributions from the backscattering signals from all depths within the sample, and does not exhibit a dominant peak corresponding to a specific physical interface. Therefore, for clinically prepared samples, instead of identifying structural changes at any specific physical interface, a more cogent strategy is to identify structural changes at fixed optical-depth locations in such a way that the source correlation functions around these optical depths cover the axial sample depth-range of interest. Towards this end, in aspects, the subject innovation can employ a technique wherein the optical-depth locations are first fixed such that they are separated by at least one coherence length. As a result, the δp value at each of these locations (indicated by the dots in 4110 and 4120) captures the internal structural change within the coherence-gated optical section around each optical depth. Next, depending on the sample thickness (discussed in greater detail below), a sufficient number of optical depth-locations can be chosen to ensure that the entire sample depth-range of interest is covered. The δp values from these optical-depth locations then form the elements of a depth-resolved feature vector that characterizes the sub-resolution structural alterations within the sample. Note that due to the coherence-length separation, the elements of the structural feature vector—the δp values—are independent of each other. A necessary condition for the depth-resolved feature vector to be valid is that the signal strength at the selected locations is above the noise floor. As discussed below, systems and methods of the subject innovation satisfy this condition.

Effect of Sample Thickness

Figure 42:
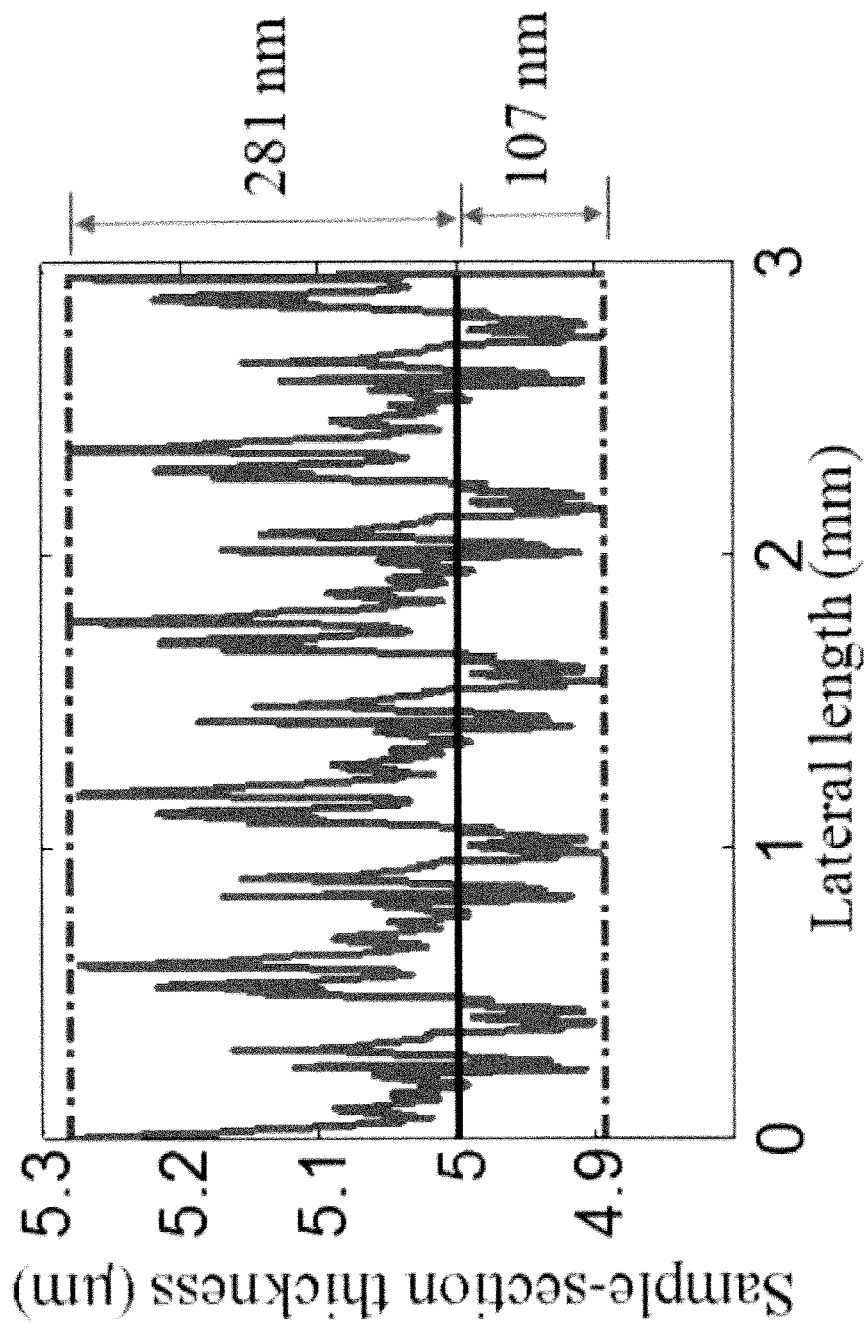
FIG. 42 illustrates a representative thickness profile of a sample section measured using a Dektak profilometer.

The actual sample thickness for a specified value is controlled by the precision of the microtome, a tool commonly used to section the sample into thin slices of specified thickness for clinical cell or tissue specimens. Due to imperfect precision in microtome sectioning, some variation in the thickness of the sectioned sample is inevitable, as shown in FIG. 42, illustrating a representative thickness profile of a sample section measured using Dektak profilometer, which has a resolution of 5 Å. If the location corresponding to the physical interface at the sample and mounting medium (within the OPL profile) is used, the measured δp at this interface will significantly depend on the variation in sample thickness. However, if a fixed optical depth location inside the sample is chosen such that the variation in section thickness of the sample is outside the coherence length around this chosen location, then δp at this fixed optical depth location, and all the other preceding locations, will not be affected by the variations in sample thickness. Using ten samples, it was empirically determined that the maximum deviation in sample thickness from the chosen section thickness of 5 µm was less than 500 nm, as visually exemplified in FIG. 42.

Figure 43:
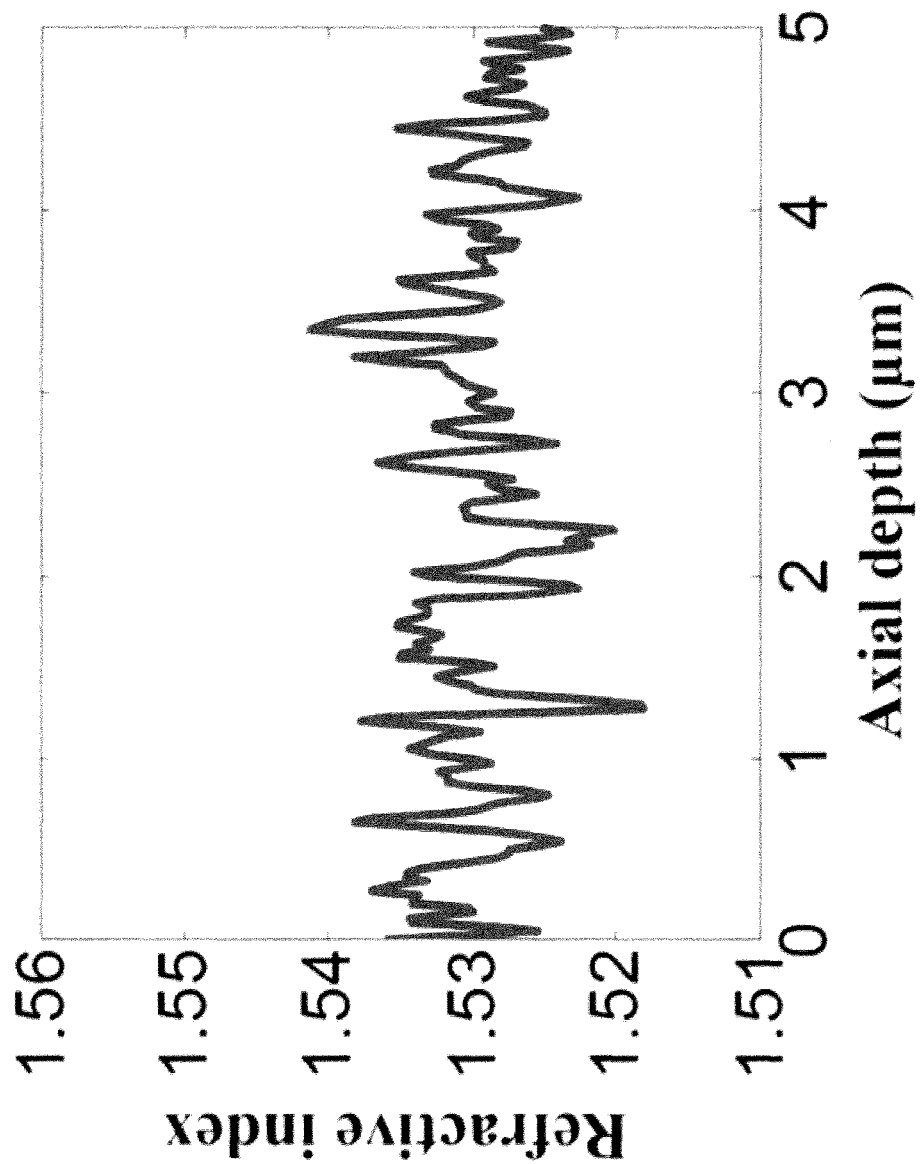
FIG. 43 illustrates a representative axial refractive index profile of the scattering sample.

With this experimentally determined bound on sample thickness variation, numerical simulations were performed to illustrate the independence of the depth-resolved structural feature vector from sample thickness. As shown in FIG. 43, illustrating a representative axial refractive index profile of the scattering sample, a one-dimensional (1D) axial refractive index profile n(z) was constructed with 5 µm sample thickness with a step-size of 25 nm. This profile was generated using a Gaussian random field (GRF). Each value of n(z) was a Gaussian random variable with mean $n_0 = \langle n(z) \rangle$ and standard deviation $\langle \Delta n \rangle = \sqrt{\langle [n(z)-n_0]^2 \rangle}$. The angular brackets denote the ensemble expectation. The Gaussian function was used as the two-point correlation function:

$$C_n(z) = \exp\left(\frac{-z^2}{\left(\frac{l_c}{2}\right)^2}\right),$$

where $I_c$ is the spatial correlation length of refractive index representing the length scale over which the spatial correlation decreases to a negligible level. The model parameters were chosen to be consistent with the specifications of the experimental condition. Specifically, the average refractive index of the fixed tissue section no was assumed to be 1.53 (the dehydrated cells and tissue were reported to have a refractive index of 1.50 to 1.55), with the standard deviation $\langle \Delta n \rangle$ and the correlation length $I_c$ of the spatial variation of refractive index being 0.002 and 50 nm, respectively. This 1D profile has been previously used to model the refractive index profile of biological samples. Following the common-mode reflection configuration of FIG. 40, the reflection from the sample and the glass-slide interface acts as the reference wave. The refractive index of the glass-slide was assumed to be 1.515. Collimated light from a broadband source (498 nm-625 nm) was normally incident on the modeled scattering object, and the spectral-domain interference signal resulting from the superposition of the reference and the back-scattered waves was collected. The back-scattered waves from the sample were generated by modeling the axial refractive index profile as a layered media, and by using the wave-transfer matrix and scattering matrix formalism to describe the reflection from within the sample.

Figure 44:
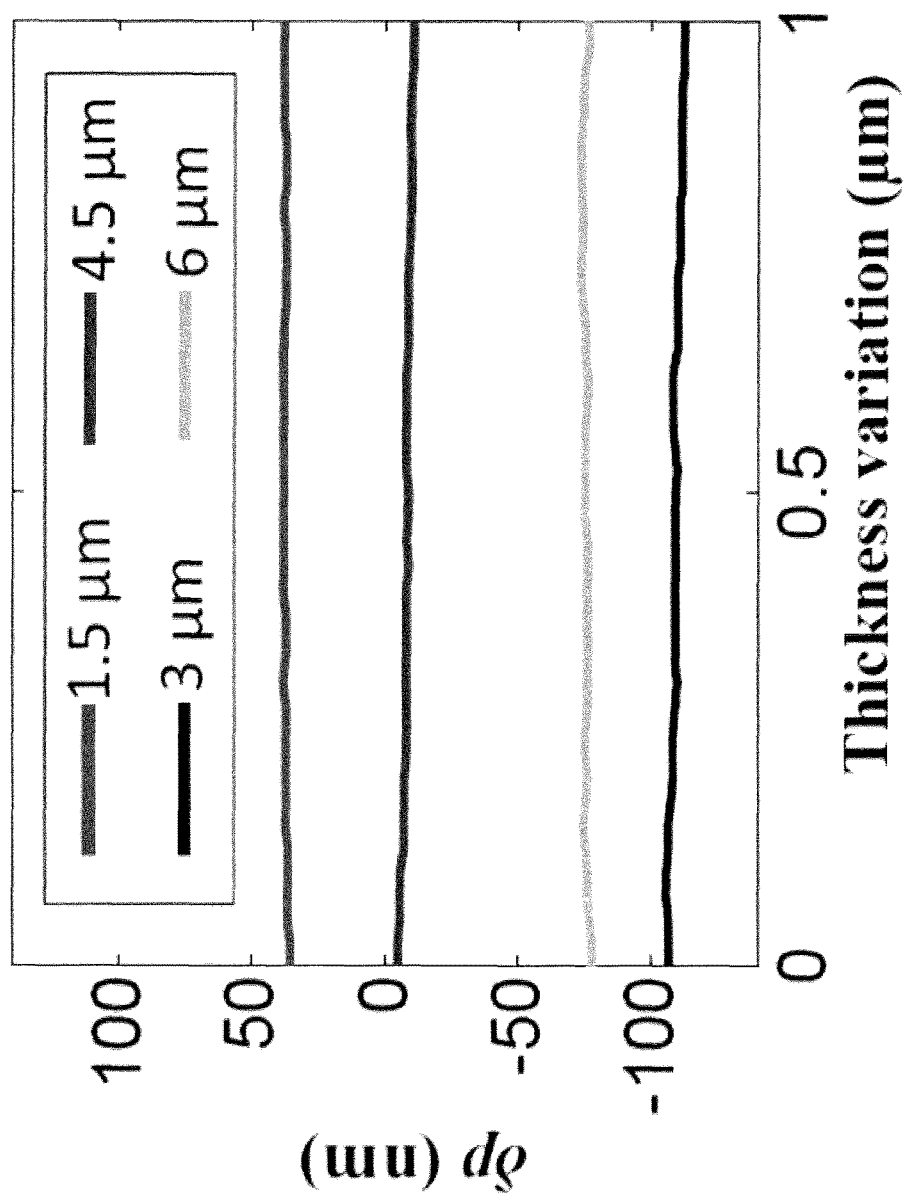
FIG. 44 illustrates variation in the sub-resolution change in optical path length as a function of variation in sample thickness.

For the broadband light source considered, and using the relationship between spatial frequency, wave-vector, and wavelength explained above, the spatial-frequency bandwidth was 0.816 1 p/µm with the resulting coherence length being 1.225 µm. Therefore, the fixed optical-depth locations of 1.5 µm, 3 µm, 4.5 µm, and 6 µm were used, which, for a mean refractive index of 1.53, corresponded to the physical-depth locations of 0.98 µm, 1.96 µm, 2.94 µm, and 3.92 µm respectively. The average physical thickness of the scattering sample was 5 µm, corresponding to the mean optical thickness of 7.65 µm. A variation in sample thickness of ±500 nm translated into the change in optical thickness of ±765 nm. Consequently, the optical thickness of the sample varied between 6.8850 µm and 8.4150 µm. Due to the coherence gating, the sub-resolution structural change in OPL, δp, at the optical depth location of 6 µm carried the structural information of the scattering sample from the depth range of 6±0.6125 µm, which lay well outside the variation in optical thickness of the sample (6.8850–8.4150 µm). Therefore, it was expected that this variation would not affect the δp values at the fixed optical-depth locations of 1.5 µm, 3 µm, 4.5 µm, and 6 µm. This expectation was confirmed by the simulation results. FIG. 44, illustrating variation in δp as a function of variation in sample thickness, shows that δp values remain stable—with maximum deviation of 2 nm—for the four optical-depth locations as the sample-section thickness changes from 4.5 µm to 5.5 µm.

Effect of Noise

The use of depth-resolved feature-vector to characterize structural change requires that the δp values for the four optical-depth locations are not affected by noise, that is, there is no variation in δp values over repeated measurements of the same sample. This requirement is essential to ensure consistent and repeatable performance without adversely affecting the system sensitivity. Toward this end, simulation-based stability performance of feature-vector measurements as a function of SNR for shot-noise limited detection is presented. For this type of detection, the noise photons per detector are, $$N_{noise} = \sqrt{\frac{\eta P_{ref} \tau}{h\nu} \frac{2}{N}} \quad (22)$$

where, η is the quantum efficiency of the detector, τ is acquisition time, hv is the photon quantum energy, and N is the number of detectors. The signal photons per detector are $$N_{signal} = \frac{2\eta\sqrt{P_{sig}P-ref}\,\tau}{h\nu}\frac{2}{N} \quad (23)$$

Accounting for the fact that Fourier transform results in the coherent integration of the signal and the incoherent integration of noise, the system signal-to-noise ratio (SNR) is $$SNR = 10\log_{10}\frac{4\eta P_{sig}\tau}{h\nu}\frac{2}{N}\,dB \quad (24)$$

Figure 45:
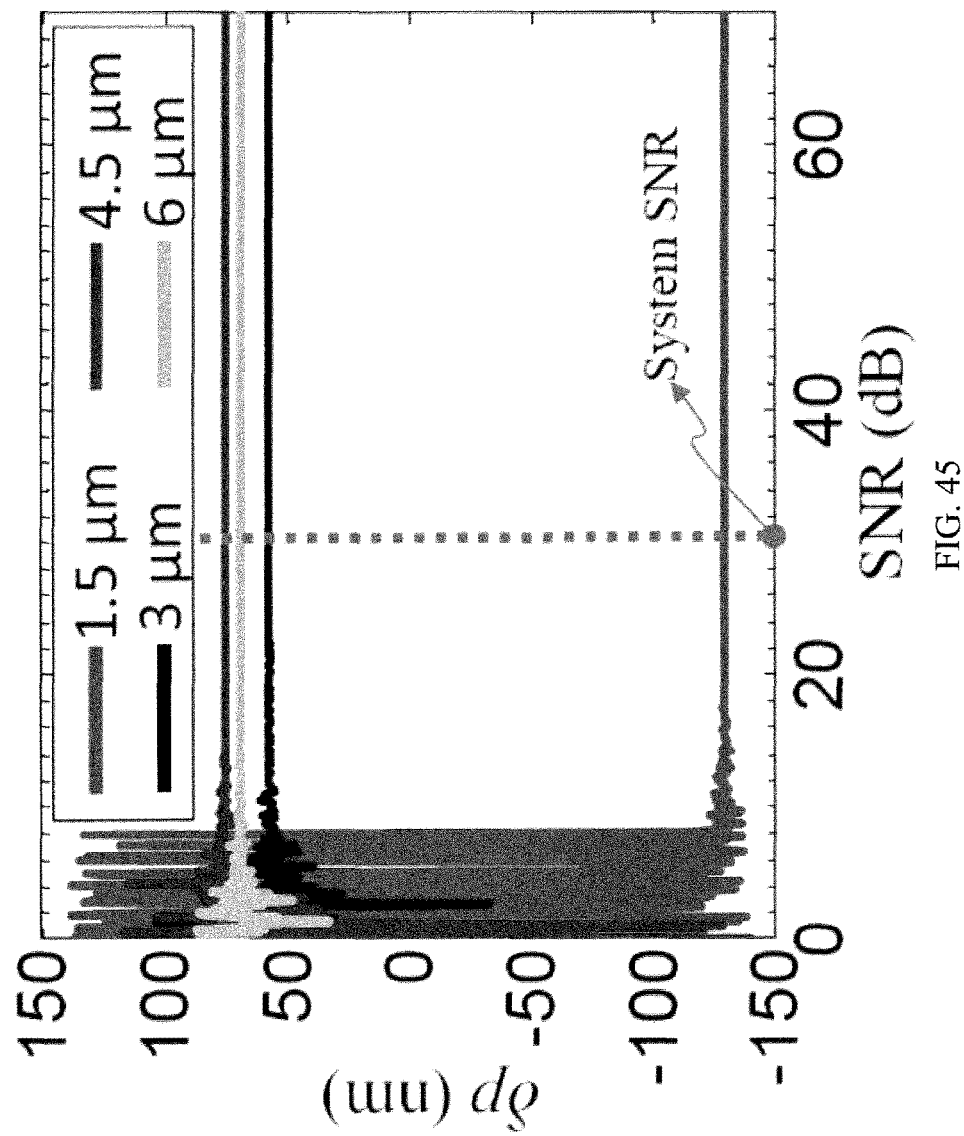
FIG. 45 illustrates the sub-resolution in change in OPL ($\delta p$) as a function of SNR for the same refractive index profile at fixed optical-depth locations of 1.5 µm, 3 µm, 4.5 µm and 6 µm.

For the simulation a fixed refractive index profile was considered that was used to generate the δp values at the four optical-depth locations for changing SNR. The simulation was performed using the method outlined above. Shot noise, which follows Poisson statistics, was simulated through a Gaussian process with white spectrum, whose mean is zero, and standard deviation is proportional to $\sqrt{P_{ref}}$. Under experimental conditions, with sufficiently large number of photons collected by the detector, it was reasonable to simulate a Poisson distribution through a Gaussian distribution. FIG. 45—illustrating the sub-resolution in change in OPL (δp) as a function of SNR for the same refractive index profile at fixed optical-depth locations of 1.5 µm, 3 µm, 4.5 µm and 6 µm—shows the δp values at the four optical-depth locations for changing SNR. As can be seen, for low SNR all four δp values fluctuate wildly. However, as SNR increased the values converged to a stable value, with variation in δp of less than ±0.1 nm for SNR greater than 22 dB. FIG. 45 also indicates the SNR of 31 dB for the system, which is well within the stable region.

Figure 46:
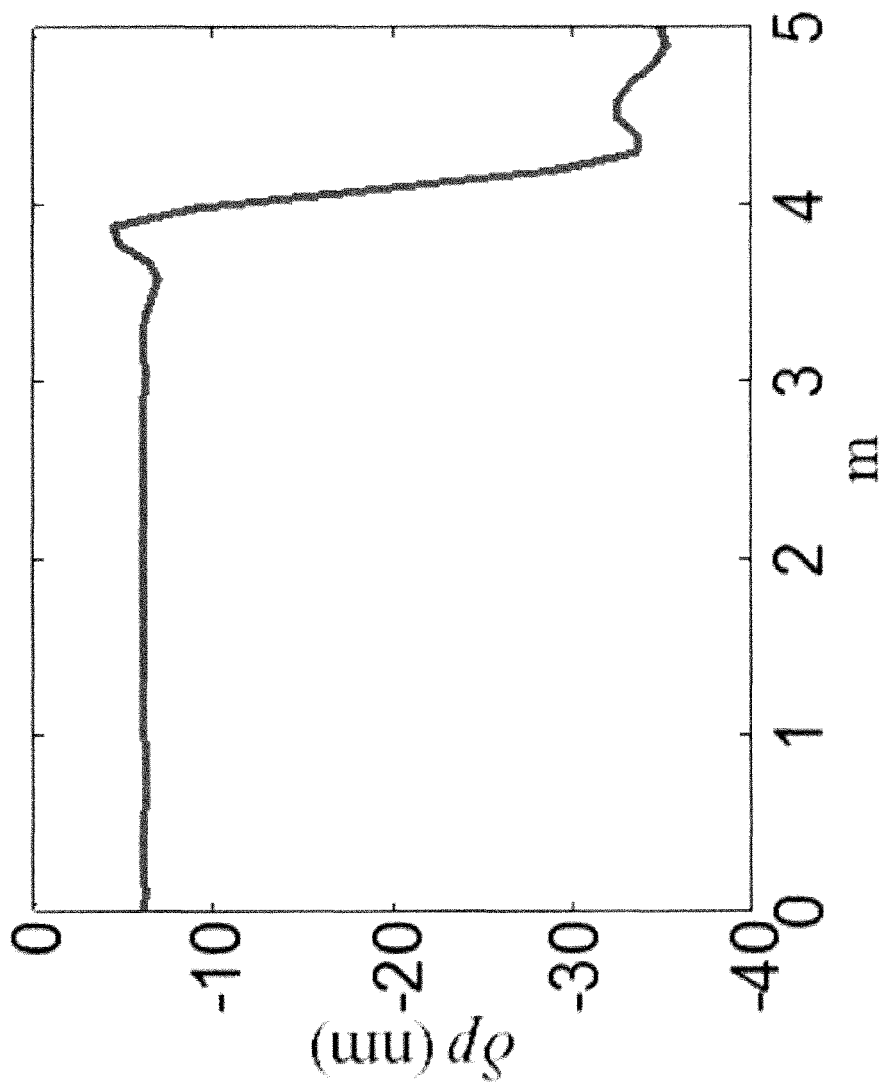
FIG. 46 illustrates the $\delta p$ value at the optical depth location of 1.5 µm for changing refractive index mismatch that occurred at the optical depth location of 6.5 µm, quantified as a multiple of the standard deviation.

Apart from the system SNR, the presence of a distinct interface (strong refractive index mismatch) along the refractive index profile has the potential to adversely affect the δp values at different depth locations despite the coherence gating. The coherence gating was implemented implicitly by performing a Fourier transform. The resulting correlation function that served as the coherence gate did not taper-off smoothly, but instead had side lobes (even after using smoothing windows such as the Hanning window). Consequently, the energy from a strong reflected wave can leak into the correlation functions at different depths, thereby affecting the δp values at those depths. FIG. 46 illustrates this scenario, showing the δp value at the optical depth location of 1.5 μm for changing refractive index mismatch that occurred at the optical depth location of 6.5 μm. The mismatch is quantified as a multiple (m) of the standard deviation $\langle \Delta n \rangle$ of the refractive index profile. As can be seen, for a large mismatch of more than three times $\langle \Delta n \rangle$, the energy from the strong refractive index mismatch leaks into the correlation function at 1.5 μm, affecting its δp value. Therefore, the approach is only applicable to samples whose refractive index profile does not have very strong refractive index mismatch.

Contribution of Structural Characteristics to δp

Figure 47:
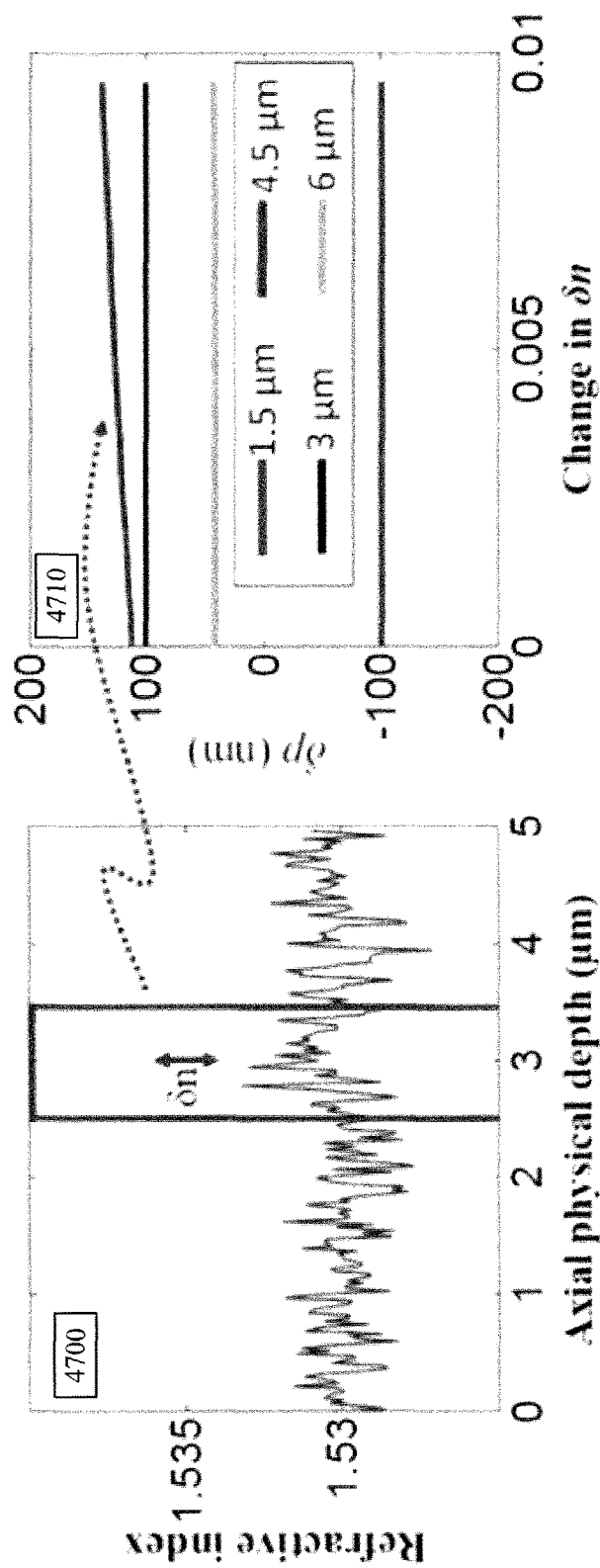
FIG. 47 illustrates the effect of local change in mean refractive index of the axial refractive index profile that was generated from a GRF model with a fixed correlation length.

The depth-resolved δp values capture the sub-resolution change in OPL at the specified optical-depth locations. This sub-resolution change in OPL quantifies the structural change within the coherence-gated optical section around each of the fixed optical-depth locations. To exemplify this concept, numerical simulations were performed using the GRF model presented above to investigate the effect of two statistical parameters that characterize the structural properties of the sample: the average magnitude of the local mean refractive index δn, and the local spatial correlation length of refractive index profile $l_c$. The former characterizes the change in local density of macromolecules, while the latter is a statistical measure of the spatial scale of the refractive-index variation (e.g., the presence of larger macromolecules increases $l_c$). Using these two parameters, the conditions that individually isolate the effects of δn and $l_c$ on the measured sub-resolution structural change were simulated. FIG. 47 shows the effect of local change in mean refractive index of the axial refractive index profile that was generated from a GRF model with a fixed correlation length. As shown in 4700, the mean refractive index within the region delineated by the rectangular-box—physical depth range of 2.5 μm to 3.5 μm approximately corresponding to the optical depth range of 3.9 μm to 5.3 μm—was varied from 0 to 0.01.

Figure 48:
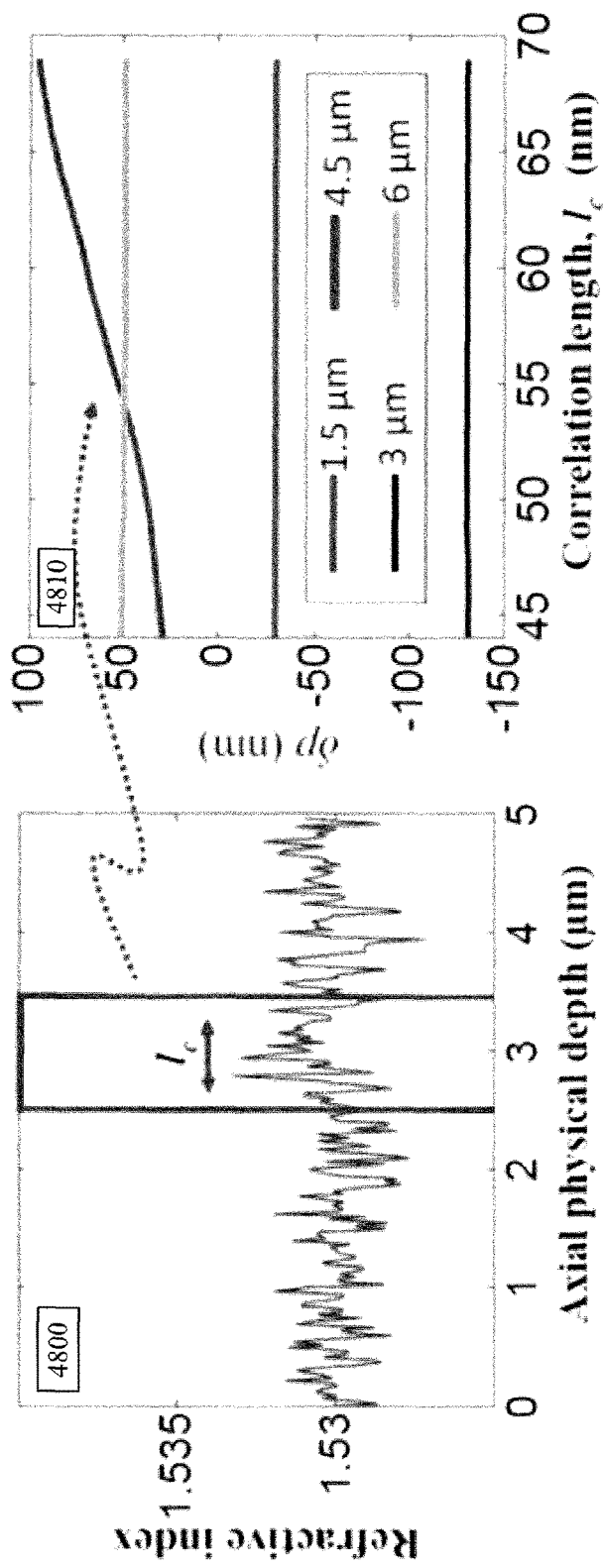
FIG. 48 illustrates the relationship between $\delta p$ and the profile correlation length, $\delta l$.

Image 4710 shows that this change in local mean refractive index was captured by δp values at the fixed optical depth location of 4.5 μm. Next, keeping the local mean refractive index constant, and changing the local spatial correlation length of the axial refractive index profile within the same region as the previous example, it was observed that δp also captured the change in $l_c$. This is shown in FIG. 48, illustrating the relationship between δp and the profile correlation length δl (nm), where the change in $l_c$ was again detected at the 4.5 μm optical-depth location. Combining the above two results, it was observed that to a first approximation δp ∝ δ$l_c$. Image 4800 shows the mean refractive index within the region delineated by the rectangular-box, and image 4810 shows the change in profile correlation length, $l_c$.

Figure 49:
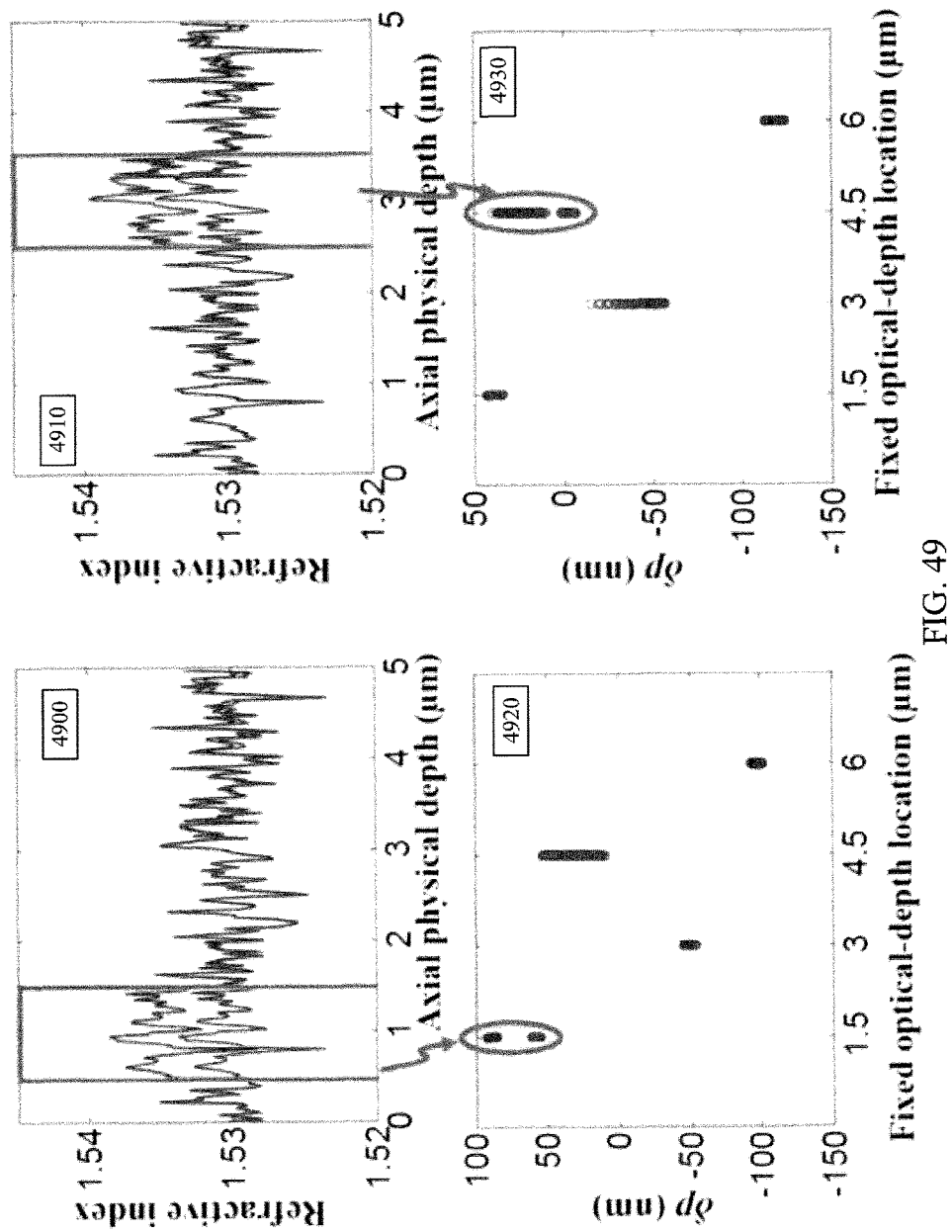
FIG. 49 illustrates the depth-resolved sub-resolution change in OPL ($\delta p$).

Two scenarios are presented in FIG. 49—showing the depth-resolved sub-resolution change in OPL (δp)—to illustrate the feasibility of the depth-resolved feature vector to capture sub-resolution nanoscale structural changes at different sample depths. Image 4900 shows the first example where a significant change in mean refractive index occurs in the sample-section ranging from 0.5 μm to 1.5 μm, and 4910 shows an example where the mean refractive index primarily changes within the range of 2.5 μm to 3.5 μm. For the first scenario, four hundred refractive index profiles were generated using the GRF model with the same δn and $l_c$ to represent the complexity present in biological samples. Two hundred of these profiles (exemplified by the blue refractive index profile in 4900) were considered as is, while for the remaining two hundred profiles an average offset of 0.005 was added to δn within the sample-section ranging from 0.5 μm to 1.5 μm (red refractive index profile in 4900). The same steps were followed to realize the second scenario, except that in that scenario, as shown in 4910, the average offset was added to the sample-section ranging from 2.5 μm to 3.5 μm. Images 4920 and 4930 show the corresponding calculated δp values for the two scenarios at the four fixed optical-depth locations of 1.5 μm, 3 μm, 4.5 μm, and 6 μm. For each refractive index profile, the δp values at the specified locations resulted in a depth-resolved structural feature vector. As can be seen in 4920 and 4930, the change in mean refractive index δn within the sample depth range of 0.5 μm to 1.5 μm and depth range of 2.5 μm to 3.5 μm was captured at the corresponding optical depth location of 1.5 μm and 4.5 μm, respectively. Thus, due to the depth-resolved nature of the measured δp values, the structural feature-vector components were well-separated at the specified fixed optical depths where the structural changes occurred. For the rest of the optical depths with the same local mean refractive index δn, the structural feature-vector components overlapped.

Experimental Results

Experimental Demonstration of Coherence Gating

The above simulations have numerically shown that implicit coherence gating can be employed to obtain a depth-resolved structural feature vector that captures the sub-resolution structural changes at different, but fixed sample depths inside the sample, independent of section thickness. The following experimental results validate the use of implicit coherence gating.

Figure 50:
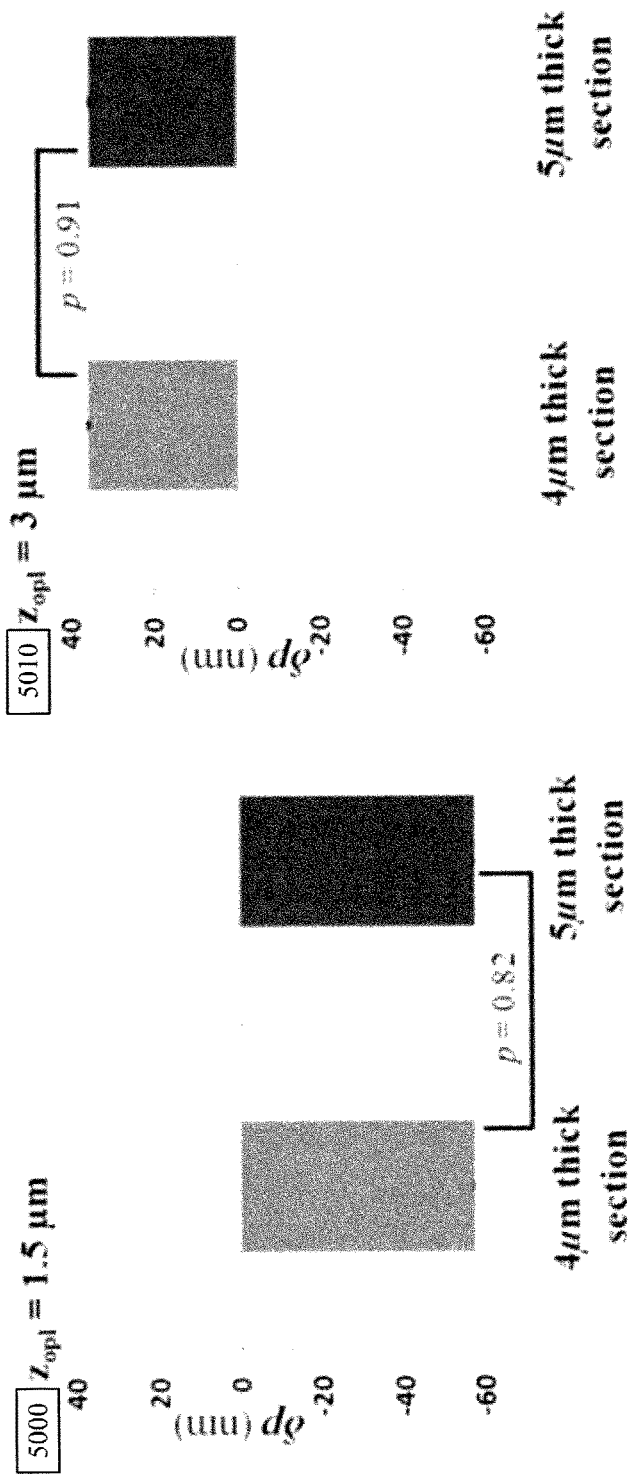
FIG. 50 illustrates the depth-resolved sub-resolution change in OPL ($\delta p$) for 4 µm and 5 µm thick sections at fixed optical-depth locations within the tissue section of 1.5 µm and 3 µm.

The experiments used serial tissue sections of the small intestinal tissue from a normal mouse sectioned at two different thicknesses—4 μm and 5 μm—using a microtome, placed on the coated glass slide, coverslipped with a mounting medium (n=1.50), without any staining. As the tissue sections were serial sections of the same tissue segment, it was reasonable to assume that these two tissue sections had similar structural properties, but different thickness. With the SL-QPM instrument, the experiment analyzed the spectral interference signal for each (x,y) pixel location from a similar tissue area—expressed as a function of spatial frequency K. The spectral signal was Fourier-transformed to get the axial OPL profile of the sample at (x,y) location from which, using equation 3, δp(x, y, $z_{olp}$) at $z_{opl}$=1.5 μm and 3 μm was then extracted. Based on the simulation results, it appeared that the implicit coherence gating should ensure that the δp values measured at the two optical depth locations inside the tissue section should not be affected by the section thickness. FIG. 50 illustrates the depth-resolved sub-resolution change in OPL (δp) for 4 μm and 5 μm thick sections at fixed optical-depth locations within the tissue section of 1.5 μm and 3 μm. Images 5000 and 5010 show the δp values for 4 µm and 5 µm thick sections at optical depths of 1.5 µm and 3 µm respectively. The results shown in FIG. 50 clearly show that the δp values at the two optical depths were independent of the section thickness, as predicted based on the simulation results.

System Stability

Figure 51:
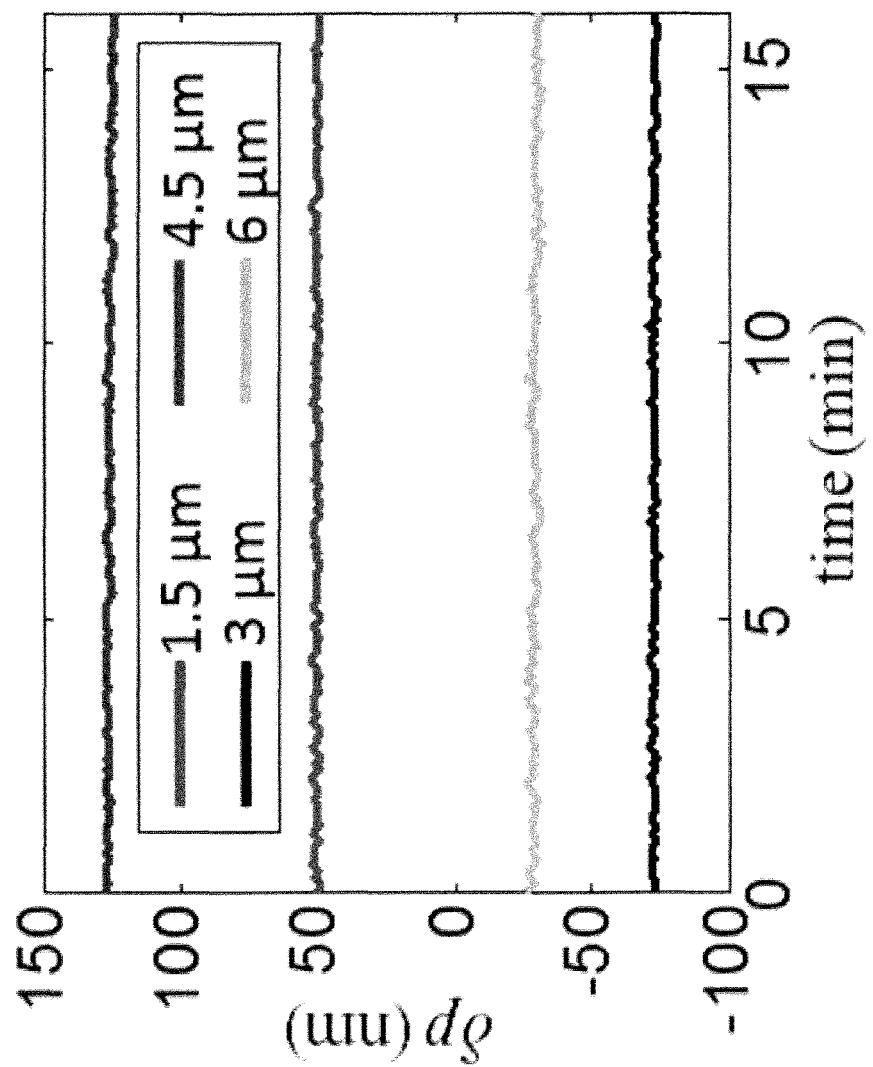
FIG. 51 illustrates the temporal stability of depth-resolved $\delta p$ values as a function of time at four fixed optical depth locations.

The temporal stability of the depth-resolved δp values at the fixed optical depth locations of 1.5 µm, 3 µm, 4.5 µm, and 6 µm were investigated by plotting them as a function of time. FIG. 51 illustrates these results, showing the temporal stability of depth-resolved δp values as a function of time at four fixed optical depth locations. As can be seen these depth-resolved values were relatively stable with a standard deviation from the mean value of around 1 nm. Specifically, the standard deviation due to temporal fluctuations in δp values at the optical depth locations of 1.5 µm, 3 µm, 4.5 µm, and 6 µm was 0.76 nm, 0.78 nm, 0.86 nm and 1.2 nm respectively. The measurements were made on a phantom consisting of a monolayer of 0.75 µm polystyrene microspheres sandwiched between two 2 µm thick paraffin layers. The system SNR was 33 dB.

Experiments with Biological Cells

As shown above, there are two major structural characteristics that can change the structural feature vector: the mean refractive index δn associated with the macromolecular density, and the spatial correlation length of refractive index $l_c$ associated with the spatial scale of macromolecular structures. The experiments investigated two important cancer-related biological processes in which an immortalized cancer cell line is treated with drugs that induce changes in these two types of structural characteristics as proof-of-concept demonstration. In the first such experiment, the cell proliferation and division process is modulated by thymidine and nocodazole during cell cycle to double the DNA content in the cell nucleus and increase the nuclear density and refractive index (δn). The second such experiment investigated the structural changes as a result of histone acetylation, induced by Trichostatin A (TSA), a histone deacetylase (HDAC) inhibitor. The histone acetylation is a well-known epigenetic change to control the gene activity. It has previously been shown using transmission electron microscopy and confocal microscopy that there is a subsequent local relaxation of chromatin or chromatin decondensation, which is expected to increase the chromatin structural correlation length ($l_c$).

Regulation of Cell Proliferation

The cell proliferation experiment analyzed the nuclear structural changes in HeLa cells in response to drugs that modulate the cell proliferation. Cells were first treated with double-thymidine, which inhibited the DNA synthesis and arrested cells at G1/S phase; and then treated with nocodazole, which prevented cell division to arrest cells at G2/M phase, resulting in doubled DNA content in the cell nucleus and thus higher nuclear density and refractive index. Such cell synchronization process also populates most cells at a distinct phase, thus reducing the heterogeneity in the cell population in each phase.

Figure 52:
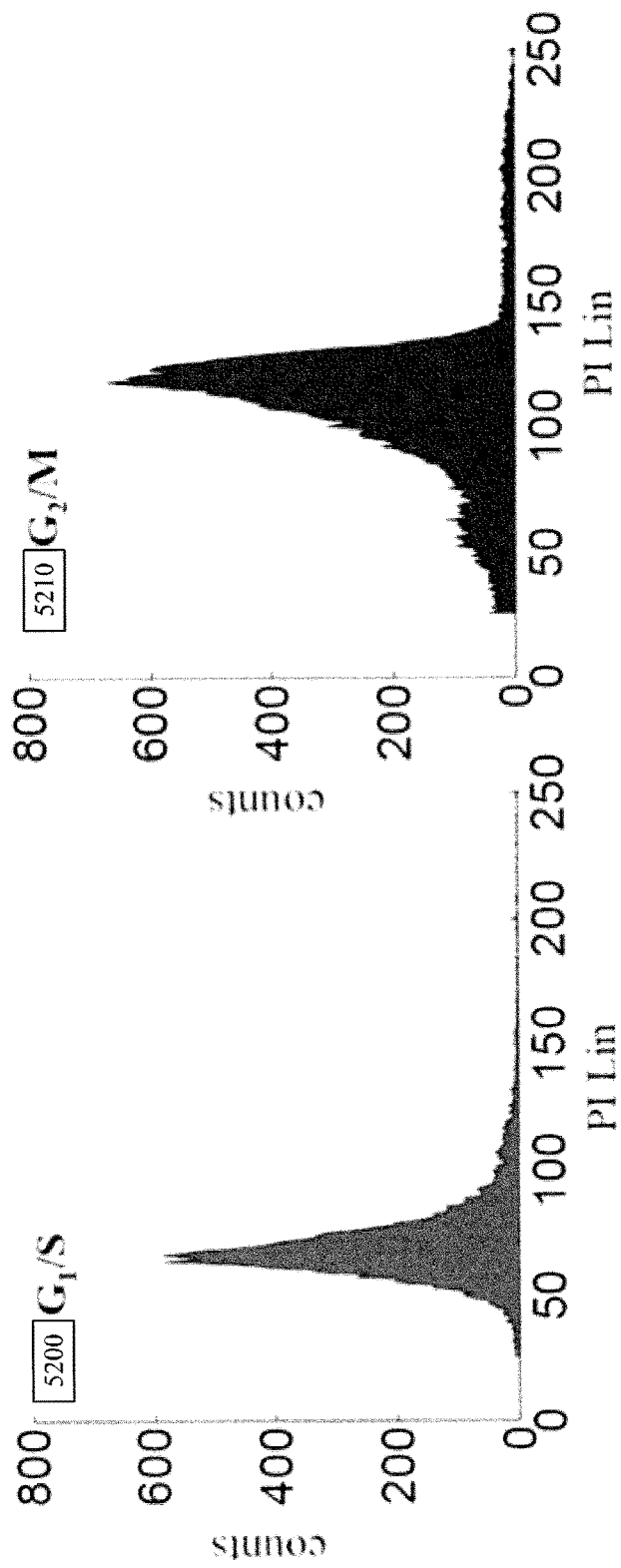
FIG. 52 illustrates flow cytometry of HeLa cells arrested at $G_1/S$-phase and at $G_2/M$-phase.

HeLa cells were grown in Dulbecco's Modified Eagle Medium (DMEM) supplemented with 10% fetal bovine serum (FBS) (Mediatech, Inc) and 1% penicillin-streptomycin in a 70% humidified incubator at 37° C. and 5% $CO_2$. Cells were treated using a protocol based on double-thymidine block followed by nocodazole. As confirmed by FIG. 52, illustrating flow cytometry of HeLa cells arrested at $G_1$/S-phase and at $G_2$/M-phase, 81% of the cells are arrested at $G_1$/S phase as seen in 5200 and 70% of the cells are arrested at $G_2$/M phase as seen in 5210. The DNA content of the nucleus at the $G_2$/M phase was indeed double that of the cells at $G_1$/S phase. Next a cell block was prepared to mimic the clinical sample preparation, which was then sectioned at 5 µm. The cell-block section was placed on a coated glass slide (80T/20R), de-paraffinized and coverslipped with a mounting medium (n=1.50), without any staining.

Figure 53:
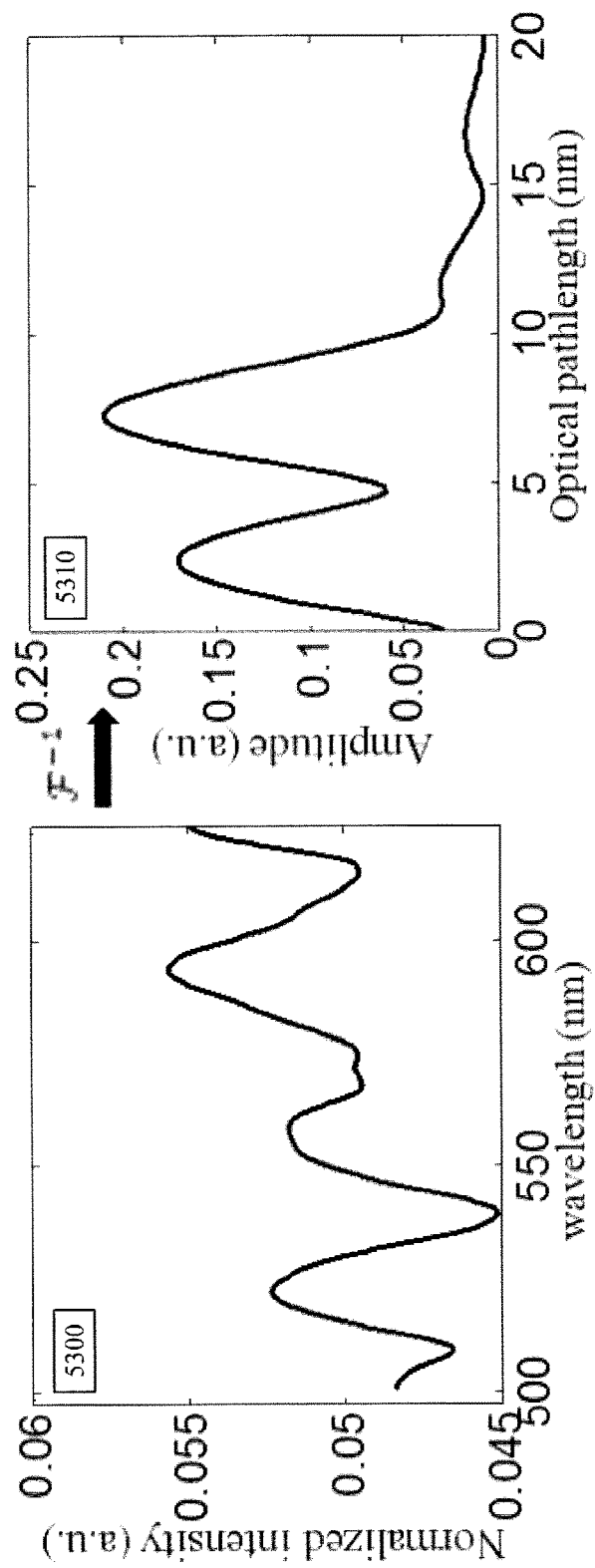
FIG. 53 illustrates an example of a measured spectral signal $I(x,y,\lambda)$ from a cell nucleus at and its Fourier transform after removing the bias term.

The cell nuclei could be easily identified in the bright-field image. With the SL-QPM instrument, for each (x,y) pixel location within the cell nuclei, the spectral signal was obtained as a function of spatial frequency K. The Fourier-transform of the spectral signal gave the axial OPL profile of the sample at the (x,y) location. FIG. 53 shows an example of a measured spectral signal I(x,y,λ) from a cell nucleus at 5300 and its Fourier transform after removing the bias term at 5310. Using equation 3, δp(x, y, $z_{opt}$) was then extracted from the axial OPL profile at optical depths of 1.5 µm, 3 µm, 4.5 µm and 6 µm. The resulting depth-resolved structural feature vectors for all (x, y) pixel locations were averaged over the pixel locations within the cell nucleus to generate a mean depth-resolved structural feature vector for every cell nucleus. 90 cell nuclei were analyzed for each phase.

Figure 54:
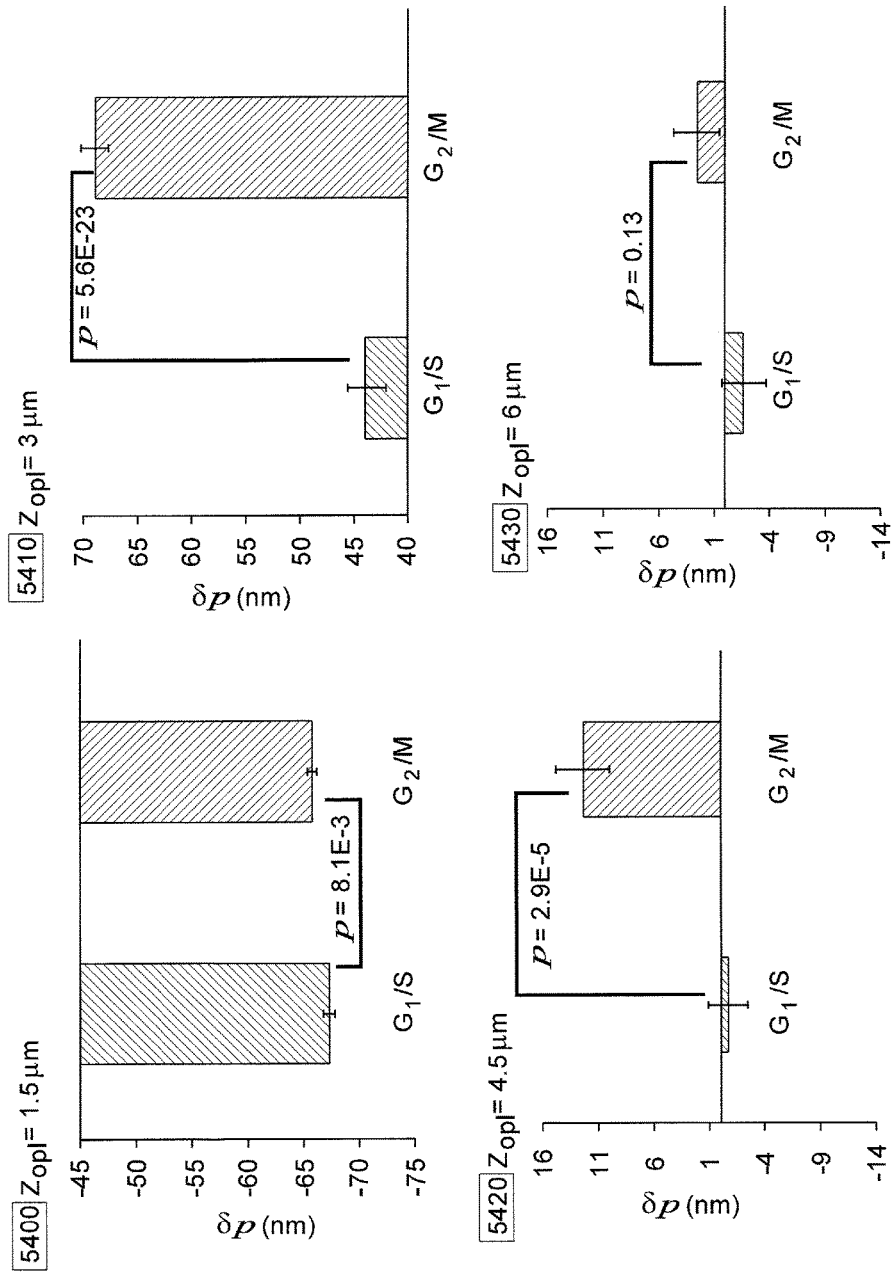
FIG. 54 illustrates the depth-resolved sub-resolution change in OPL ($\delta p$) at four fixed optical-depth locations within the nuclei for cells at $G_1/S$ and $G_2/M$ phase.
Figure 55:
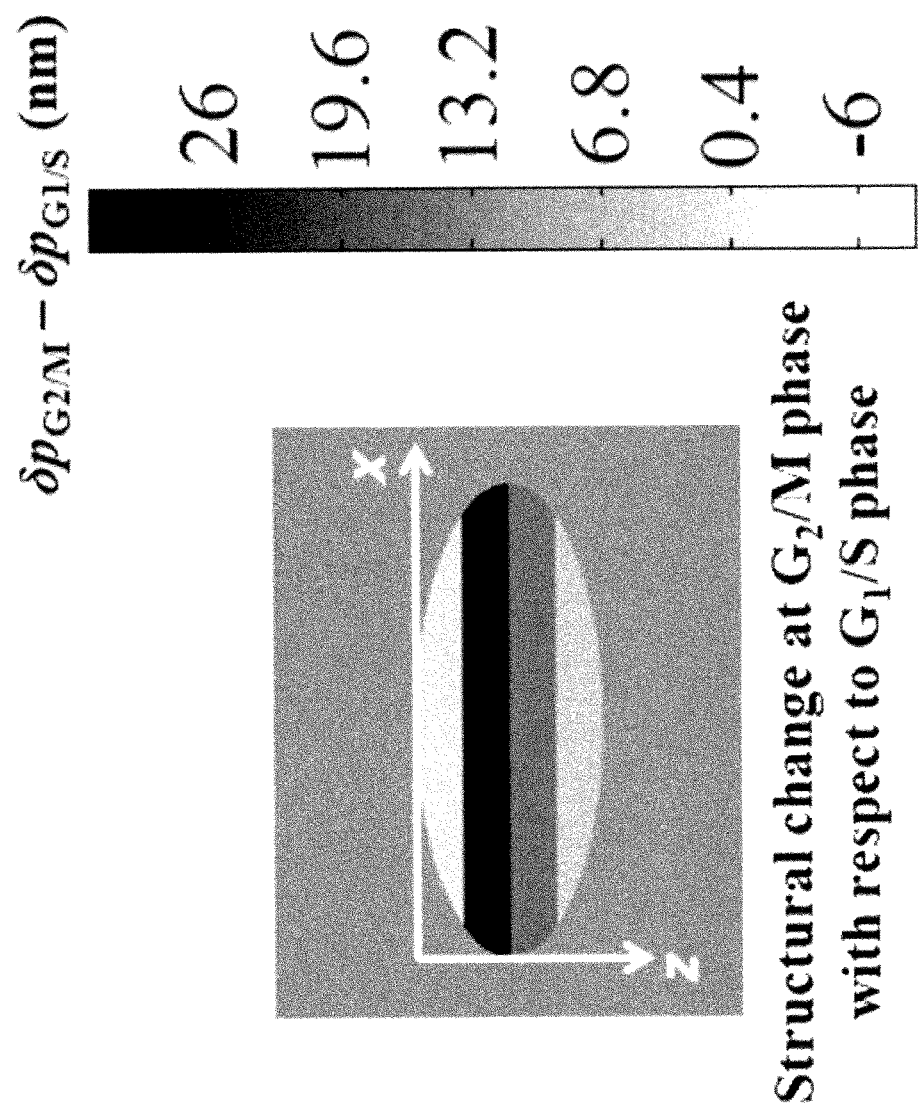
FIG. 55 illustrates the depth-resolved distribution of altered nuclear density in cells at $G_2/M$ phase compared to $G_1/S$ phase.

FIG. 54 shows the depth-resolved sub-resolution change in OPL (δp) at four fixed optical-depth locations within the nuclei for cells at $G_1$/S and $G_2$/M phase. The two-sided p-value is shown on each figure, calculated from the student t-test. FIG. 54 shows the comparison of δp at optical-depth locations of 1.5 µm, 3 µm, 4.5 µm and 6 µm within the cell nuclei for cells at $G_1$/S and $G_2$/M phases. Overall, a significant increase in the average δp was seen at three out of four optical depths (1.5, 3 and 4.5 µm) within cell nuclei at $G_2$/M phase compared to those at $G_1$/S phase. The doubled DNA content at $G_2$/M phase increased the nuclear density and refractive index (δn), resulting in a higher δp. In particular, the depth-resolved δp shows that the most statistically significant change was observed at the optical depth location of 3 µm, which approximately corresponded to the middle part of the cell nucleus. The depth-resolved average nuclear structural change between cells at $G_2$/M and $G_1$/S phases, quantified by $\delta(\delta p)=\delta p_{G2/M}-\delta p_{G1/S}$, is presented in FIG. 55 for graphic visualization. It shows a heterogeneous distribution of altered nuclear density at different optical-depth locations, with the most significant changes occurring at the center of the cell nuclei (indicated by the darker areas in FIG. 55) for this sample set.

Histone Acetylation

Figure 56:
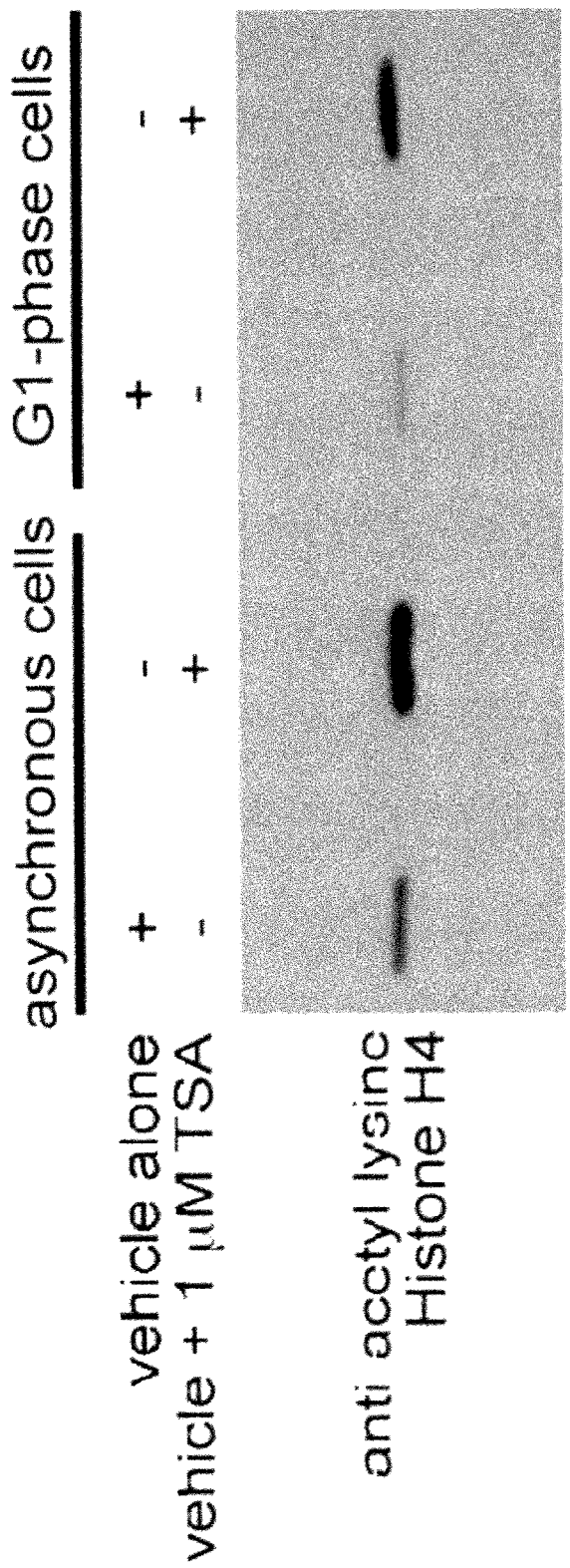
FIG. 56 illustrates an immunoblot of acetyl-Histone H4 in asynchronous and synchronized G1-phase HeLa cells treated with vehicle or TSA for 6 hours.

A further experiment investigated the depth-resolved structural change in cells following histone acetylation, which were treated with TSA, a histone deacetylase inhibitor that induces chromatin decondensation. Chromatin decondensation was anticipated to be associated with a more "loosened" chromatin conformation and an increased correlation length was therefore anticipated. FIG. 56 illustrates an immunoblot of acetyl-Histone H4 in asynchronous and synchronized G1-phase HeLa cells treated with vehicle or TSA for 6 hours. Increased acetyl-Histone H4 associated with chromatin decondensation was seen in cells treated with TSA. Asynchronous HeLa cells were treated with either 1 µM DMSO (vehicle) or 1 µM TSA in DMSO for 6 h (shown in FIG. 56, in lanes 1 and 2 on the left). HeLa cells were also synchronized using the double-thymidine block protocol described above with the single modification that 1 µM DMSO or 1 µM TSA in DMSO were added in addition to the 2 mM thymidine at 30 h (shown in FIG. 56, in lanes 3 and 4 on the right). Whole cell lysates were prepared in 50 mM Tris-HCl pH 7.5, 150 mM NaCl, 50 mM NaF, 1% Tween-20, 0.5% NP40, and 1× protease inhibitor mixture (Roche Applied Science, Indianapolis, Ind.) on ice for 30 min. Cleared cell lysates were resolved in 4-12% Bis-Tris gels (Invitrogen, Carlsbad, Calif.) and immunoblotted with anti-acetyl-Histone H4 primary antibody (Upstate Biotechnology, Lake Placid, N.Y.). Increased histone acetylation was seen in both asynchronous and synchronized $G_1$-phase populations of HeLa cells treated with TSA (shown in FIG. 56, in lanes 2 and 4, respectively). Cell blocks were generated using synchronized $G_1$-phase populations of HeLa cells and 5 μm sections were mounted onto a glass slide without any staining as described above.

The depth-resolved structural feature vector was extracted from about 70-75 cell nuclei of control and TSA-treated synchronized G1-phase populations of HeLa cells respectively.

Figure 57:
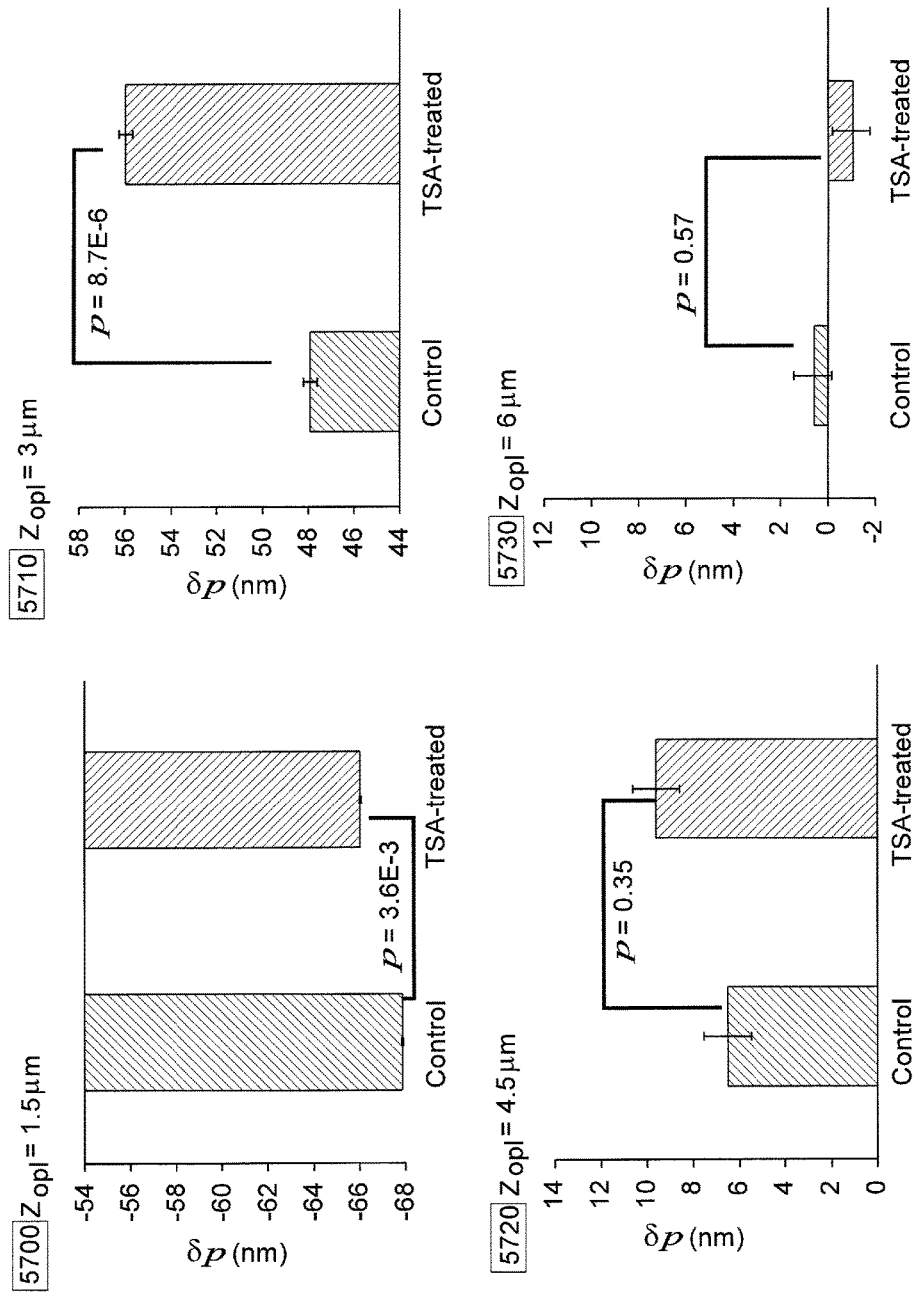
FIG. 57 shows the $\delta p$ values, which quantify depth-resolved sub-resolution structural change in OPL, at four fixed optical-depth locations of 1.5 µm, 3 µm, 4.5 µm and 6 µm within the cell nucleus for the control and TSA-treated cells.
Figure 58:
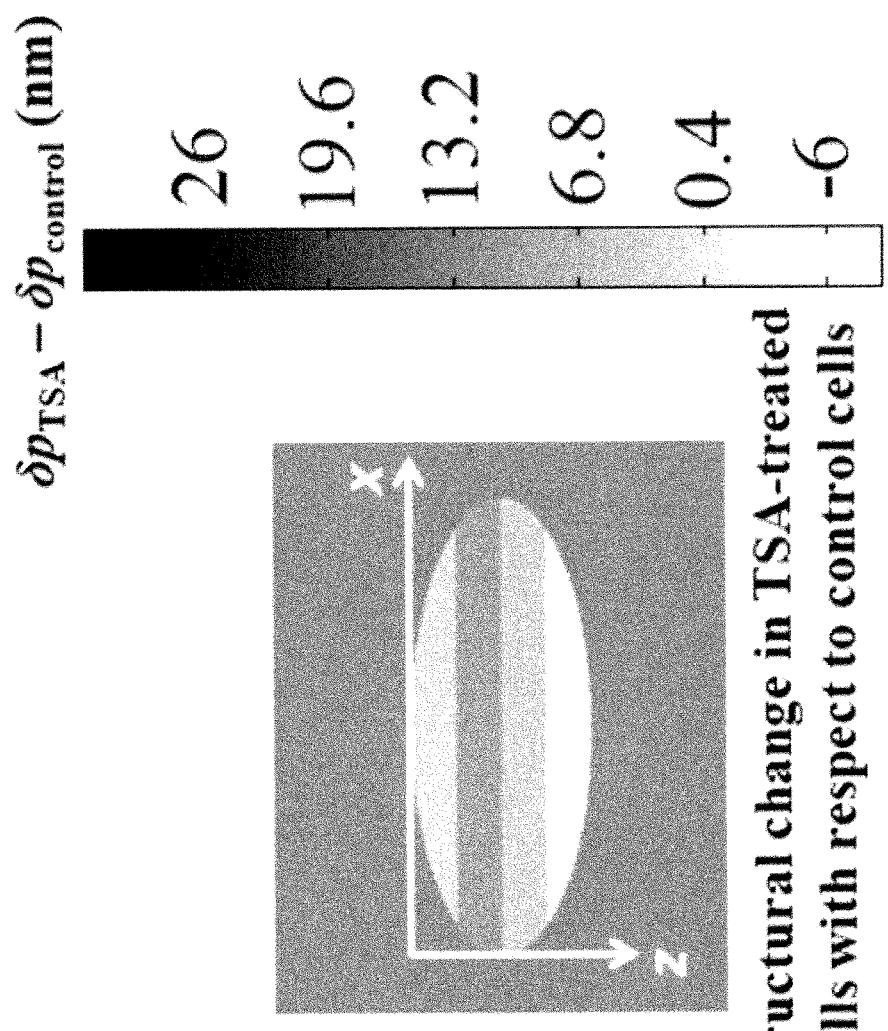
FIG. 58 illustrates the depth-resolved changes in nuclear structural feature vector distribution for the TSA-treated cells when compared to control cells.

FIG. 57 shows the δp values, which quantify depth-resolved sub-resolution structural change in OPL, at four fixed optical-depth locations of 1.5 μm, 3 μm, 4.5 μm and 6 μm within the cell nucleus for the control and TSA-treated cells, at 5700, 5710, 5720, and 5730, respectively. The graphic visualization of the depth-resolved average nuclear structural feature vector changes, quantified by $\delta(\delta p) = \delta p_{TSA} - \delta p_{control}$, is shown in FIG. 58, illustrating the depth-resolved changes in nuclear structural feature vector distribution for the TSA-treated cells when compared to control cells. A statistically significant increase in the average δp was observed at two optical depths (1.5 and 3 μm) within cell nuclei for TSA-treated cells compared to the control cells, with the central location (one coherence length centered around 3 μm) exhibiting the most significant difference (P=8.7E-6). The nuclear density in control and TSA-treated cells was similar, as both cell groups were synchronized at $G_1/S$ phase. As suggested by the simulation results shown in FIG. 48, the increased δp value in TSA-treated cells was attributed to chromatin decondensation and the increased correlation length due to TSA-induced histone acetylation. The depth-resolved structural feature vector indeed captured such nanoscale chromatin conformational changes within the cell nucleus. The SL-QPM systems and methods disclosed herein, given experimentally reasonable SNR levels, can utilize the coherence gating implicit in spectral-domain interferometry to generate a depth-resolved structural feature vector, which can capture sub-resolution axial nanoscale structural changes at fixed sample optical depths that are at least one coherence length apart. Notably, the depth-resolved structural feature vector is independent of sample thickness. This approach is applicable to the analysis of depth-resolved nanoscale-sensitive structural characteristics directly on the clinically prepared unstained sample. Results presented herein have demonstrated that the depth-resolved structural changes can provide insights into the structural transformation during the regulation of cell proliferation through cell cycle and chromatin decondensation induced by histone acetylation, and have the potential to be used as diagnostic markers for improving cancer diagnosis or characterizing the effect of pharmacological compounds.

FURTHER APPLICATIONS AND HISTORY

Systems and methods of the subject innovation can be used to study small-scale changes on a sub-cellular level, having numerous potential applications in medicine, biology, research, etc. These systems and methods are sensitive to small changes in cell structure, and can be used for cancer detection, even in the early stages of tumorigenesis. Additionally, data analytic techniques described herein can provide quantitative information in a variety of settings in which such information was not previously available. Potential applications include those described above, as well as others, including the following areas: pancreatic, esophageal, inflammatory bowel disease, kidney, breast cancer, cervical cancer, ulcerative colitis, improving urine cytology for bladder diseases, and many other scenarios and diseases, cancerous and otherwise.

Systems and methods of the subject innovation can be used to obtain internal structural information with nanoscale resolution based on measuring the elastic backscattering properties. Techniques described herein can be used to characterize of internal structures of cell nuclei of histology slide. Various statistical parameters have shown to be capable of detecting subtle changes in the cell nuclei. The subject innovation can be used in a variety of applications, including detecting disease-specific cellular changes and providing diagnostic information.

In aspects, the subject innovation can be used for detection or for diagnostics. Particularly for patients with conditions having a high-risk of developing tumors, the subject innovation can readily be integrated into preventive screening. Because of the simultaneous high sensitivity and high specificity that can be achieved with systems and methods of the subject innovation, it can be useful both for diagnostics, including improving cytology to obtain the best data from biopsies, and for preventive screening.

Embodiments of the subject innovation can provide better information for cells that look normal or indeterminate to conventional cytology. These systems and methods can be employed in addition to traditional methods, because as explained above, both untreated samples and stained samples can be analyzed according to techniques described herein. Incorporation of the subject innovation can also reduce the number of biopsies necessary to obtain a definitive diagnosis.

Although specific optical parameters are derived and applied herein, it should be understood that other optical parameters can also be included, such as those which capture information about values of optical properties discussed herein, such as path length, index of refraction, amplitude, and intensity, as well as other parameters derived from these or combinations of these, such as parameters reflecting average or global values across a sample, local values, variations in local or global values, extent to which these values vary, ratios or other parameters that describe fluctuations in these values, scales (e.g., distance, etc.) over which these values vary, and other parameters (e.g., means, standard deviations, entropies, etc. associated with these parameters, etc.).

Additionally, because of the nanoscale sensitivity (on the order of 0.9 nm) of the optical systems and methods described herein, the subject innovation can have application in a wide range of other fields wherein instrumentation or techniques with such a level of sensitivity and resolution could prove useful or advantageous. Some such applications could involve nanotechnology, nanoparticles such as nanospheres, thin films, as well as other applications in fields and industries wherein nanoscale resolution would be advantageous.

What has been described above includes examples of the innovation. It is, of course, not possible to describe every conceivable combination of components or methodologies for purposes of describing the subject innovation, but one of ordinary skill in the art may recognize that many further combinations and permutations of the innovation are possible. Accordingly, the innovation is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A spatial-domain low-coherence quantitative phase microscopy apparatus, comprising:
    a light source that produces white light;
    an acousto-optical tuned filter (AOTF) that scans wavelengths to tune the white light;
    optics that project the tuned light onto a sample, wherein the sample scatters at least a portion of the tuned light back;
    a camera that records the scattered portion of the tuned light, wherein the camera records based at least in part on the wavelengths scanned by the AOTF; and
    a data analysis component that analyzes the data recorded by the camera, wherein the data analysis component quantifies changes in optical path length at a plurality of predetermined depth locations within the sample below a surface of the sample and generates a depth-resolved three-dimensional structural feature vector based on the quantified changes in optical path length to capture sub-resolution axial nanoscale structural changes in the sample, wherein a distance between each of the predetermined depth locations is at least one coherence length of a correlation function of the light source.

2. The apparatus of claim 1, wherein the sample is covered by a glass slide, wherein one face of the glass slide is covered by a reflection-enhancing coating.

3. The apparatus of claim 1, further comprising a transmission mode.

4. The apparatus of claim 1, wherein the camera records a matrix, wherein the matrix comprises an x-axis corresponding to a wavelength of the recorded light and a y-axis corresponding to the spatial position.

5. The apparatus of claim 4, wherein the data analysis component produces a three-dimensional intensity cube $I(x, y, k)$, based at least in part on the matrix recorded by the camera and a wavenumber k.

6. The apparatus of claim 1, wherein the data analysis component analyses the data for phase information to extract three dimensional information.

7. The apparatus of claim 1, wherein the sample contains one or more stains, and wherein the data analysis component determines a correction to apply to the recorded data to account for the one or more stains.

8. A spatial-domain low-coherence quantitative phase microscopy method, comprising:
    producing white light from a light source; tuning the white light with an acousto-optical tuned filter (AOTF);
    projecting the tuned light onto a sample, wherein the sample scatters at least a portion of the tuned light back;
    recording the scattered portion of the tuned light with a camera; and
    measuring the recorded scattered portion including quantifying changes in optical path length at a plurality of predetermined depth locations within the sample below a surface of the sample and generating a depth-resolved three-dimensional structural feature vector based at least in part on the quantified changes in optical path length and determining sub-resolution axial nanoscale structural changes in the sample based at least in part on the depth-resolved three-dimensional structural feature vector, wherein a distance between each of the predetermined depth locations is at least one coherence length of a correlation function of the light source.

9. The method of claim 8, further comprising covering the sample by a glass slide, wherein one face of the glass slide is covered by a reflection-enhancing coating.

10. The method of claim 8, further comprising recording a matrix, wherein the matrix comprises an x-axis corresponding to a wavelength of the measured light and a y-axis corresponding to the spatial position.

11. The method of claim 10, further comprising producing a three-dimensional intensity cube $I(x, y, k)$, based at least in part on the matrix recorded by the camera and a wavenumber k.

12. The method of claim 8, further comprising determining a correction to apply to the recorded data to account for one or more stains present in the sample.

13. A spatial-domain low-coherence quantitative phase microscopy apparatus, comprising:
    means for producing white light from a light source;
    means for tuning the wavelength of white light; means for projecting the tuned light onto a sample, wherein the sample scatters at least a portion of the light back;
    means for recording the scattered portion; means for measuring the recorded light;
    means for generating a depth-resolved three-dimensional structural feature vector at a set of a plurality of predetermined depth locations based at least in part on the measured recorded light; and
    means for determining sub-resolution axial nanoscale structural changes in the sample based at least in part on the depth-resolved three-dimensional structural feature vector including by quantifying changes in optical path length at the plurality of predetermined depth locations to remove an effect of a thickness of the sample, wherein a distance between each of the predetermined depth locations is at least one coherence length of a correlation function of the light source.

14. The apparatus of claim 13, wherein the means for measuring further record a matrix, wherein the matrix comprises an x-axis corresponding to a wavelength of the measured light and a y-axis corresponding to the spatial position.

15. The apparatus of claim 13, further comprising means for producing a three-dimensional intensity cube $I(x, y, k)$, based at least in part on the recorded matrix and a wavenumber k.

* * * * *